United States Patent
Jewett et al.

(10) Patent No.: US 12,098,433 B2
(45) Date of Patent: Sep. 24, 2024

(54) ON DEMAND, PORTABLE, CELL-FREE MOLECULAR SENSING PLATFORM

(71) Applicant: NORTHWESTERN UNIVERSITY, Evanston, IL (US)

(72) Inventors: Michael Christopher Jewett, Evanston, IL (US); Julius B. Lucks, Evanston, IL (US); Adam D. Silverman, Chicago, IL (US); Khalid K. Alam, Evanston, IL (US)

(73) Assignee: Northwestern University, Evanston, IL (US)

( * ) Notice: Subject to any disclaimer, the term of this patent is extended or adjusted under 35 U.S.C. 154(b) by 867 days.

(21) Appl. No.: 17/265,785

(22) PCT Filed: Aug. 5, 2019

(86) PCT No.: PCT/US2019/045116
§ 371 (c)(1),
(2) Date: Feb. 3, 2021

(87) PCT Pub. No.: WO2020/072127
PCT Pub. Date: Apr. 9, 2020

(65) Prior Publication Data
US 2021/0164059 A1    Jun. 3, 2021

Related U.S. Application Data

(60) Provisional application No. 62/714,427, filed on Aug. 3, 2018.

(51) Int. Cl.
C12Q 1/6897    (2018.01)
C12Q 1/48    (2006.01)
(Continued)

(52) U.S. Cl.
CPC .......... *C12Q 1/6897* (2013.01); *C12Q 1/485* (2013.01); *G01N 33/1826* (2013.01);
(Continued)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |

(Continued)

FOREIGN PATENT DOCUMENTS

| | | |
|---|---|---|
| WO | 2003056914 A1 | 7/2003 |
| WO | 2004013151 A2 | 2/2004 |

(Continued)

OTHER PUBLICATIONS

Salehi, Amin; et al; "Cell-Free Protein Synthesis Approach to Biosensing hTRß-Specific Endocrine Disruptors" Analytical Chemistry, 89, 3395-3401, 2017 (Year: 2017).*

(Continued)

*Primary Examiner* — David W Berke-Schlessel
(74) *Attorney, Agent, or Firm* — Quarles & Brady LLP

(57) ABSTRACT

Disclosed are methods, devices, kits, components, and compositions for detecting a target molecule in a test sample using a cell-free protein synthesis (CFPS) reaction. The methods, devices, kits, components, and compositions may be utilized for detecting target molecules which may include small molecules and/or metabolites of small molecules. The components and compositions used in the disclosed methods, devices, and kits may be dried or lyophilized and may be present or immobilized on a paper substrate, for example, as a paper test article.

21 Claims, 44 Drawing Sheets

(51) Int. Cl.
*G01N 33/18* (2006.01)
*G01N 33/52* (2006.01)

(52) U.S. Cl.
CPC ......... *G01N 33/521* (2013.01); *G01N 33/184* (2024.05); *G01N 2430/20* (2013.01)

(56) References Cited

U.S. PATENT DOCUMENTS

| | | |
|---|---|---|
| 4,683,202 A | 7/1987 | Mullis |
| 5,478,730 A | 12/1995 | Alakhov et al. |
| 5,494,810 A | 2/1996 | Barany |
| 5,556,769 A | 9/1996 | Wu et al. |
| 5,665,563 A | 9/1997 | Beckler |
| 6,168,931 B1 | 1/2001 | Swartz et al. |
| 6,518,058 B1 | 2/2003 | Biryukov et al. |
| 6,548,276 B2 | 4/2003 | Swartz |
| 6,783,957 B1 | 8/2004 | Biryukov et al. |
| 6,869,774 B2 | 3/2005 | Endo et al. |
| 6,994,986 B2 | 2/2006 | Swartz et al. |
| 7,008,651 B2 | 3/2006 | Ambuel |
| 7,118,883 B2 | 10/2006 | Inoue et al. |
| 7,186,525 B2 | 3/2007 | Sakanyan |
| 7,189,528 B2 | 3/2007 | Higashide et al. |
| 7,235,382 B2 | 6/2007 | Endo |
| 7,273,615 B2 | 9/2007 | Endo |
| 7,312,049 B2 | 12/2007 | Calhoun |
| 7,338,789 B2 | 3/2008 | Swartz et al. |
| 7,387,884 B2 | 6/2008 | Suzuki et al. |
| 7,396,664 B2 | 7/2008 | Daly |
| 7,399,610 B2 | 7/2008 | Shikata et al. |
| 7,776,535 B2 | 8/2010 | Mehl |
| 7,817,794 B2 | 10/2010 | Galvin |
| 8,298,759 B2 | 10/2012 | Voloshin |
| 8,357,529 B2 | 1/2013 | Swartz |
| 8,574,880 B2 | 11/2013 | Bond |
| 8,703,471 B2 | 4/2014 | Aebi |
| 8,715,958 B2 | 5/2014 | Goerke |
| 8,734,856 B2 | 5/2014 | Endo |
| 8,999,668 B2 | 4/2015 | Delisa |
| 9,005,920 B2 | 4/2015 | Kusumegi |
| 9,410,170 B2 | 8/2016 | Calhoun |
| 9,528,137 B2 | 12/2016 | Jewett |
| 2004/0209321 A1 | 10/2004 | Swartz et al. |
| 2005/0170452 A1 | 8/2005 | Wildt |
| 2006/0211085 A1 | 9/2006 | Bobrowicz |
| 2006/0234345 A1 | 10/2006 | Schwartz et al. |
| 2006/0252672 A1 | 11/2006 | Betenbaugh |
| 2006/0257399 A1 | 11/2006 | Gerngross |
| 2006/0286637 A1 | 12/2006 | Hamilton |
| 2007/0026485 A1 | 2/2007 | Defrees |
| 2007/0154983 A1 | 7/2007 | Calhoun et al. |
| 2007/0178551 A1 | 8/2007 | Gerngross |
| 2007/0196812 A1* | 8/2007 | Kobayashi ............ G01N 33/68 435/4 |
| 2008/0138857 A1 | 6/2008 | Swartz et al. |
| 2014/0295492 A1 | 10/2014 | Jewett et al. |
| 2014/0349353 A1 | 11/2014 | Nomura |
| 2016/0060301 A1 | 3/2016 | Jewett |
| 2016/0312312 A1 | 10/2016 | Pardee |
| 2016/0362708 A1 | 12/2016 | Jewett |
| 2017/0073381 A1 | 3/2017 | Jewett |
| 2017/0183664 A1 | 6/2017 | Lucks |
| 2018/0016612 A1 | 1/2018 | Jewett |
| 2018/0016614 A1 | 1/2018 | Jewett |
| 2018/0136197 A1* | 5/2018 | Bundy ................. G01N 33/566 |
| 2021/0163947 A1 | 6/2021 | Silverman |
| 2021/0198678 A1 | 7/2021 | Glasscock |

FOREIGN PATENT DOCUMENTS

| | | |
|---|---|---|
| WO | 2004035605 A2 | 4/2004 |
| WO | 2006102652 A2 | 9/2006 |
| WO | 2006119987 A2 | 11/2006 |
| WO | 2007120932 A2 | 10/2007 |
| WO | 2013032345 A3 | 3/2013 |
| WO | 2014144583 | 9/2014 |
| WO | 2017117539 | 7/2017 |
| WO | 2017205668 A1 | 11/2017 |

OTHER PUBLICATIONS

Khnouf, Ruba; et al; "Detection of ricin in beverages using cell-free protein synthesis in a microfluidic device" Sensors and Actuators B: Chemical, 221, 723-729. 2015 (Year: 2015).*

Kempf, Noemie; et al; "A Novel Method to Evaluate Ribosomal Performance in Cell-Free Protein Synthesis Systems" Scientific Reports, 7, 46753, 2017 (Year: 2017).*

Wen, Ke Yan; et al; "A Cell-Free Biosensor for Detecting Quorum Sensing Molecules in P. aeruginosa-Infected Respiratory Samples" ACS Synthetic Biology, 6, 2293-2301, 2017 (Year: 2017).*

Beaucage, S. L., et al. "Deoxynucleoside phosphoramidites—a new class of key intermediates for deoxypolynucleotide synthesis." Tetrahedron letters 22.20 (1981): 1859-1862.

Bremer, H. et al. *Escherichia coli* and *Salmonella*: Cellular and Molecular Biology. 2 edn, vol. 1 1553-1569 (ASM Press, 1996).

Brown, E. L., et al. "[8] Chemical synthesis and cloning of a tyrosine tRNA gene." Methods in Enzymology. vol. 68. Academic Press, 1979. 109-151.

Bryant, J. A., et al. Chromosome position effects on gene expression in *Escherichia coli* K-12. Nucleic acids research 42, 11383-11392, doi:10.1093/nar/gku828 (2014).

Bundy, B. C. et al. Site-specific incorporation of p-propargyloxyphenylalanine in a cell-free environment for direct protein-protein click conjugation. Bioconjugate chemistry 21, 255-263, doi:10.1021/bc9002844 (2010).

Calhoun, K.A. et al, An economical method for cell-free protein synthesis using glucose and nucleoside monophosphates. Biotechnol Prog, 2005. 21(4): p. 1146-53.

Calhoun, K.A. et al., Energizing cell-free protein synthesis with glucose metabolism. Biotechnol Bioeng, 2005. 90(5): p. 606-13.

Carlson, E. D., et al. Cell-free protein synthesis: applications come of age. Biotechnology advances 30, 1185-1194, doi:10.1016/j.biotechadv.2011.09.016 (2012).

Caschera, F. et al. Synthesis of 2.3 mg/ml of protein with an all *Escherichia coli* cell-free transcription-translation system. Biochimie 99, 162-168, doi:10.1016/j.biochi.2013.11.025 (2014).

Catherine, C. et al. Engineering Thermal Properties of Elastin-like Polypeptides by Incorporation of Unnatural Amino Acids in a Cell-free Protein Synthesis System. Biotechnology and Bioprocess Engineering 20, 417-422, doi:10.1007/s12257-015-0190-1 (2015).

Chappell, J., et al. Validation of an entirely in vitro approach for rapid prototyping of DNA regulatory elements for synthetic biology. Nucleic acids research 41, 3471-3481, doi:10.1093/nar/gkt052 (2013).

Chauhan, J.S., et al, In silico platform for prediction of N-, O- and C-glycosites in eukaryotic protein sequences. PLoS One, 2013. 8(6): p. e67008.

Chen, Y. J. et al. Characterization of 582 natural and synthetic terminators and quantification of their design constraints. Nature methods 10, 659-664, doi:10.1038/nmeth.2515 (2013).

Datsenko, K. A. et al. One-step inactivation of chromosomal genes in *Escherichia coli* K-12 using PCR products. Proceedings of the National Academy of Sciences of the United States of America 97, 6640-6645, doi:10.1073/pnas.120163297 (2000).

Davanloo, P., et al. Cloning and expression of the gene for bacteriophage T7 RNS polymerase. Proceedings of the National Academy of Sciences of the United States of America 81, 2035-2039 (1984).

De Boer, H. A., et al. The tac promoter: a functional hybrid derived from the trp and lac promoters. Proceedings of the National Academy of Sciences of the United States of America 80, 21-25 (1983).

Des Soye, B. J., et al. Repurposing the translation apparatus for synthetic biology. Current opinion in chemical biology 28, 83-90, doi: 10.1016/j.cbpa.2015.06.008 (2015).

Dumas, A. E., et al. Designing logical codon reassignment—Expanding the chemistry in biology. Chemical Science 6, 50-69 (2014).

(56) References Cited

OTHER PUBLICATIONS

Ellinger, T. et al. Single-step purification of T7 RNA polymerase with a 6-histidine tag. BioTechniques 24, 718-720 (1998).

Espah Borujeni, A., et al. Translation rate is controlled by coupled trade-offs between site accessibility, selective RNA unfolding and sliding at upstream standby sites. Nucleic acids research 42, 2646-2659, doi:10.1093/nar/gkt1139 (2014).

Feldman, M.F., et al., Engineering N-linked protein glycosylation with diverse O antigen lipopolysaccharide structures in *Escherichia coli*. Proc Natl Acad Sci U S A, 2005. 102(8): p. 3016-21.

Fritz, B. R., et al. Implications of macromolecular crowding and reducing conditions for in vitro ribosome construction. Nucleic acids research 43, 4774-4784, doi:10.1093/nar/gkv329 (2015).

García-González, V., et al., Regulation of the *Pseudomonas* sp. Strain ADP Cyanuric Acid Degradation Operon. Journal of Bacteriology, 2005. 187(1): p. 155-167.

Gavel, Y. et al, Sequence differences between glycosylated and non-glycosylated Asn-X-Thr/Ser acceptor sites: Implications for protein engineering. Protein Eng, 1990. 3(5): p. 433-42.

Glover, K.J., et al., In vitro assembly of the undecaprenylpyrophosphate-linked heptasaccharide for prokaryotic N-linked glycosylation. Proc Natl Acad Sci U S A, 2005. 102(40): p. 14255-9.

Glover, K.J., et al., Direct biochemical evidence for the utilization of UDP-bacillosamine by PglC, an essential glycosyl-1-phosphate transferase in the Campylobacter jejuni N-linked glycosylation pathway. Biochemistry, 2006. 45 (16): p. 5343-50.

Goodchild, J. "Conjugates of oligonucleotides and modified oligonucleotides: a review of their synthesis and properties." Bioconjugate Chemistry 1.3 (1990): 165-187.

Gottesman, S. Proteases and their targets in *Escherichia coli*. Annual review of genetics 30, 465-506, doi:10.1146/annurev.genet. 30.1.465 (1996).

Grodberg, J. et al. ompT encodes the *Escherichia coli* outer membrane protease that cleaves T7 RNA polymerase during purification. Journal of bacteriology 170, 1245-1253 (1988).

Guarino, C. et al., A prokaryote-based cell-free translation system that efficiently synthesizes glycoproteins. Glycobiology, 2012. 22(5): p. 596-601.

Heinzelman, P., et al. pH responsive granulocyte colony-stimulating factor variants with implications for treating Alzheimer's disease and other central nervous system disorders. Protein engineering, design & selection : PEDS 28, 481-489, doi: 10.1093/protein/gzv022 (2015).

Hodgman, C.E. et al., Cell-free synthetic biology: thinking outside the cell. Metab Eng, 2012. 14(3): p. 261-9.

Hong, S. H. et al. Cell-free protein synthesis from a release factor 1 deficient *Escherichia coli* activates efficient and multiple site-specific nonstandard amino acid incorporation. ACS synthetic biology 3, 398-409, doi:10.1021/sb400140t (2014).

Hong, S. H. et al. Improving Cell-Free Protein Synthesis through Genome Engineering of *Escherichia coli* Lacking Release Factor 1. Chembiochem : a European journal of chemical biology, doi:10. 1002/cbic.201402708 (2015).

Hong, S. H., et al. Non-standard amino acid incorporation into proteins using *Escherichia coli* cell-free protein synthesis. Frontiers in chemistry 2, 34, doi:10.3389/fchem.2014.00034 (2014).

Horton, R. M. PCR-mediated recombination and mutagenesis. SOEing together tailor-made genes. Molecular biotechnology 3, 93-99, doi:10.1007/BF02789105 (1995).

Hua, A., et al., Development of a bacterial bioassay for atrazine and cyanuric acid detection. Frontiers in Microbiology, 2015. 6: p. 211.

Hwang, B. Y. et al. Substrate specificity of the *Escherichia coli* outer membrane protease OmpP. Journal of bacteriology 189, 522-530, doi:10.1128/JB.01493-06 (2007).

Ikeda, R. A. et al. Enzymatic properties of a proteolytically nicked RNA polymerase of bacteriophage T7. The Journal of biological chemistry 262, 3790-3799 (1987).

Ikeda, R. A. et al. Interactions of a proteolytically nicked RNA polymerase of bacteriophage T7 with its promoter. The Journal of biological chemistry 262, 3800-3808 (1987).

Inouye, S. et al. Up-promoter mutations in the lpp gene of *Escherichia coli*. Nucleic acids research 13, 3101-3110 (1985).

International Searching Authority. International Search Report and Written Opinion for application PCT/US2019/045116. Mailed on Apr. 23, 2020. 7 pages.

Jewett, M. C. et al. Mimicking the *Escherichia coli* cytoplasmic environment activates long-lived and efficient cell-free protein synthesis. Biotechnology and bioengineering 86, 19-26, doi:10. 1002/bit.20026 (2004).

Jia, K., et al., A lower limit of detection for atrazine was obtained using bioluminescent reporter bacteria via a lower incubation temperature. Ecotoxicology and Environmental Safety, 2012. 84: p. 221-226.

Karim, A. S. et al. A cell-free framework for rapid biosynthetic pathway prototyping and enzyme discovery. Metabolic engineering 36, 116-126, doi:10.1016/j.ymben.2016.03.002 (2016).

Kwon, Y. C. et al. High-throughput preparation methods of crude extract for robust cell-free protein synthesis. Scientific reports 5, 8663, doi:10.1038/srep08663 (2015).

Laine, R.A., The Information-Storing Potential of the Sugar Code. Glycosciences: Status and Perspectives, 1997: p. 1-14.

Lajoie, M. J. et al. Genomically recoded organisms expand biological functions. Science 342, 357-360, doi:10.1126/science. 1241459 (2013).

Lederberg, J. et al. Replica plating and indirect selection of bacterial mutants. Journal of bacteriology 63, 399-406 (1952).

Li, J. et al. Cell-free protein synthesis enables high yielding synthesis of an active multicopper oxidase. Biotechnology Journal 11, 212-218, doi:10.1002/biot.201500030 (2016).

Lian, Q., et al., The cost-efficiency realization in the *Escherichia coli*-based cell-free protein synthesis systems. Appl Biochem Biotechnol, 2014. 174(7): p. 2351-67.

Linton, D., et al., Identification of N-acetylgalactosamine-containing glycoproteins PEB3 and CgpA in Campylobacter jejuni. Mol Microbiol, 2002. 43(2): p. 497-508.

Liu, C. C. et al. Adding new chemistries to the genetic code. Annual review of biochemistry 79, 413-444, doi:10.1146/annurev.biochem. 052308.105824 (2010).

Martemyanov, K. A., et al. Cell-free production of biologically active polypeptides: application to the synthesis of antibacterial peptide cecropin. Protein expression and purification 21, 456-461, doi:10.1006/prep.2001.1400 (2001).

Maue, A.C., et al., A capsule conjugate vaccine approach to prevent diarrheal disease caused by Campylobacter jejuni. Hum Vaccin Immunother, 2014. 10(6): p. 1499-504.

Mosberg, J. A., et al. Lambda red recombineering in *Escherichia coli* occurs through a fully single-stranded intermediate. Genetics 186, 791-799, doi:10.1534/genetics.110.120782 (2010).

Muller, D. K., et al. Processivity of proteolytically modified forms of T7 RNA polymerase. Biochemistry 27, 5763-5771 (1988).

Narang, S. A., et al. "[6] Improved phosphotriester method for the synthesis of gene fragments." Methods in Enzymology. vol. 68. Academic Press, 1979. 90-98.

Nehring, S., et al. Performance analysis of orthogonal pairs designed for an expanded eukaryotic genetic code. PloS one 7, e31992, doi:10.1371/journal.pone.0031992 (2012).

Ohtsubo, K. et al., Glycosylation in cellular mechanisms of health and disease. Cell, 2006. 126(5): p. 855-67.

Olivier, N.B., et al., In vitro biosynthesis of UDP-N, N'-diacetylbacillosamine by enzymes of the Campylobacter jejuni general protein glycosylation system. Biochemistry, 2006. 45(45): p. 13659-69.

Ollis, A.A., et al., Engineered oligosaccharyltransferases with greatly relaxed acceptor-site specificity. Nat Chem Biol 2014. 10(10): p. 816-22.

Owczarzy, R., et al. "Predicting stability of DNA duplexes in solutions containing magnesium and monovalent cations." Biochemistry 47.19 (2008): 5336-5353.

Pardee, K., et al. "Paper-Based Synthetic Gene Networks." Cell 159(4): 940-954.

Petrov, A. S. et al. RNA-magnesium-protein interactions in large ribosomal subunit. The journal of physical chemistry. B 116, 8113-8120, doi:10.1021/jp304723w (2012).

(56) References Cited

OTHER PUBLICATIONS

Raman, R., et al., Glycomics: an integrated systems approach to structure-function relationships of glycans. Nat Methods, 2005. 2(11): p. 817-24.
Raucher, D. et al. Cell-penetrating peptides: strategies for anticancer treatment. Trends in molecular medicine 21, 560-570, doi:10.1016/j.molmed.2015.06.005 (2015).
Renesto, P. et al. From genes to proteins: in vitro expression of rickettsial proteins. Annals of the New York Academy of Sciences 990, 642-652 (2003).
Salis, H. M., et al. Automated design of synthetic ribosome binding sites to control protein expression. Nature biotechnology 27, 946-950, doi:10.1038/nbt.1568 (2009).
Santoro, S. W., et al. An efficient system for the evolution of aminoacyl-tRNA synthetase specificity. Nature biotechnology 20, 1044-1048, doi:10.1038/nbt742 (2002).
Shin, J. et al. An E. coli cell-free expression toolbox: application to synthetic gene circuits and artificial cells. ACS synthetic biology 1, 29-41, doi:10.1021/sb200016s (2012).
Shin, J. et al. Efficient cell-free expression with the endogenous E. coli RNA polymerase and sigma factor 70. Journal of biological engineering 4, 8, doi:10.1186/1754-1611-4-8 (2010).
Sousa, R. in Encyclopedia of Biological Chemistry vol. 4 (eds William J. Lennarz & M. Daniel Lane) (Elsevier, 2004).
Spiro, R.G., Protein glycosylation: nature, distribution, enzymatic formation, and disease implications of glycopeptide bonds. Glycobiology, 2002. 12(4): p. 43R-56R.
Stefano, J. E. et al. Lac UV5 transcription in vitro. Rate limitation subsequent to formation of an RNA polymerase-DNA complex. Biochemistry 18, 1063-1067 (1979).
Studier, F. W. et al. Use of bacteriophage T7 RNA polymerase to direct selective high-level expression of cloned genes. Journal of molecular biology 189, 113-130 (1986).
Sullivan, C. J. et al. A cell-free expression and purification process for rapid production of protein biologics. Biotechnology journal 11, 238-248, doi:10.1002/biot.201500214 (2016).
Sun, Z.Z., et al., Protocols for Implementing an *Escherichia coli* Based TX-TL Cell-Free Expression System for Synthetic Biology. 2013(79): p. e50762.
Swartz, J. R., et al. Cell-free protein synthesis with prokaryotic combined transcription-translation. Methods in molecular biology (Clifton, N.J.) 267, 169-182, doi:10.1385/1-59259-774-2:169 (2004).
Szymanski, C.M., et al., Evidence for a system of general protein glycosylation in Campylobacter jejuni. Mol Microbiol, 1999. 32(5): p. 1022-30.
Takahashi, M. K. et al. Characterizing and prototyping genetic networks with cell-free transcription-translation reactions. Methods 86, 60-72, doi:10.1016/j.ymeth.2015.05.020 (2015).
Tatusova, T.A. et al. (1999) "Blast 2 sequences—a new tool for comparing protein and nucleotide sequences", FEMS Microbiol Lett. 174:247-250.
Tunitskaya, V. L. et al. Structural-functional analysis of bacteriophage T7 RNA polymerase. Biochemistry. Biokhimiia 67, 1124-1135 (2002).

Wacker et al., "N-linked glycosylation in Campylobacter jejuni and its functional transfer into *E. coli*," Science 2002, Nov. 29; 298(5599):1790-3.
Wang, H. H. et al. Multiplexed genome engineering and genotyping methods applications for synthetic biology and metabolic engineering. Methods in enzymology 498, 409-426, doi:10.1016/B978-0-12-385120-8.00018-8 (2011).
Wang, H. H. et al. Programming cells by multiplex genome engineering and accelerated evolution. Nature 460, 894-898, doi:10.1038/nature08187 (2009).
Wang, L., et al. Addition of the keto functional group to the genetic code of *Escherichia coli*. Proceedings of the National Academy of Sciences of the United States of America 100, 56-61, doi:10.1073/pnas.0234824100 (2003).
Wang, L.X. et al., Realizing the Promise of Chemical Glycobiology. Chem Sci, 2013. 4(9): p. 3381-3394.
Watanabe, M. et al. Cell-free protein synthesis for structure determination by X-ray crystallography. Methods in molecular biology 607, 149-160, doi:10.1007/978-1-60327-331-2_13 (2010).
Weerapana, E. et al., Asparagine-linked protein glycosylation: from eukaryotic to prokaryotic systems. Glycobiology, 2006. 16(6): p. 91R-101R.
Wen, K.Y., et al., A Cell-Free Biosensor for Detecting Quorum Sensing Molecules in P. aeruginosa-Infected Respiratory Samples. ACS Synthetic Biology, 2017. 6(12): p. 2293-2301.
Wetmur, J. G. "DNA probes: applications of the principles of nucleic acid hybridization." Critical reviews in biochemistry and molecular biology 26.3-4 (1991): 227-259.
Wu, I. L. et al. Multiple site-selective insertions of noncanonical amino acids into sequence-repetitive polypeptides. Chembiochem : a European journal of chemical biology 14, 968-978, doi:10.1002/cbic.201300069 (2013).
Xu, Z., et al. High-level expression of soluble human beta-defensin-2 fused with green fluorescent protein in *Escherichia coli* cell-free system. Applied biochemistry and biotechnology 127, 53-62 (2005).
Yang, W. C. et al. Cell-free production of transducible transcription factors for nuclear reprogramming. Biotechnology and bioengineering 104, 1047-1058, doi: 10.1002/bit.22517 (2009).
Young, T. S. et al. Beyond the canonical 20 amino acids: expanding the genetic lexicon. The Journal of biological chemistry 285, 11039-11044, doi:10.1074/jbc.R109.091306 (2010).
Young, T. S., et al. An enhanced system for unnatural amino acid mutagenesis in E. coli. Journal of molecular biology 395, 361-374, doi:10.1016/j.jmb.2009.10.030 (2010).
Zawada, J. et al. Effects of growth rate on cell extract performance in cell-free protein synthesis. Biotechnology and bioengineering 94, 618-624, doi:10.1002/bit.20831 (2006).
Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).

* cited by examiner

ON DEMAND, PORTABLE, CELL-FREE MOLECULAR SENSING PLATFORM

CROSS-REFERENCE TO RELATED PATENT APPLICATIONS

This application represents the U.S. national stage entry of International Application PCT/US2019/045116 filed Aug. 5, 2019, which claims the benefit of priority to U.S. Provisional Application No. 62/714,427, filed on Aug. 3, 2018, the contents of each are incorporated herein by reference in their entireties.

STATEMENT REGARDING FEDERALLY SPONSORED RESEARCH OR DEVELOPMENT

This invention was made with government support under FA8650-15-2-5518 awarded by the Department of Defense, Air Force Research Laboratory, under GM008449 awarded by the National Institutes of Health, and under HR0011-15-C-0084 awarded by the Defense Advances Research Project Agency. The government has certain rights in the invention.

BACKGROUND

The field of the invention relates to cell-free protein synthesis (CFPS) systems. In particular, the field of the invention relates to the use of CFPS systems for in vitro detection of target molecules using cellular extracts.

Cell-free protein synthesis (CFPS) using extracts from prokaryotic source strains such as E. coli has undergone a transformational shift from an exploratory platform used in the discovery of the genetic code to a present-day, high-yielding protein production platform.[1] This shift is fueled by the open nature of this system, allowing for rapid combination, supplementation, and optimization of the physiochemical environment for increasing protein yields and batch reaction duration.[2,3] Now, cell-free systems are seen as a complement to in vivo protein expression and can be used as both a prototyping platform due to their simplicity, easiness, and modular design for protein expression[4-6] as well as a large-scale production platform for difficult-to-express proteins in vivo.[7,8]

Here, we disclose a platform that utilizes CFPS for in vitro sensing of metabolites including small-molecule metabolites. The components of the platform are modular and can be preserved for long-term use.

SUMMARY

Disclosed are methods, devices, kits, components, and compositions for detecting a target molecule in a test sample using a cell-free protein synthesis (CFPS) reaction. The methods, devices, kits, components, and compositions may be utilized for detecting target molecules which may include small molecules and/or metabolites of small molecules. The components used in the disclosed methods, devices, and kits may be dried or lyophilized and may be present or immobilized on a paper substrate.

The disclosed methods may be performed to detect a target molecule in a biological or environmental sample and may include steps of: (i) obtaining a biological or environmental sample which may or may not contain the target molecule and optionally concentrating and/or solubilizing the target molecule in the sample if necessary; and (ii) adding the sample and/or the optionally concentrated and/or solubilized target molecule in the sample to a cell-free protein synthesis (CFPS) reaction, where, if the target molecule is present in the sample, then an detectable output is generated.

The disclosed devices, kits, and components thereof may be utilized in the disclosed methods. Optionally, the components of the disclosed methods, devices, and kits may be preserved, for example, by freeze-drying or lyophilization, and may be present on a substrate, such as a paper substrate used as a paper test article.

DETAILED DESCRIPTION

Figure 1:
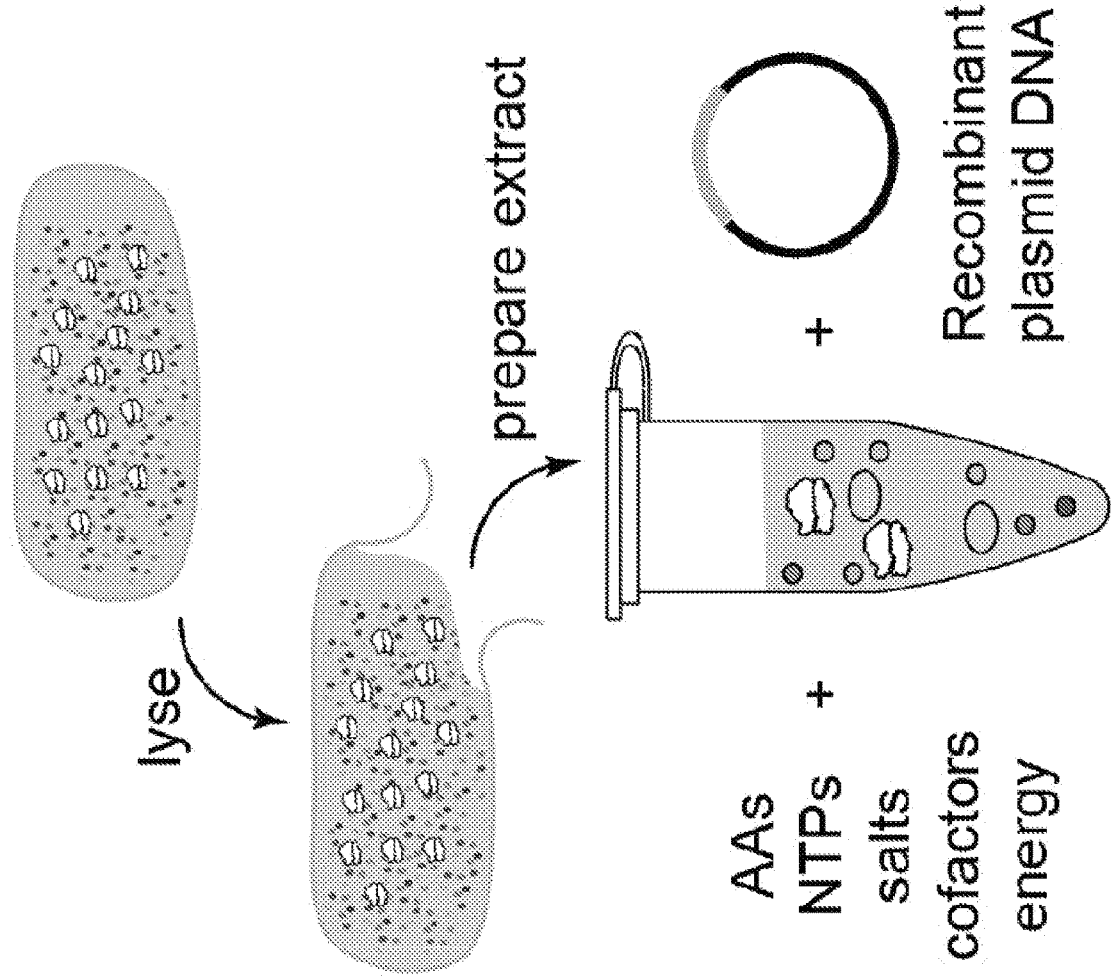
FIG. 1. Schematic illustration of components that are prepared and combined to form a cell-free protein synthesis reaction.

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "target molecule" means any molecule of interest in a test sample and may include so-called "small molecules" or metabolites of small molecules. Generally, small molecules have a molecular weight of 1 kD or less. Target molecules may be referred to herein as "analytes."

The term "metabolite" means a molecule to which a target molecule is converted, for example, by one or more components such as enzymes that are present in a cell-free protein synthesis (CFPS) reaction mixture and/or that are added to a CFPS reaction mixture The term "transcription factor" refers to a protein that regulates transcription of another protein, typically by interacting by one or more cis-acting DNA sequence in or near the promoter for the other protein. A transcription factor may increase expression or decrease expression depending upon whether the transcription factor is activated or deactivated. A transcription factor may become activated or deactivated by an interaction with another molecule (e.g., a metabolite as described above).

The term "reporter protein" refers to a protein that can be detected in a reaction mixture, such as a CFPS reaction mixture, typically in response to the presence of a target molecule or a metabolite thereof being present in the reaction mixture. For example, a reporter protein may be expressed and detected in a CFPS reaction mixture when a target molecule or a metabolite thereof activates a transcription factor which promotes expression of the reporter protein in the CFPS reaction mixture.

The term "promoter" refers to a cis-acting DNA sequence that directs RNA polymerase and other trans-acting transcription factors to initiate RNA transcription from the DNA template that includes the cis-acting DNA sequence.

As used herein, a "polymerase" refers to an enzyme that catalyzes the polymerization of nucleotides. "DNA polymerase" catalyzes the polymerization of deoxyribonucleotides. Known DNA polymerases include, for example, Pyrococcus furiosus (Pfu) DNA polymerase, E. coli DNA polymerase I, T7 DNA polymerase and Thermus aquaticus (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, bacteriophage polymerases such as, but not limited to, T3 RNA polymerase, T7 RNA polymerase, SP6 RNA polymerase and E. coli RNA polymerase, among others. The foregoing examples of RNA polymerases are also known as DNA-dependent RNA polymerase. The polymerase activity of any of the above enzymes can be determined by means well known in the art.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

Proteins, Polypeptides, and Peptides

The disclosed methods, devices, kits, and components may be utilized to synthesize proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant," "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Gln | Asp, Gln, His |
| Gly | Ala |
| His | Asn, Arg, Gln, Gln |
| Ile | Leu, Val |
| Leu | Ile, Val |
| Lys | Arg, Gln, Gln |
| Met | Leu, Ile |
| Phe | His, Met Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Polynucleotides

The disclosed methods, devices, kits, and components may utilize and/or include polynucleotides. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, $E.$ $coli$, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic host cell. The method for transformation or transfection is selected based on the type of host cell being transformed and may include, but is not limited to, bacteriophage or non-viral delivery. Methods of non-viral delivery of nucleic acids include electroporation and heat shock. The term "transformed cells" includes stably transformed cells in which the inserted DNA is capable of replication either as an autonomously replicating plasmid or as part of the host chromosome, as well as transiently transformed which express the inserted DNA or RNA for limited periods of time.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

Cell-Free Protein Synthesis (CFPS)

The disclosed subject matter relates in part to methods, devices, kits and components for cell-free protein synthesis. Cell-free protein synthesis (CFPS) is known and has been described in the art. (See, e.g., U.S. Pat. Nos. 6,548,276; 7,186,525; 8,734,856; 7,235,382; 7,273,615; 7,008,651; 6,994,986 7,312,049; 7,776,535; 7,817,794; 8,298,759; 8,715,958; 9,005,920; U.S. Publication No. 2014/0349353, U.S. Publication No. 2016/0060301, U.S. Publication No. 2018/0016612, and U.S. Publication No. 2018/0016614, the contents of which are incorporated herein by reference in their entireties). A "CFPS reaction mixture" typically contains a crude or partially-purified bacterial extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

An aspect of the invention is a platform for preparing a sequence defined protein in vitro which may be utilized for detecting a target molecule or metabolite thereof. The platform for preparing a sequence defined polymer or protein in vitro comprises a cellular extract from a host strain. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., from about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ILLUSTRATED EMBODIMENTS

The following Embodiments are illustrative and should not be interpreted to limit the scope of the claimed subject matter.

Embodiment 1. A method of detecting a target molecule in a biological or environmental sample, the method comprising: (i) obtaining a biological or environmental sample which may or may not contain the target molecule and optionally concentrating and/or solubilizing the target molecule in the sample if necessary; (ii) adding the sample and/or the optionally concentrated and/or solubilized target molecule in the sample to a cell-free protein synthesis (CFPS) reaction, wherein if the target molecule is present in the sample then an output is generated (e.g., a visual, electronic, or optical output).

Embodiment 2. The method of embodiment 1, wherein the cell-free protein synthesis reaction comprises: (a) a cell extract from a host strain that (i) provides energy; (ii) provides cofactor regeneration; (iii) provides enzymes used for cell-free sensing of the target molecule; or (iv) any combination thereof; and (b) exogenous supplied cell-free protein synthesis reagents not present in the cell extract that comprise at least one transcription template and a polymerase.

Embodiment 3. The method of embodiment 2, wherein the visual, electronic, or optical output is generated by a reporter protein that is expressed in the presence of a transcription factor or transcription system that is activated by the target molecule (e.g., a metabolite).

Embodiment 4. The method of embodiment 3, wherein the transcription factor is a single soluble protein.

Embodiment 5. The method of embodiment 3, wherein the transcription systems comprises a membrane-bound kinase and a soluble DNA-binding response regulator and the membrane-bound kinase regulates the activity of the soluble DNA-binding response regulator.

Embodiment 6. The method of embodiment 3, wherein the transcription factor and the reporter protein are synthesized via CFPS in the same pot.

Embodiment 7. The method of embodiment 3, wherein the transcription factor is synthesized in situ via CFPS in a first pot and the reporter protein is synthesized in situ via CFPS in a second pot to which the first pot comprising the transcription factor is added.

Embodiment 8. The method of embodiment 3, wherein the transcription factor is overexpressed in the host strain to enrich it in the cell extract used for the CFPS reaction.

Embodiment 9. The method of embodiment 3, wherein the transcription factor is overexpressed in the host strain prior to making the cell extract for the CFPS reaction, and the transcription factor-enriched extract is added to a blank extract that is not enriched for any specific protein to yield a final extract for the CFPS reaction of the reporter protein.

Embodiment 10. The method of embodiment 3, wherein the transcription factor is separately expressed from cells and purified, and the purified transcription factor is then mixed directly into the CFPS reaction.

Embodiment 11. The method of embodiment 2, wherein the visual, electronic, or optical output is generated from an enzymatic reaction catalyzed by the target molecule.

Embodiment 12. The method of embodiment 2, wherein the visual, electronic, or optical output is generated from an enzymatic reaction catalyzed by a metabolite of the target molecule that is generated in the CFPS reaction.

Embodiment 13. The method of any of embodiments 5-10, wherein the transcription factor is activated by a metabolite of the target molecule that is generated in the CFPS reaction.

Embodiment 14. The method of embodiment 12, wherein the cell extract for the CFPS reaction is enriched in one or more enzymes that generate the metabolite of the target molecule, optionally wherein the host cell overexpresses the one or more enzymes that generate the metabolite of the target molecule.

Embodiment 15. The method of embodiment 13, wherein the cell extract for the CFPS reaction is enriched in one or more enzymes that generate the metabolite of the target molecule, optionally wherein the host cell overexpresses the one or more enzymes that generate the metabolite of the target molecule.

Embodiment 16. The method of embodiment 12 or 13, wherein one or more metabolic enzymes necessary for the metabolite from the target molecule are overexpressed in the host strain prior to making the cell extract for the CFPS reaction.

Embodiment 17. The method of embodiment 12 or 13, wherein two or more metabolic enzymes necessary for generating the metabolite from the target molecule are overexpressed in two or more different host strains individually or in groups and the cell extract for the CFPS reaction is prepared by combining cell extracts from the two or more different host strains.

Embodiment 18. The method of embodiment 12 or 13, wherein one or more metabolic enzymes necessary for generating the metabolite from the target molecule are expressed in the CFPS reaction.

Embodiment 19. The method of embodiment 12 or 13, wherein one or more metabolic enzymes necessary for the metabolite from the target molecule are overexpressed in the host strain prior to making the cell extract for the CFPS reaction and wherein one or more metabolic enzymes necessary for generating the metabolite from the target molecule are expressed in the CFPS reaction.

Embodiment 20. The method of embodiment 12 or 13, wherein one or more metabolic enzymes necessary for generating the metabolite from the target molecule are expressed via CFPS reaction in a first pot; wherein the reporter protein is synthesized via CFPS in a second pot; and wherein the method further comprises adding the contents of the first pot and to second pot prior to synthesis of the reporter protein.

Embodiment 21. The method of embodiment 12 or 13, wherein two or more metabolic enzymes necessary for generating the metabolite from the target molecule are synthesized in two or more different CFPS reactions in two or more different pots individually or in groups and the two or more different pots are combined to provide a synthesis pot in which the reporter protein is synthesized.

Embodiment 22. The method of embodiment 12 or 13, where one or more metabolic enzymes necessary for generating the metabolite from the target molecule are separately expressed in cells and purified, and the one or more purified metabolic enzymes are added directly to the CFPS reaction.

Embodiment 23. The method of any of embodiments 12-22, wherein level of the one or more metabolic enzymes for generating the metabolite from the target molecule are adjusted to enhance conversion of the target molecule to the metabolite.

Embodiment 24. The method of any of embodiments 1-23, wherein the biological sample is selected from the group consisting of blood, serum, urine, saliva, tissue, cell, and organ from human, animal or plant, an environmental sample, or any fraction or portion thereof.

Embodiment 25. The method of any of embodiments 1-24, wherein the output generated in the method is optical output.

Embodiment 26. The method of embodiment 25, where the optical output is luminescence, fluorescence, or visible color.

Embodiment 27. The method of any of embodiments 1-26, wherein the target molecule is cyanuric acid.

Embodiment 28. The method of any of embodiments 1-26, wherein the target molecule is atrazine.

Embodiment 29. The method of any of embodiments 1-26, wherein the target molecule is nitrate.

Embodiment 30. A device or kit comprising components for detecting a target molecule according to any of embodiments 1-29, wherein the components comprise preserved CFPS reaction components.

Embodiment 31. The device or kit of embodiment 30, wherein the preserved CFPS reaction components are preserved by freeze-drying.

Embodiment 32. The device or kit of embodiment 30 or 31 further comprising a component for reading an electronic, optical, or fluorescent output.

Embodiment 33. The device or kit of any of embodiments 30-32, wherein the preserved CFPS reaction components are supported on a substrate which optionally is a paper substrate (e.g., a paper test article).

Embodiment 34. The device or kit of embodiment 33, wherein the support (optionally the paper support such as a paper test article) comprises components that are preserved by freeze-drying.

Embodiment 35. The device or kit of embodiment 33 or 34, further comprising a component for reading an electronic, optical, or fluorescent output.

EXAMPLES

The following Examples are illustrative and are not intended to limit the scope of the claimed subject matter.

Example 1

In Vitro Biosensing of Small-Molecule Metabolites in Cellular Extracts

Abstract

Disclosed are cell-free systems for molecular sensing based on direct enzymatic conversion or responsive transcription factors, methods for using metabolism and combinatorial pathway assembly to convert target molecules into responsive molecules, kits for preparing the disclosed systems, and kits for performing the disclosed methods. The disclosed systems, methods, and kits may be utilized for sensing. Methods specific for detecting and identifying the presence of phloroglucinol and atrazine are provided.

Applications

Applications of the disclosed technology include, but are not limited to: ((i) On-demand biosensing of molecules in enriched bacterial extracts using fluorescent and colorimetric reporters; (ii) Metabolic bioconversion of target metabolites in vitro into compounds that can be directly sensed using transcriptional biosensors; (iii) Lyophilization and reconstitution of these biosensors and/or immobilization on a fibrous substrate; (iv) Real-time detection of toxins and/or contaminants in biological or environmental samples; (v) High-throughput screening of strains for metabolic engineering; and (vi) Point-of-care diagnostics in biological samples.

Advantages

Advantages of the disclosed technology include, but are not limited to: (i) Faster, more portable, and less expensive than existing chemical, electrochemical, or analytical processes for detecting environmental contaminants or other analytes of interest; (ii) Enables rapid visible detection of target molecules over background using fluorescent or colorimetric measurement; and (iii) Compared to whole-cell biosensors, little-to-no concern for biocontainment or regulations on transgenic organisms, issues with ligand permeability or degradation inside cells, or cytotoxicity.

Description of Technology

This invention constitutes the sensing of molecules in a bacterial extract-based cell-free protein synthesis reaction with a fluorescent or colorimetric reporter readout. In the basic case, this sensing is accomplished through the coordinated activity of a known metabolite transcription factor responding to its target ligand to regulate expression of a fluorescent or colorimetric reporter. Metabolites to be sensed may be first chemically converted to metabolites with known biosensing transcription factors through an enzymatic pathway that is reconstituted in vitro. In another variant of the invention, the sensed metabolite may be directly converted through a reconstituted metabolic pathway to a target molecule that then serves as the substrate for an enzymatic reaction with a visible, optical, or electronic signal. In each case, both the transcription factor biosensor and the metabolic pathway enzymes can be enriched in the cell-free protein synthesis reaction through some combination of: protein synthesis and purification from cells in a separate batch culture, in situ coordinated expression of the individual proteins in the same pot, expression of the individual proteins in separate pots and mixed into the final, or overexpression of the proteins in the source strain used to make the extract. The full reaction can be freeze-dried and reconstituted with the liquid sample either in tubes, plates, or immobilized on a paper substrate.

Example 2

Cell-Free Transcription-Translation Systems as Sensors for Metabolites

Metabolic limits constrain the use of cells as chemical factories or sensors. First, engineering cells for use as chemical factories or sensors is challenging. Cells contain burdensome metabolic circuits which are genetically unstably. In addition, secondary interactions between components of metabolic circuits can be difficult to predict and the time to design, build, and test cells as chemical factories or sensors is relatively long.

In comparison to cells, cell-free transcription-translation systems offer advantages as sensors for a number of reasons. First, toxicity that may be observed in cells due to enzyme and/or product overexpression is not an issue in cell-free systems. Cell-free systems can be more quickly prototyped and screened as sensors. Finally, the open reaction environment of cell-free systems can be more easily and finely tuned regarding optimal reagent concentrations and are more suitable for modular experimental designs. FIG. 1 illustrates the components used in cell-free systems. As such, cell-free systems are advantageous for prototyping strains and components, metabolic engineering, biosensing, and studying non-standard amino acid chemistry, glycosylation, and materials design.

Figure 2:
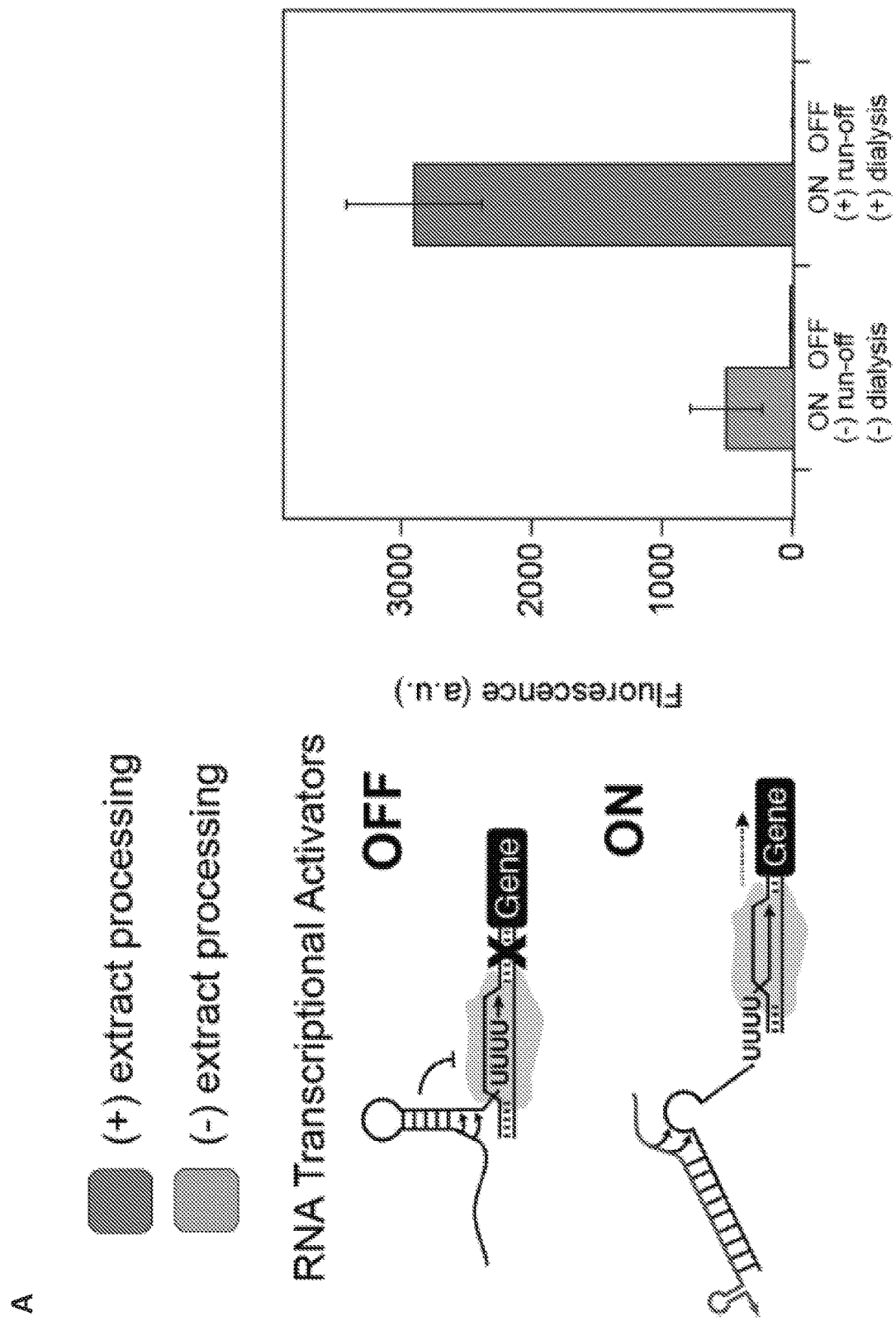
FIG. 2. Performance of additional processed extracts in six (6) different classes of sensors that utilize (A) RNA transcriptional activators, (B) RNA transcriptional repressors, (C) protein transcription factors, (D) CRISPR-Cas9 repression, (E) RNA translation activators, and (F) translational riboswitches. The use of additionally purified extracts improved ON reporter yield by at least 3×-fold and maintained a dynamic range for the six (6) different classes of sensors.
Figure 2:
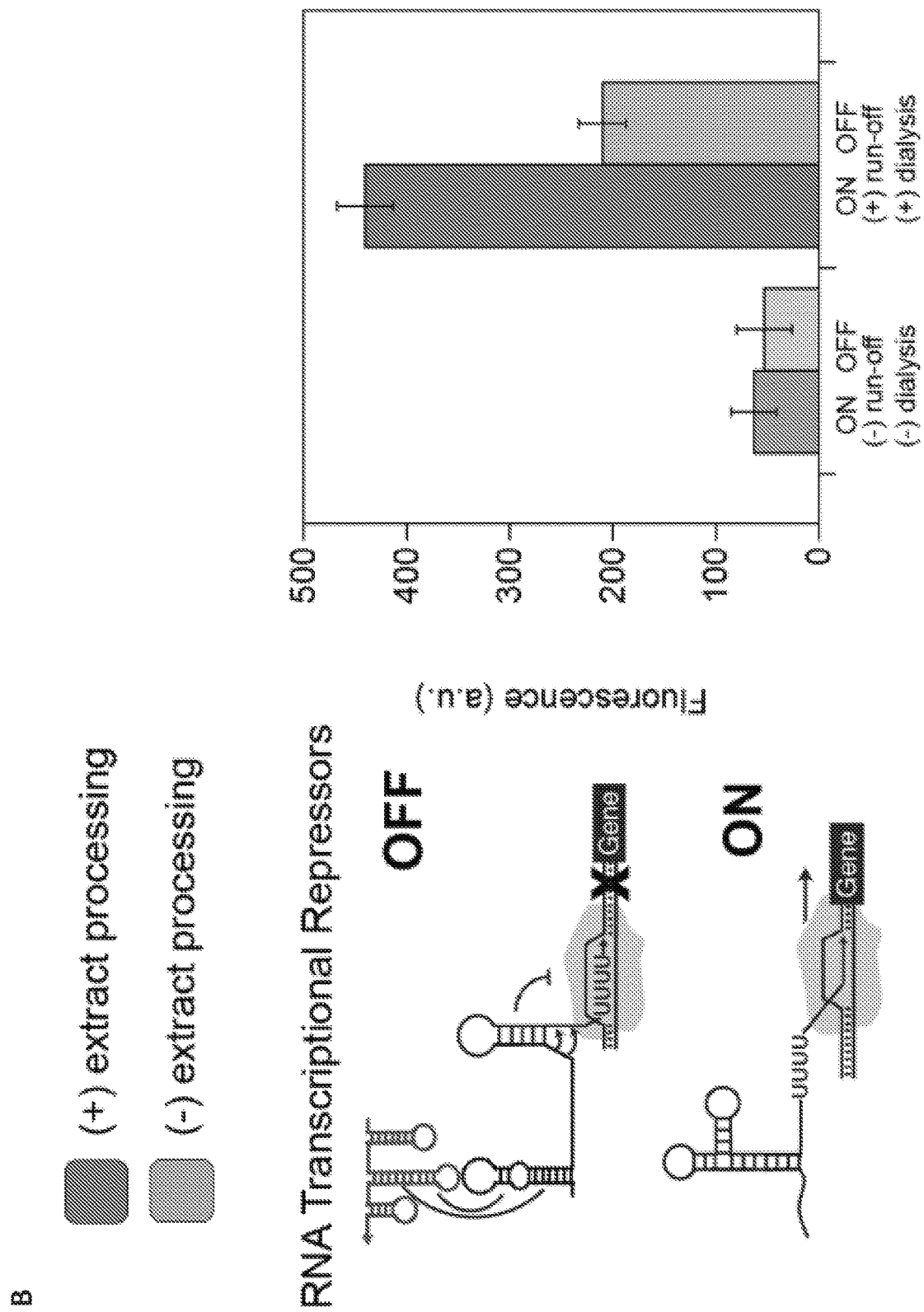
Figure 2:
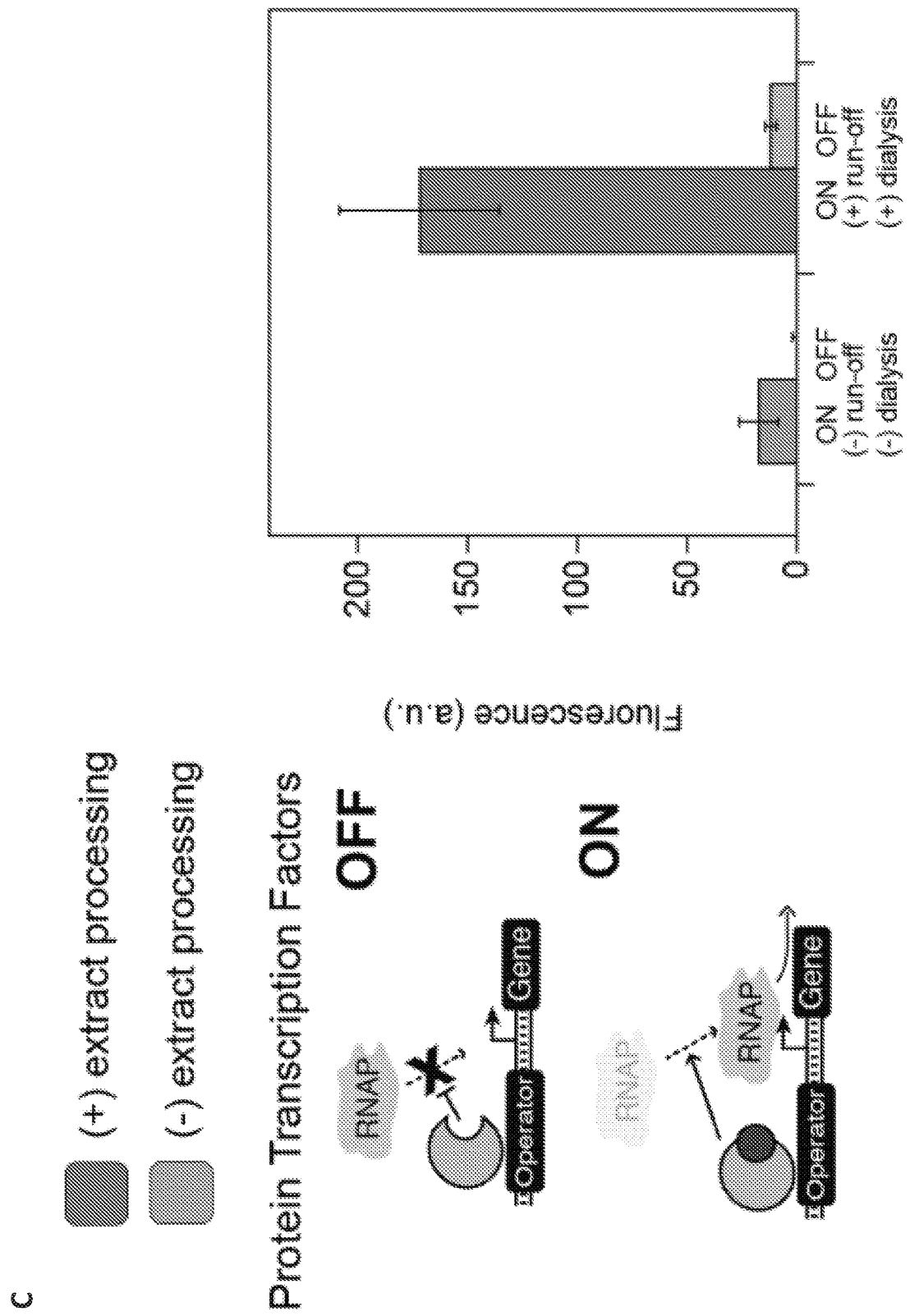
Figure 2:
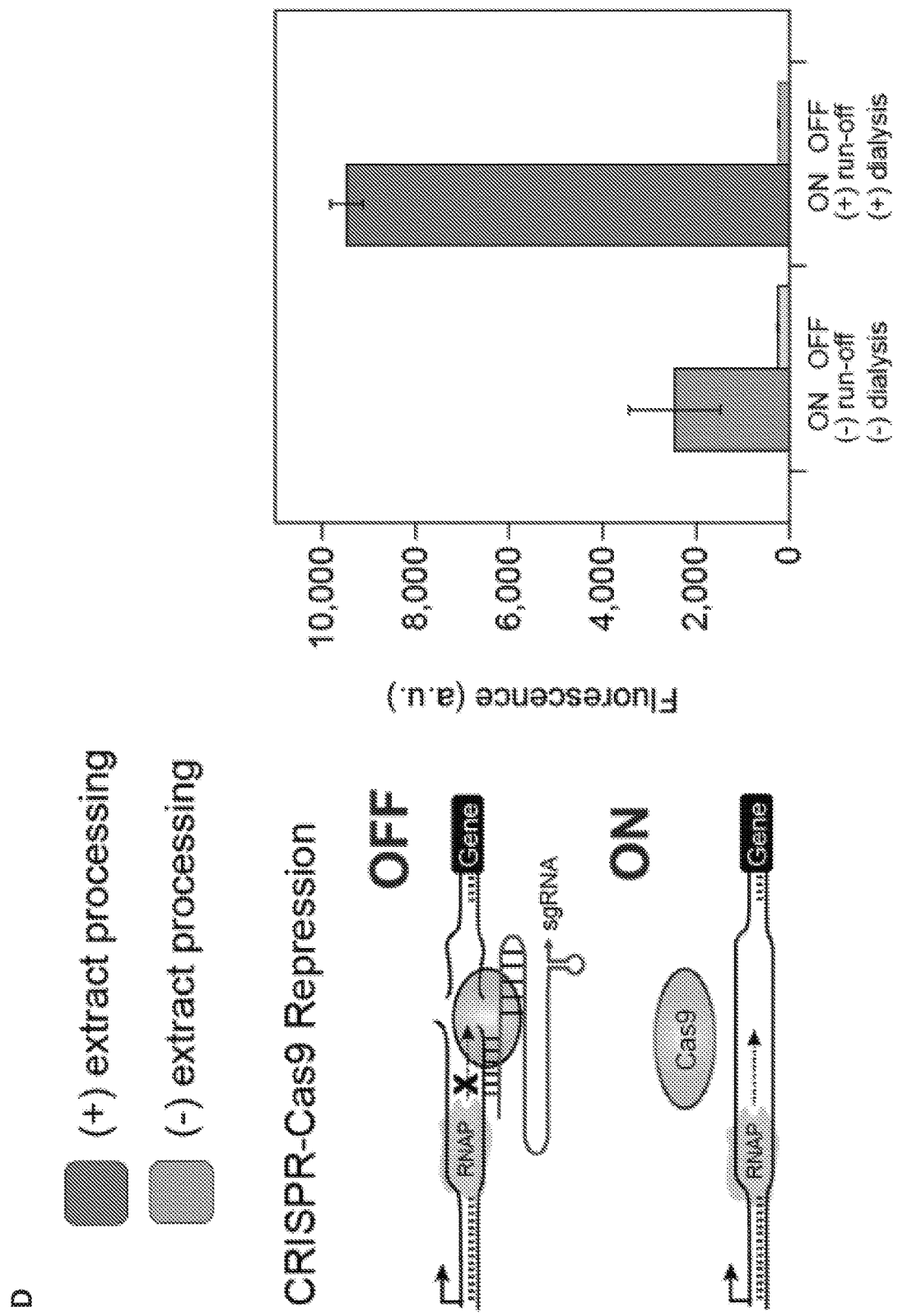
Figure 2:
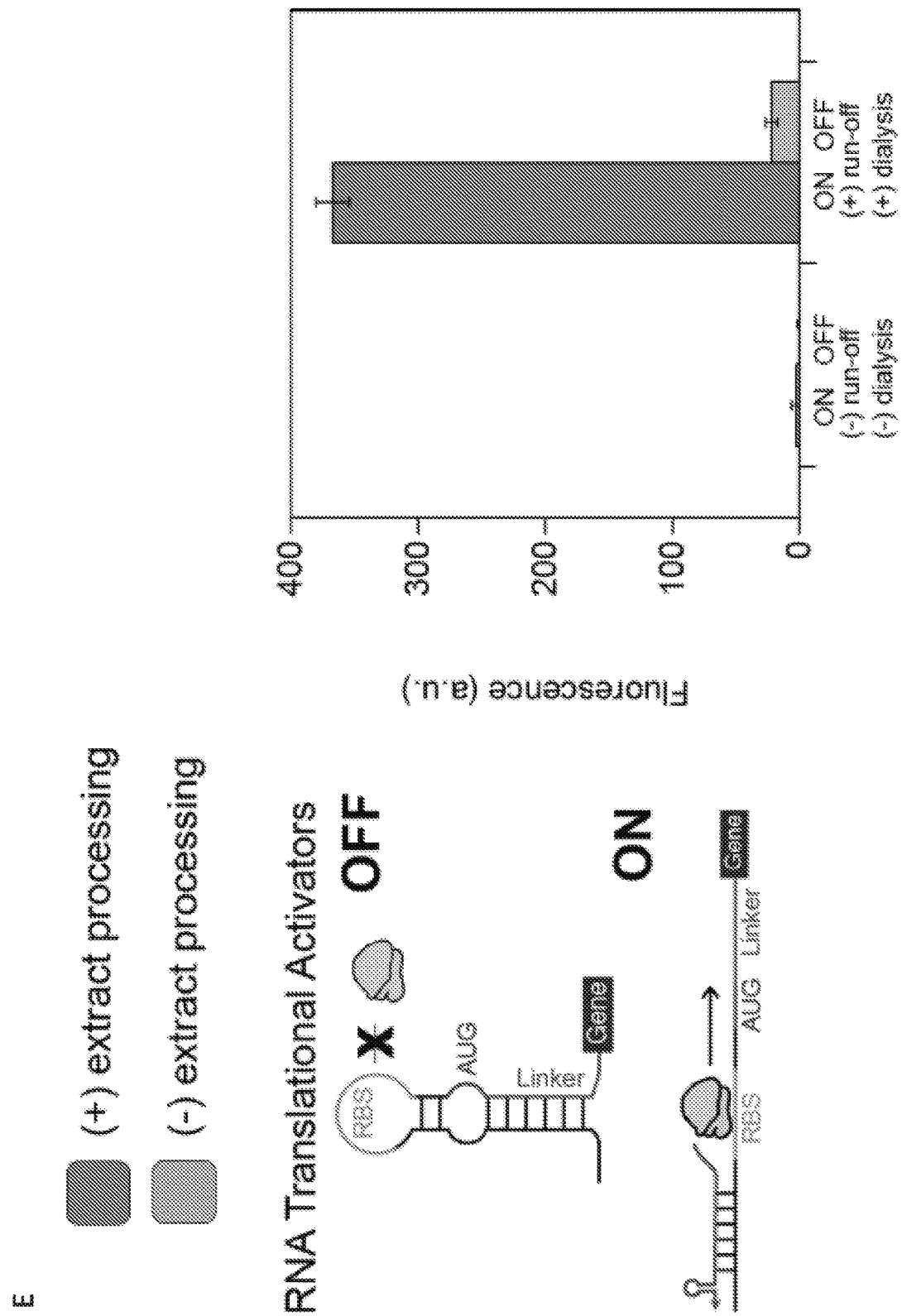
Figure 2:
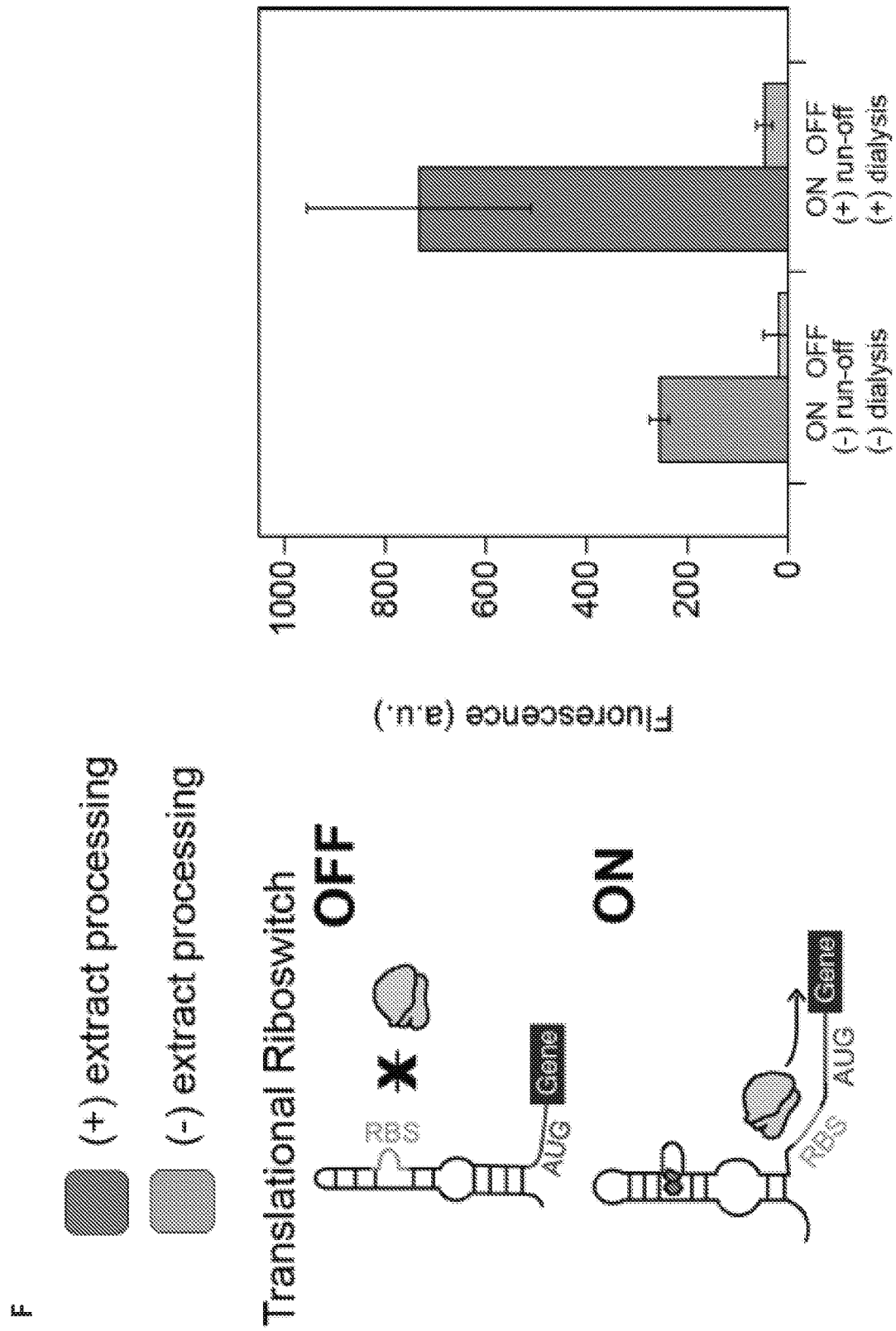

Accordingly, we have developed improved protocols for preparing and additional processing of extracts for use in cell-free protein synthesis which enabled diverse sensing modalities in vitro. The improved performance of our additionally processed extracts in six (6) different classes of sensors that utilize (1) RNA transcriptional activators, (2) RNA transcriptional repressors, (3) protein transcription factors, (4) CRISPR-Cas9 repression, (5) RNA translation activators, and (6) translational riboswitches is illustrated in FIG. 2. We observed that our additional extract purification steps improved ON reporter yield by at least 3×-fold and maintained a dynamic range for the six (6) different classes of sensors.

Figure 3:
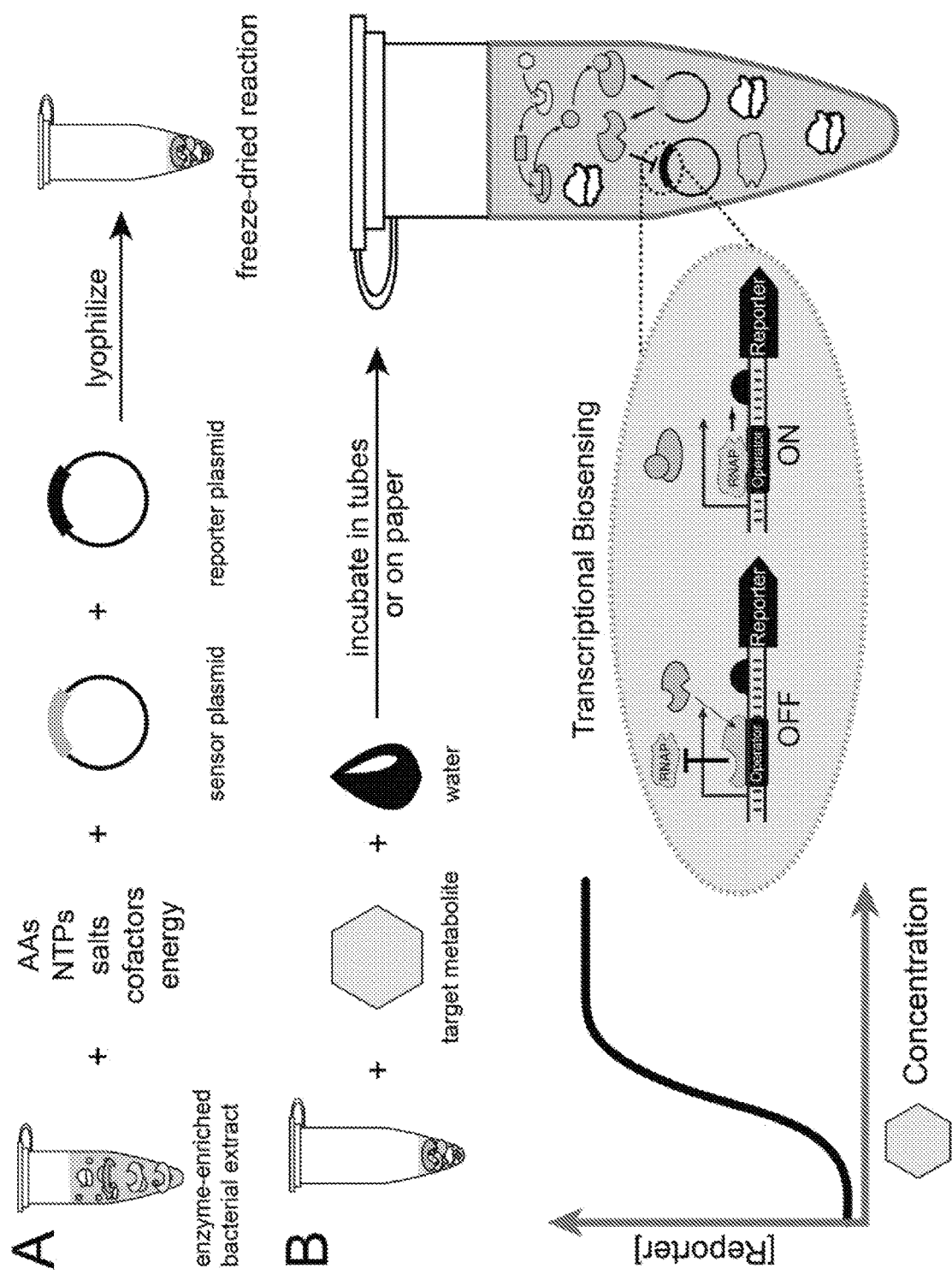
FIG. 3. Schematic of cell-free transcription factor-based biosensor. (A) Preparation of cell-free protein synthesis reaction involves combination of a bacterial extract, transcription-translation reagents, plasmid sequences encoding repressor and reporter biosynthesis in vitro, and metabolic enzymes that can convert the target metabolite (hexagon) to the metabolite sensed by the transcriptional regulator (circle). Reaction can be freeze-dried and spotted onto a fibrous support (e.g., paper) to enable thermal stability and portability. (B) Reconstitution of the freeze-dried cell-free reaction in water enables rapid sensing of the target compound over the course of a few hours.

FIG. 3 provides a general schematic of the claimed cell-free transcription factor-based biosensor. Preparation of the cell-free protein synthesis reaction involves the combination of a bacterial extract, transcription-translation reagents, plasmid sequences encoding a repressor and reporter for biosynthesis in vitro, and any metabolic enzymes that can convert the target analyte to a metabolite that is sensed by a transcriptional regulator. The combined reaction components can be freeze-dried and spotted onto a fibrous support (e.g., paper) to enable thermal stability and portability. Reconstitution of the freeze-dried cell-free reaction in water enables rapid sensing of the target compound over the course of a few hours.

Figure 4:
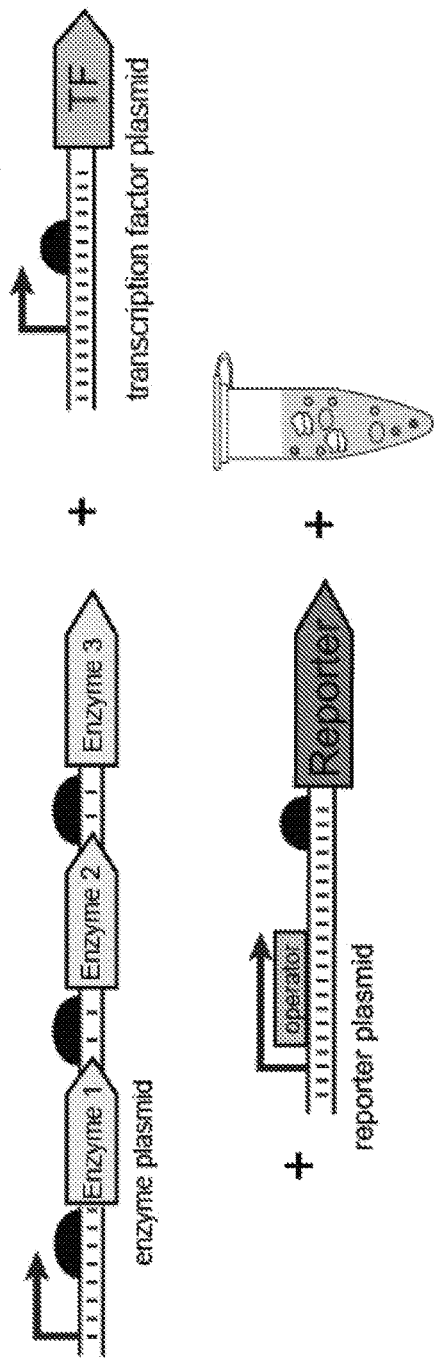
FIG. 4. Schematic for expression of metabolic enzymes and transcription factors. (A) Enzymes and transcription factors can be synthesized in situ simultaneously in the same pot as the reporter from three separate genetic constructs. (B) Enzymes and transcription factors can be synthesized in vitro in separate pots, then the spent cell-free protein synthesis reactions can be mixed in as the source of enzymes and transcription factors in a fresh sensing reaction. (C) Extracts can be enriched in the enzymes and transcription factors by overexpressing those proteins in vivo in the strain used to harvest extract and then mixing the extracts together. Any combination of these approaches, as well as supplementing proteins purified exogenously from a batch culture, could be used for each protein necessary to sense a given metabolite.
Figure 4:
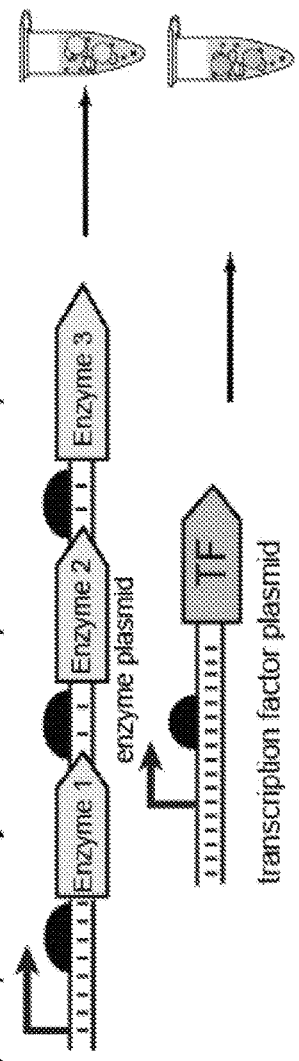
Figure 4:
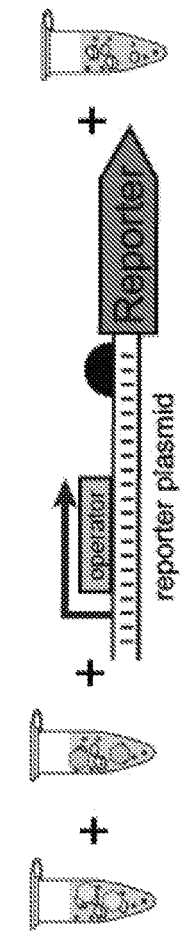
Figure 4:
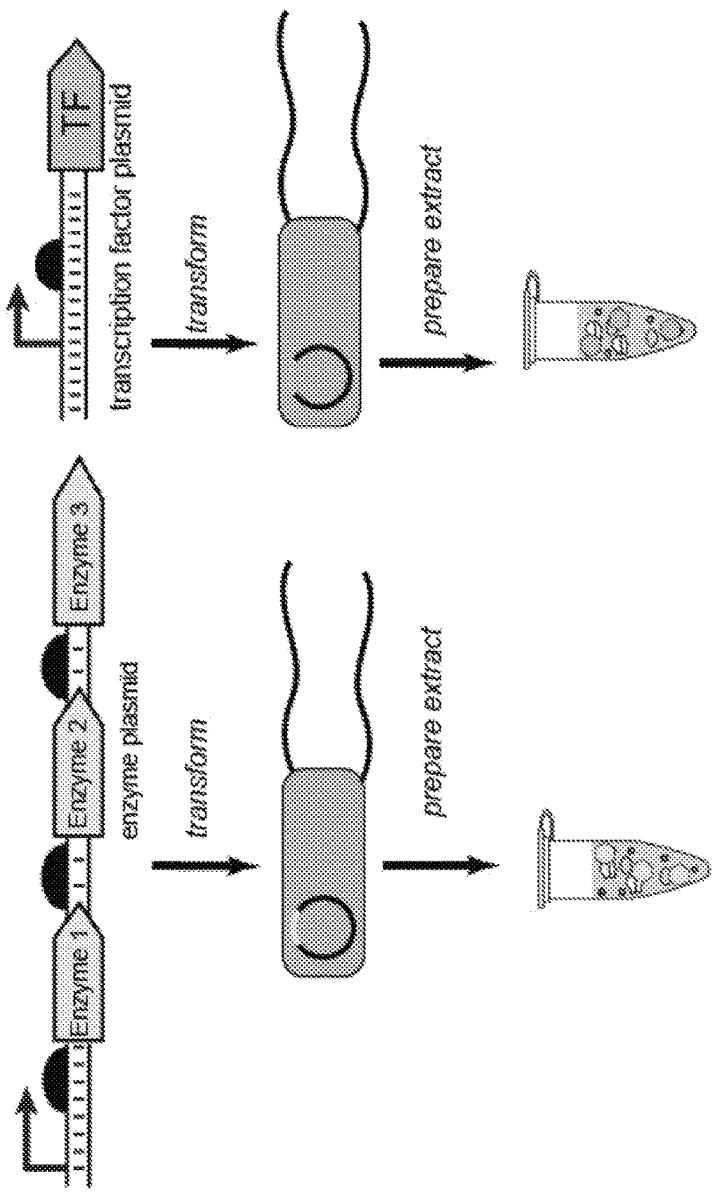
Figure 4:
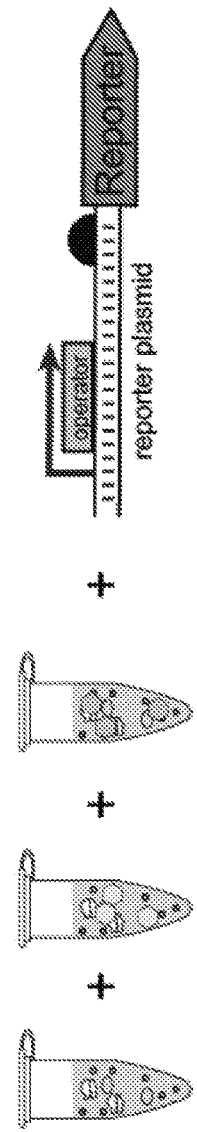

FIG. 4 provides a more specific schematic for expression of metabolic enzymes and transcription factors for a cell-free transcription factor-based biosensor. The metabolic enzymes and transcription factors can be synthesized in situ simultaneously in the same pot as the reporter from three separate genetic constructs. Alternatively, enzymes and transcription factors can be synthesized in vitro in separate pots, then the spent cell-free protein synthesis reactions can be mixed in as the source of enzymes and transcription factors in a fresh sensing reaction. Optionally, extracts can be enriched in the enzymes and transcription factors by overexpressing those proteins in vivo in the strain used to harvest extract and then mixing the extracts together. Any combination of these approaches, as well as supplementing proteins purified exogenously from a batch culture, could be used for each protein necessary to sense a given metabolite.

Figure 5:
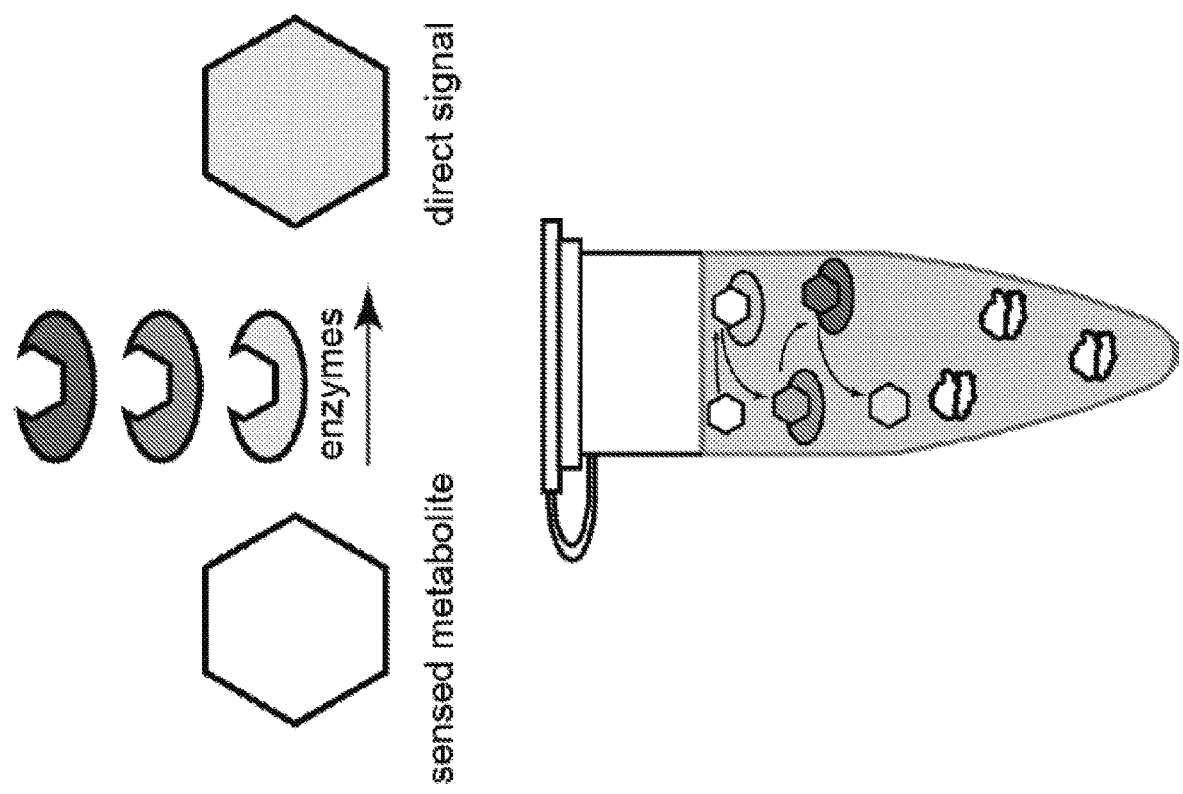
FIG. 5. Schematic for direct readout of reporter signal. If the sensed metabolite can be directly converted to a product with a visible, optical, or electronic signal, then the extract need only be enriched with the requisite metabolic enzymes (using the methods of FIG. 4) with no transcription factor necessary.

FIG. 5 provides a schematic for the direct readout of a reporter signal from a cell-free biosensor. If the sensed analyte is directly converted to a metabolite with a visible, optical, or electronic signal, then the extract need only be enriched with the requisite metabolic enzymes with no transcription factor being necessary.

Example 3

In Vitro Biosensing of Phloroglucinol Metabolites in Cellular Extracts

Phloroglucinol (PG), or 1,3,5-benzenetriol, is a small molecule precursor to various explosives and pharmaceuticals. It is naturally metabolized through a three-enzyme pathway in *Pseudomonas fluorescens* to diacetylphloroglucinol (DAPG). In *Pseudomonas*, it is naturally made through condensation of three molecules of malonyl-CoA.

Our approach was to deploy an *E. coli* extract-based sensing platform for the detection of phloroglucinol with the aim of increasing the throughput of metabolic engineering efforts on the synthetic pathway. This sensor could be used as a screening platform to rapidly identify productive strains rather than more time-consuming procedures like GC-MS. Compared to whole-cell bacterial biosensors, in vitro sensors provide superior thermal stability and portability, better tolerance to toxic ligands, and faster response.

Figure 6:
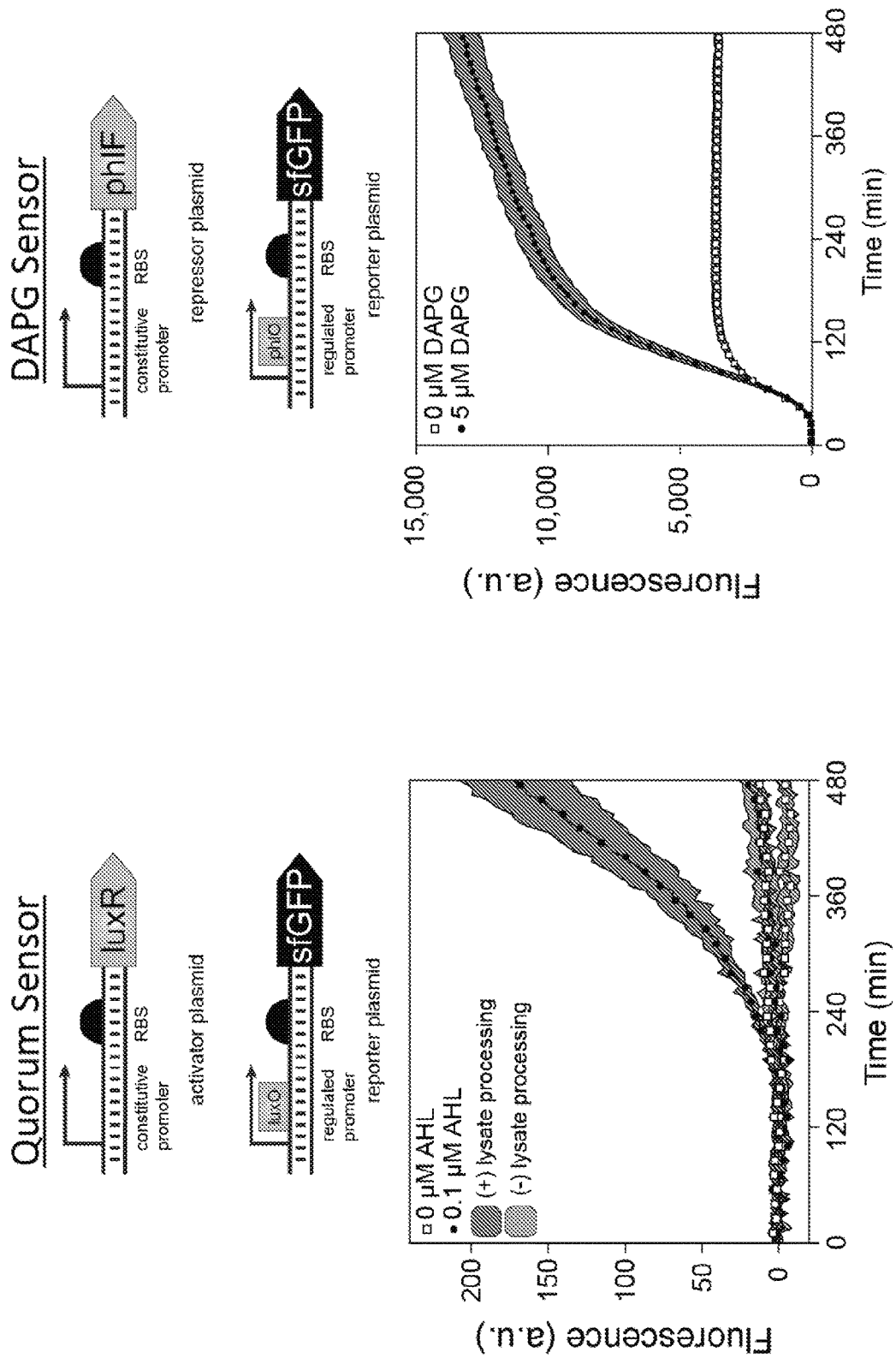
FIG. 6. Schematic representation of a Quorum Sensor and DAPG Sensor and the use of phlF to detect DAPG.

There is no known biosensor for phloroglucinol. Therefore, we worked to engineer a combined metabolism-sensing platform in which the PG is enzymatically converted to DAPG, and then the DAPG concentration can be measured through readout of a fluorescent reporter through a transcriptional actuator. We first re-engineered a cellular DAPG sensor to show functional switching activity in cell-free protein synthesis (CFPS) reactions, comparable to what can be achieved with model transcription factors in vitro (See FIG. 6). We then reconstituted the phlABC enzymatic pathway in vitro to convert the target metabolite, PG, into one that we could sense, DAPG. Our final aim was to design a one-pot sensor with robust ON state that could then be freeze-dried and deployed for paper-based sensing.

Figure 7:
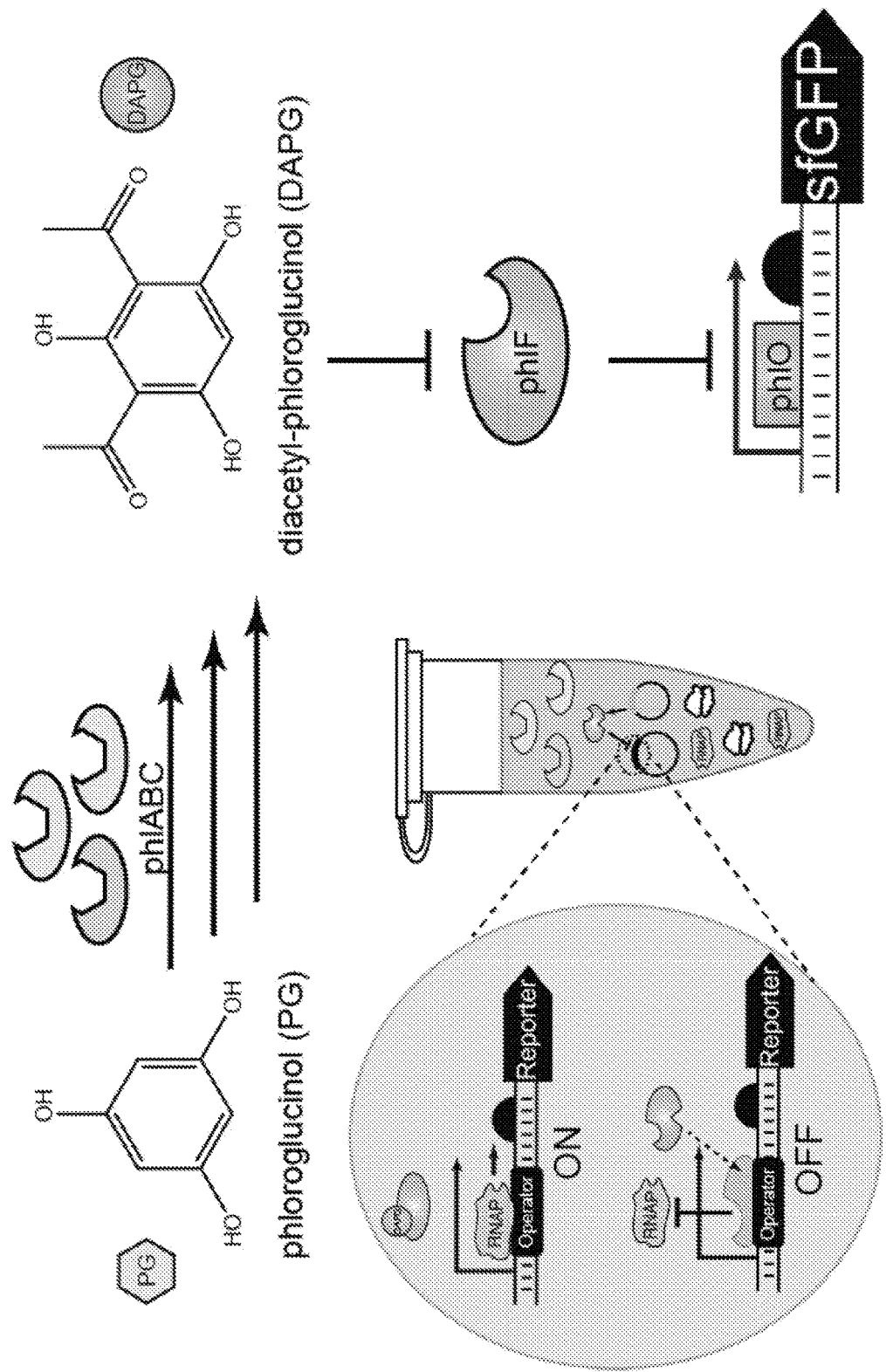
FIG. 7. Conversion of phloroglucinol (PG) via phlABC to diacetyl-phloroglucinol (DAPG) and use of DAPG to bind to repressor phlF and de-repressor promoter comprising a phlO operator to express reporter protein (sfGFP).
Figure 8:
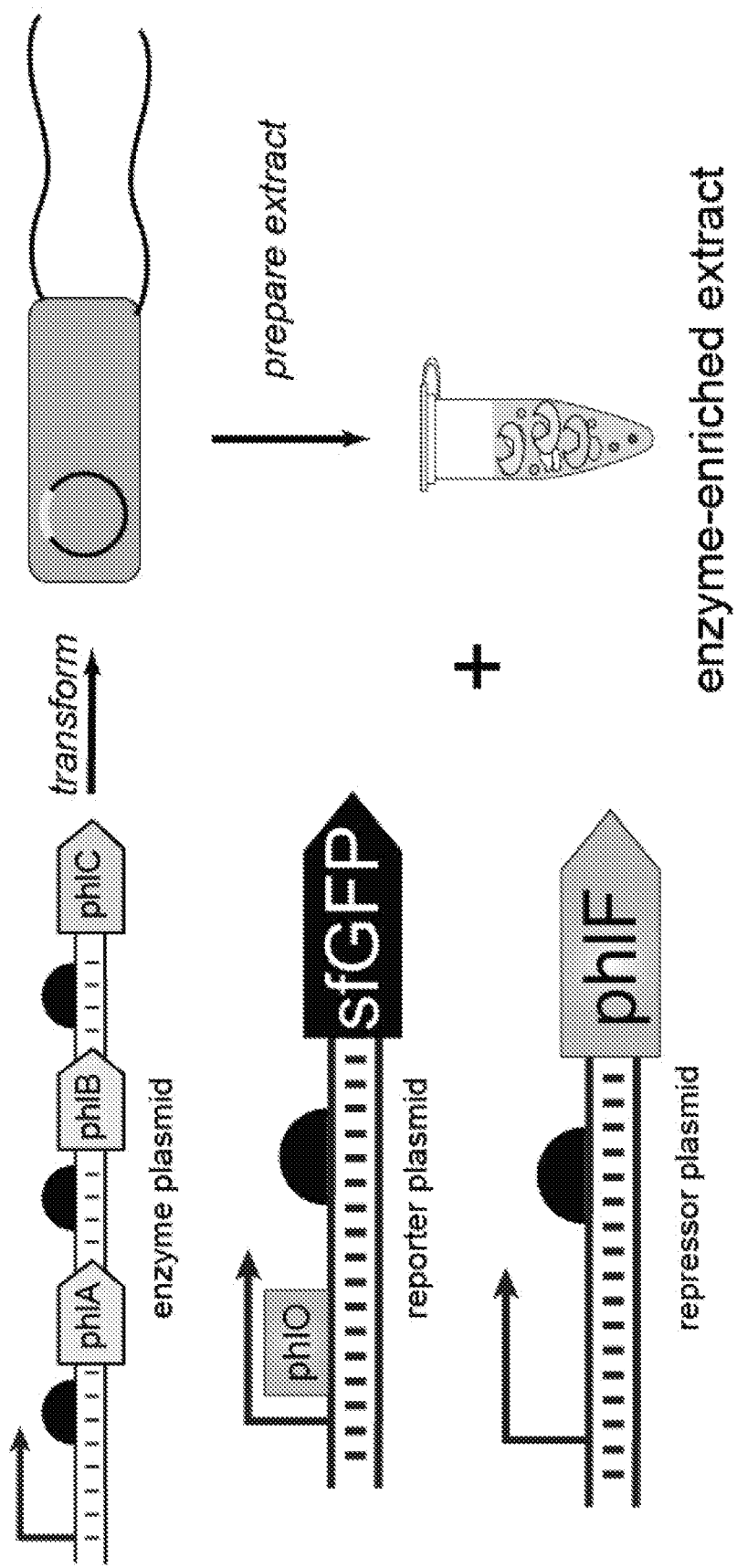
FIG. 8. Schematic illustration of preparation and use of extract enriched in metabolic enzymes phlA, phlB, and phlC.
Figure 9:
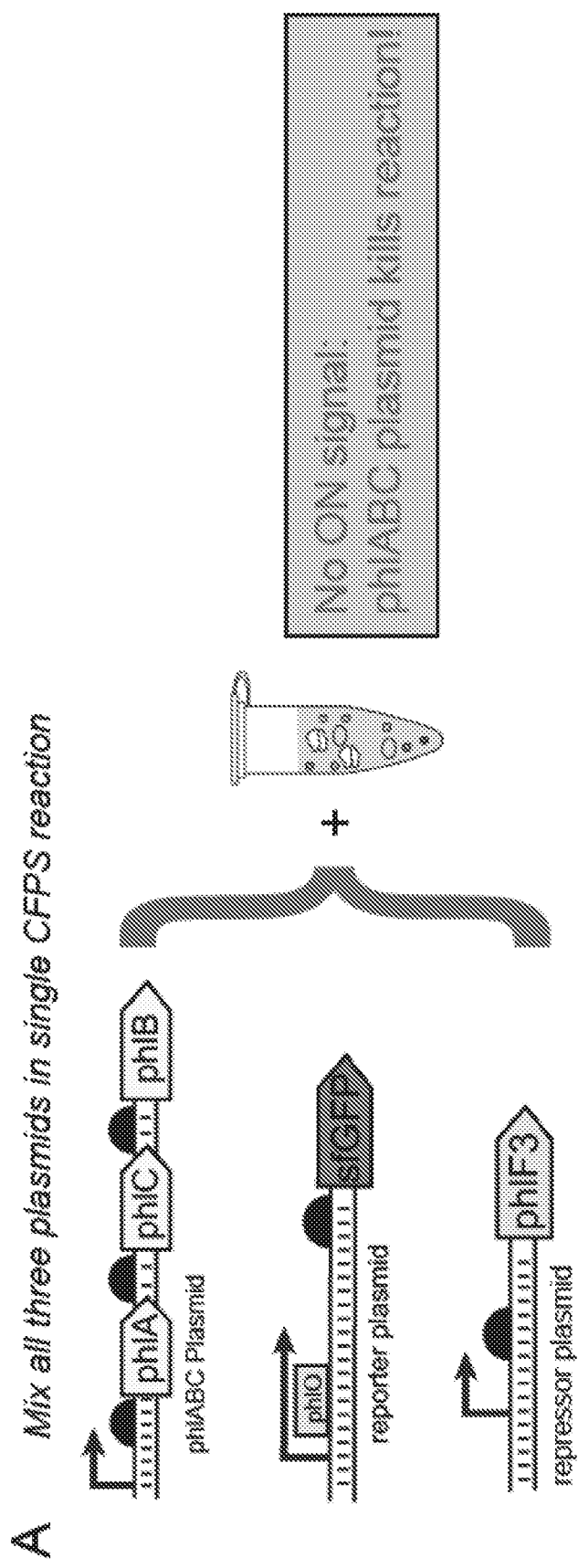
FIG. 9. Methods of converting PG to DAPG in CFPS. In (A), a three-plasmid, one-pot system is illustrated. In (B), a three-plasmid, three-pot system is illustrated. In (C), a two-plasmid, one-pot system is illustrated.
Figure 9:
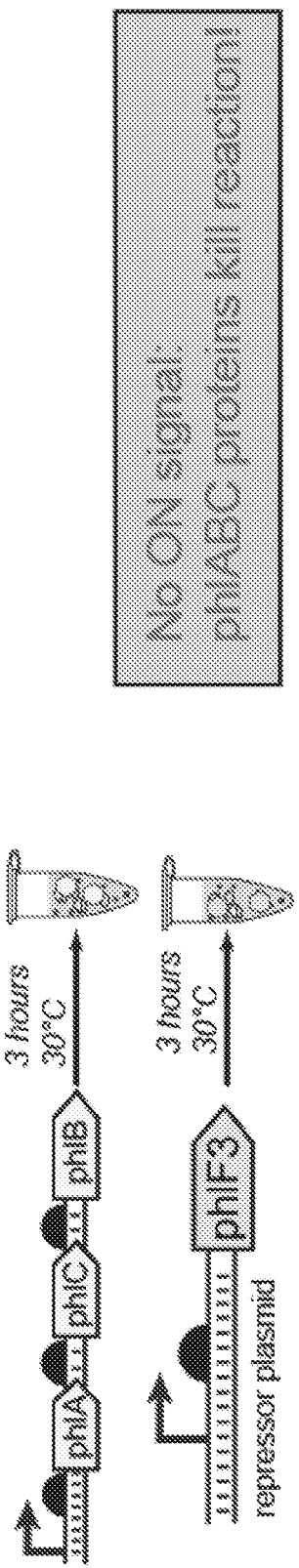
Figure 9:
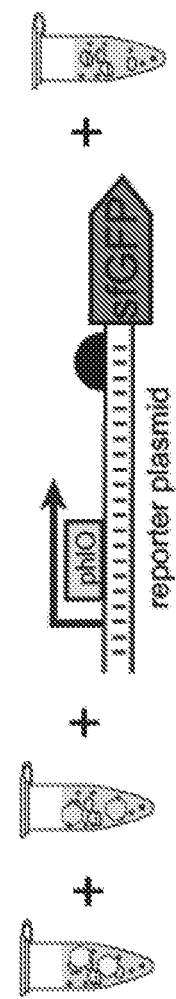
Figure 9:
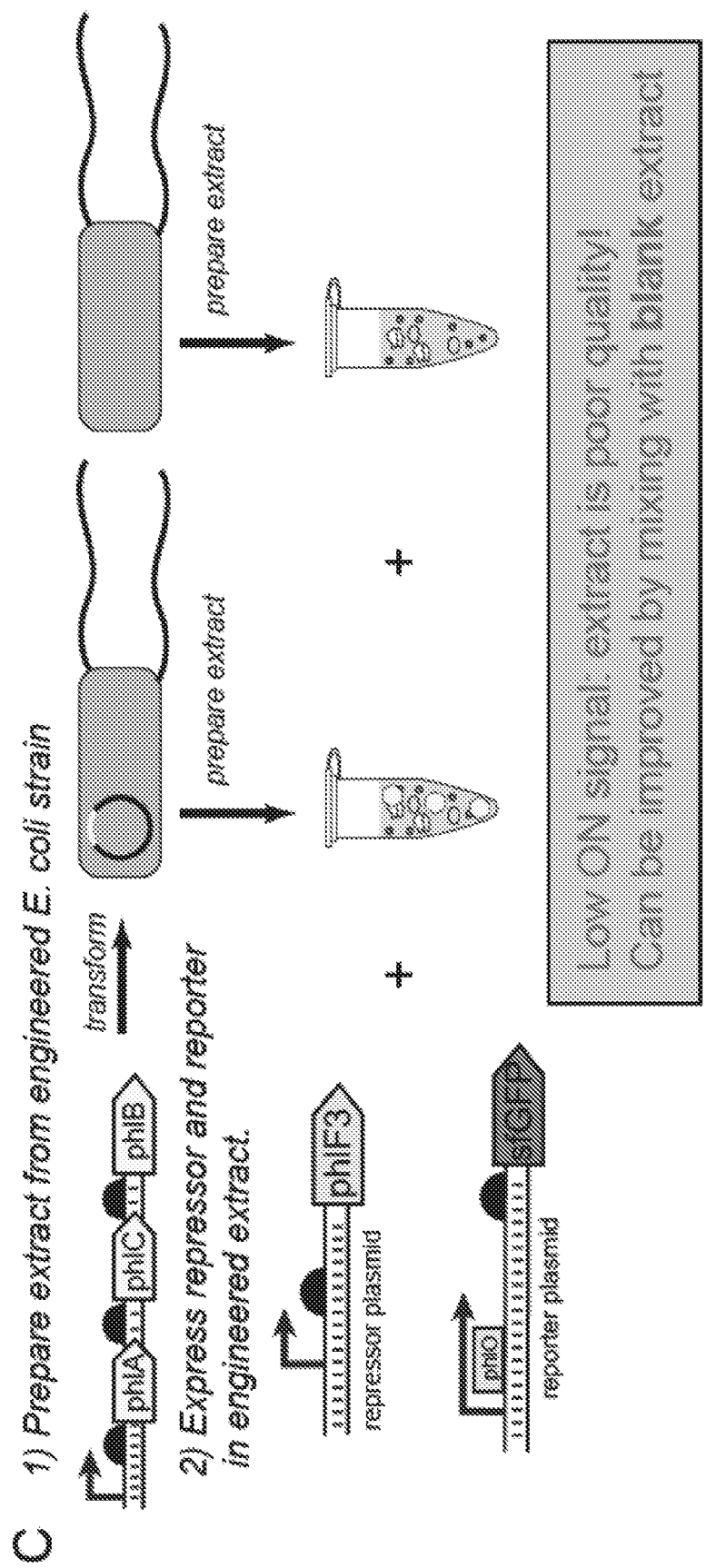
Figure 10:
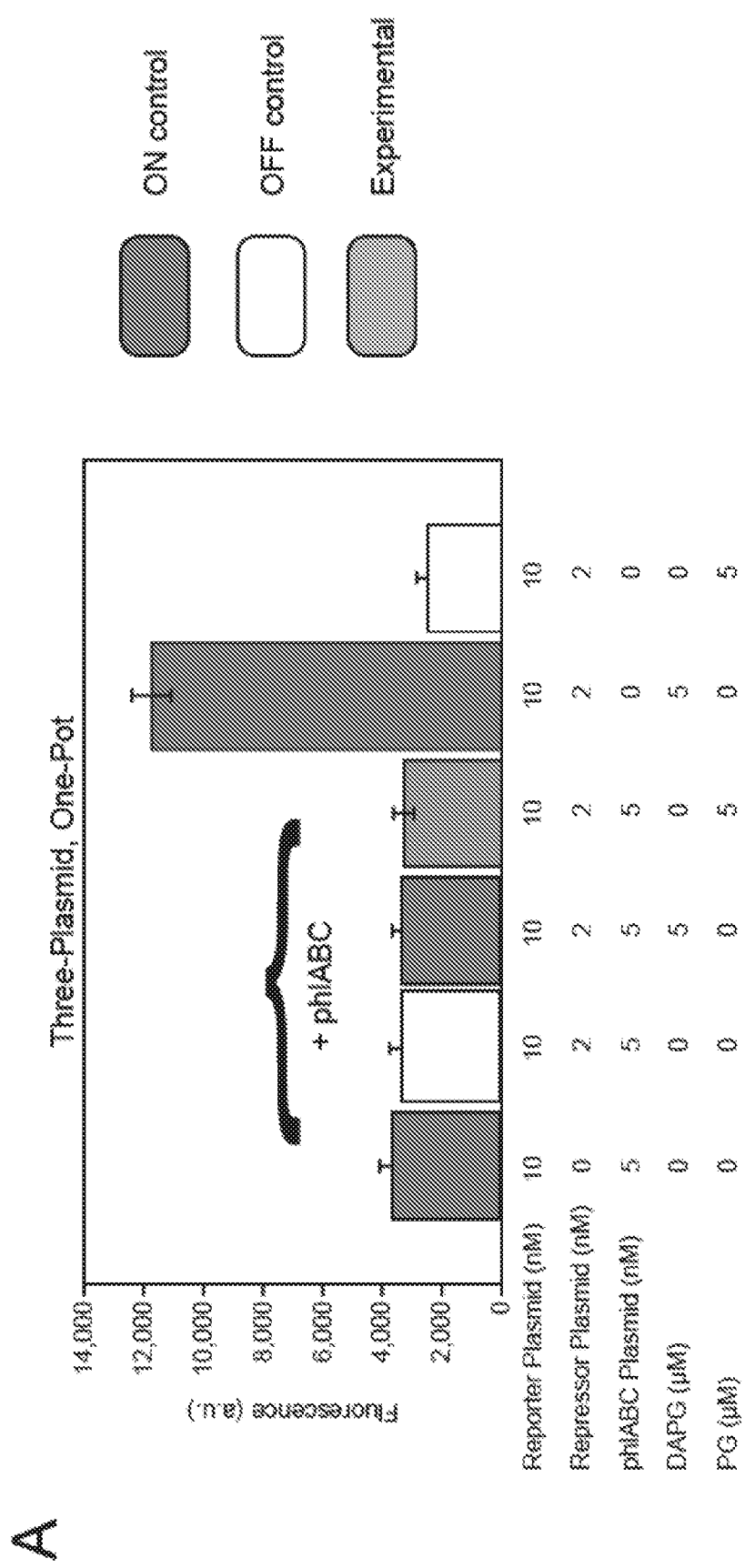
FIG. 10. Poisoning of cell-free protein synthesis reaction by phlABC. (A) Addition of phlABC plasmid poisons sensor ON state regardless of the presence of repressor, PG, or DAPG. (B) Addition of phlABC reaction product in separate pot poisons sensor ON state slightly less, but gives only slight improvement of sensor activity relative to the background.
Figure 10:
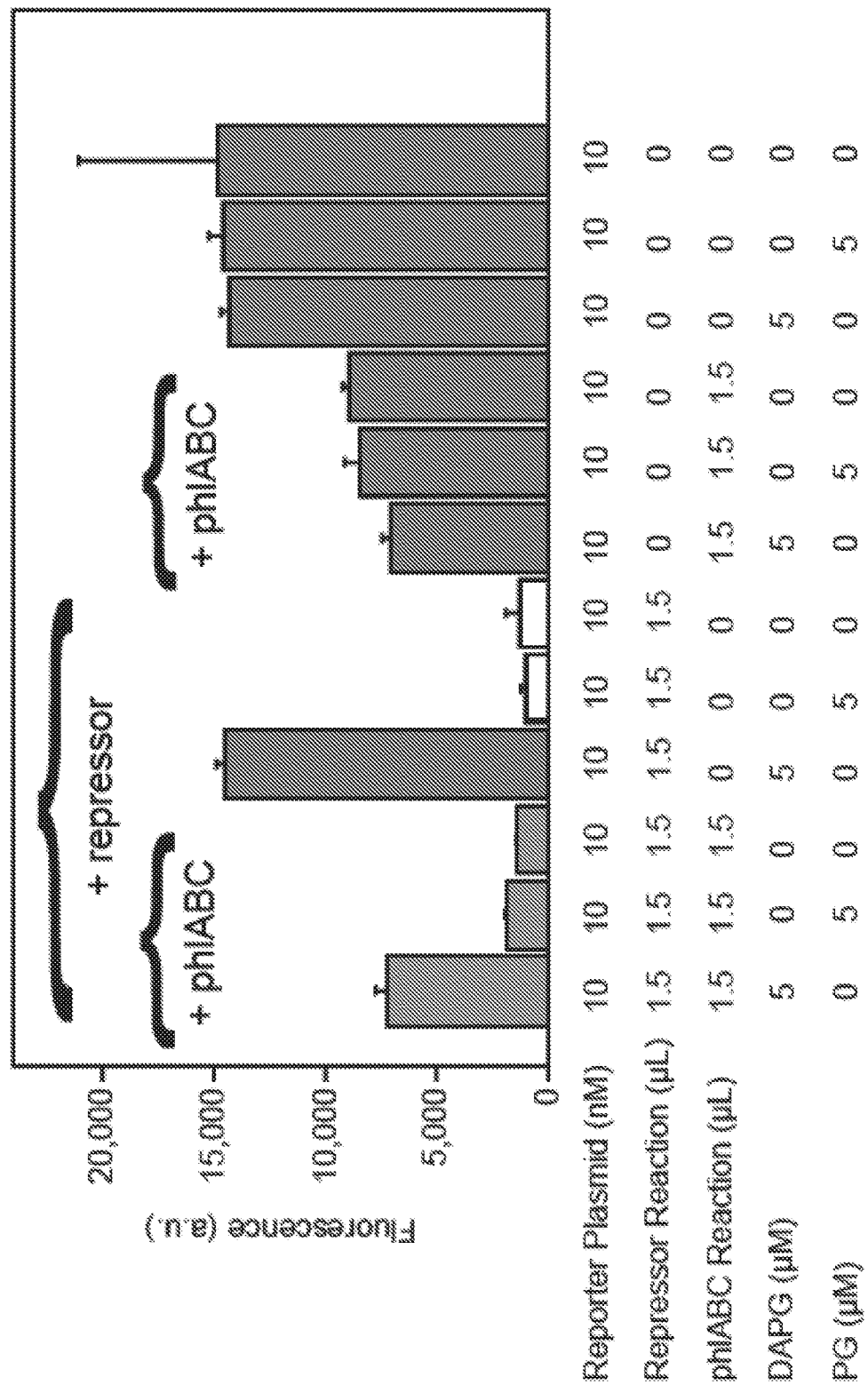

After designing an active DAPG sensor in CFPS, we next aimed to engineer a PG sensor by co-expressing the metabolic pathway phlABC in the reaction, which would convert PG to DAPG in situ (See FIG. 7). We tried three possible experimental designs. (See FIG. 8). In the first experiment (see FIG. 9A), we supplemented a third plasmid encoding the entire operon behind a T7 promoter into the cell-free reaction. However, we observed massive inhibition of reporter protein synthesis in the presence of the operon plasmid, even down to very low concentrations of its template DNA. As a result, we detected no ON activity in the presence of PG. (See FIG. 10A). To determine whether or not this effect was due to competition for transcription-translation resources or due to active poisoning by the enzymes, we expressed the phlABC enzymes and repressor in separate CFPS reactions, then doped these spent, enzyme-enriched reactions into fresh CFPS reactions with the reporter plasmid. (See FIGS. 9B, 10B). Even without the possibility of competition for ribosomes, supplementation of even small amounts of the phlABC reaction product poisoned the final reaction.

Figure 11:
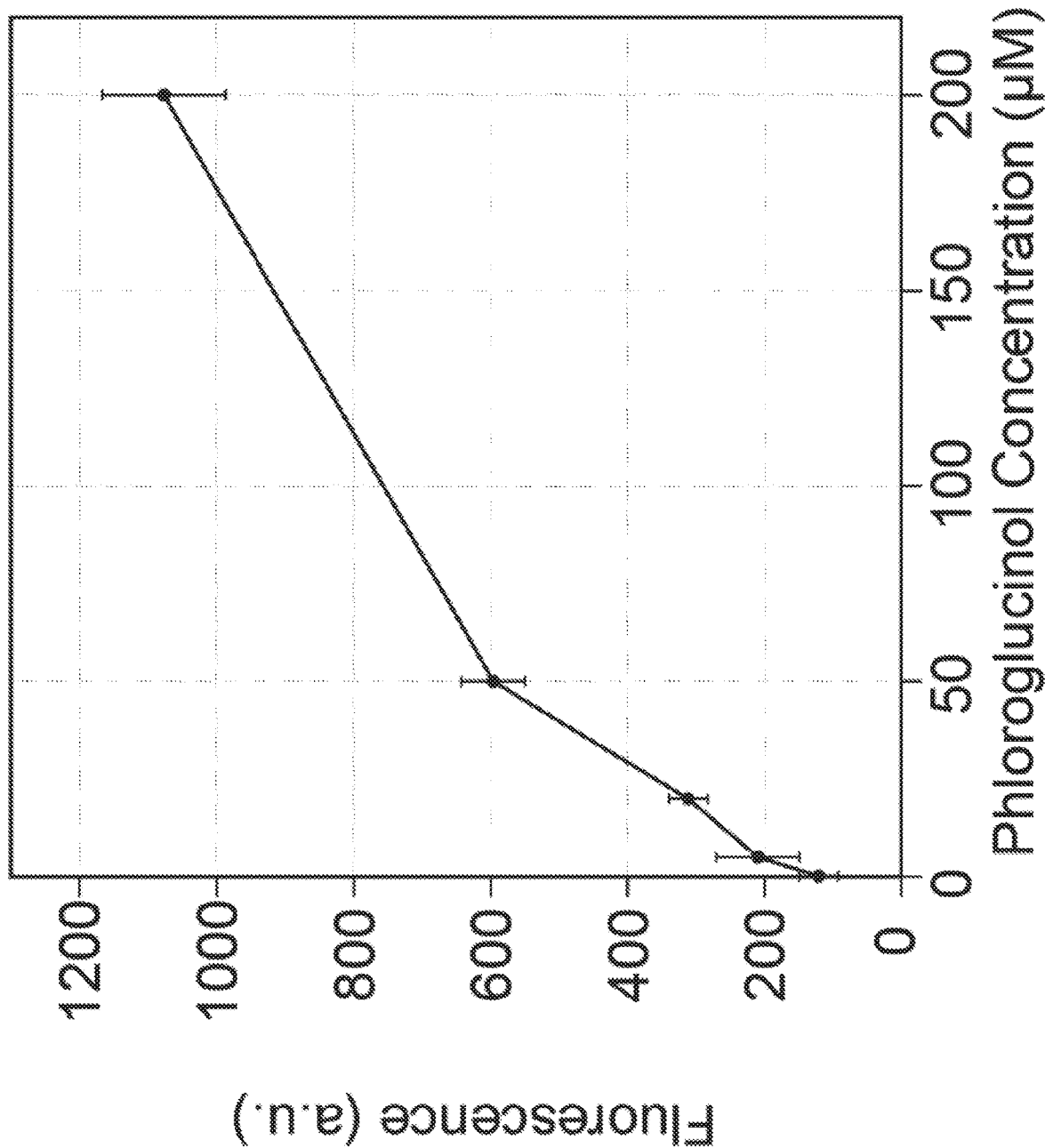
FIG. 11. Detection of phloroglucinol metabolized to diacetyl-phloroglucinol in enriched cell extract via DAPG sensor using phlABC enriched extract.
Figure 12:
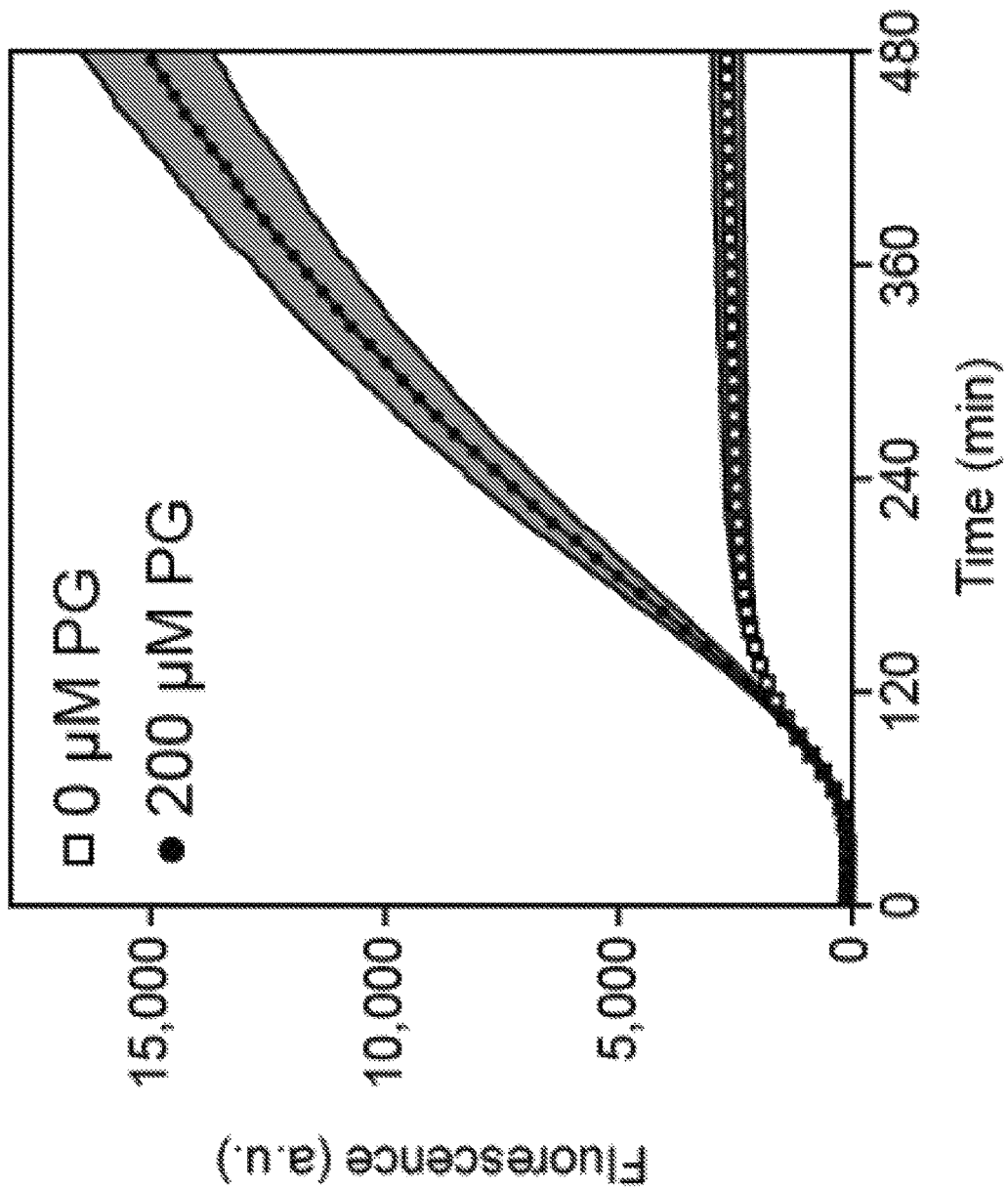
FIG. 12. Lyophilization of DAPG sensor components in tubes and detection of PG after rehydration in tube.
Figure 13:
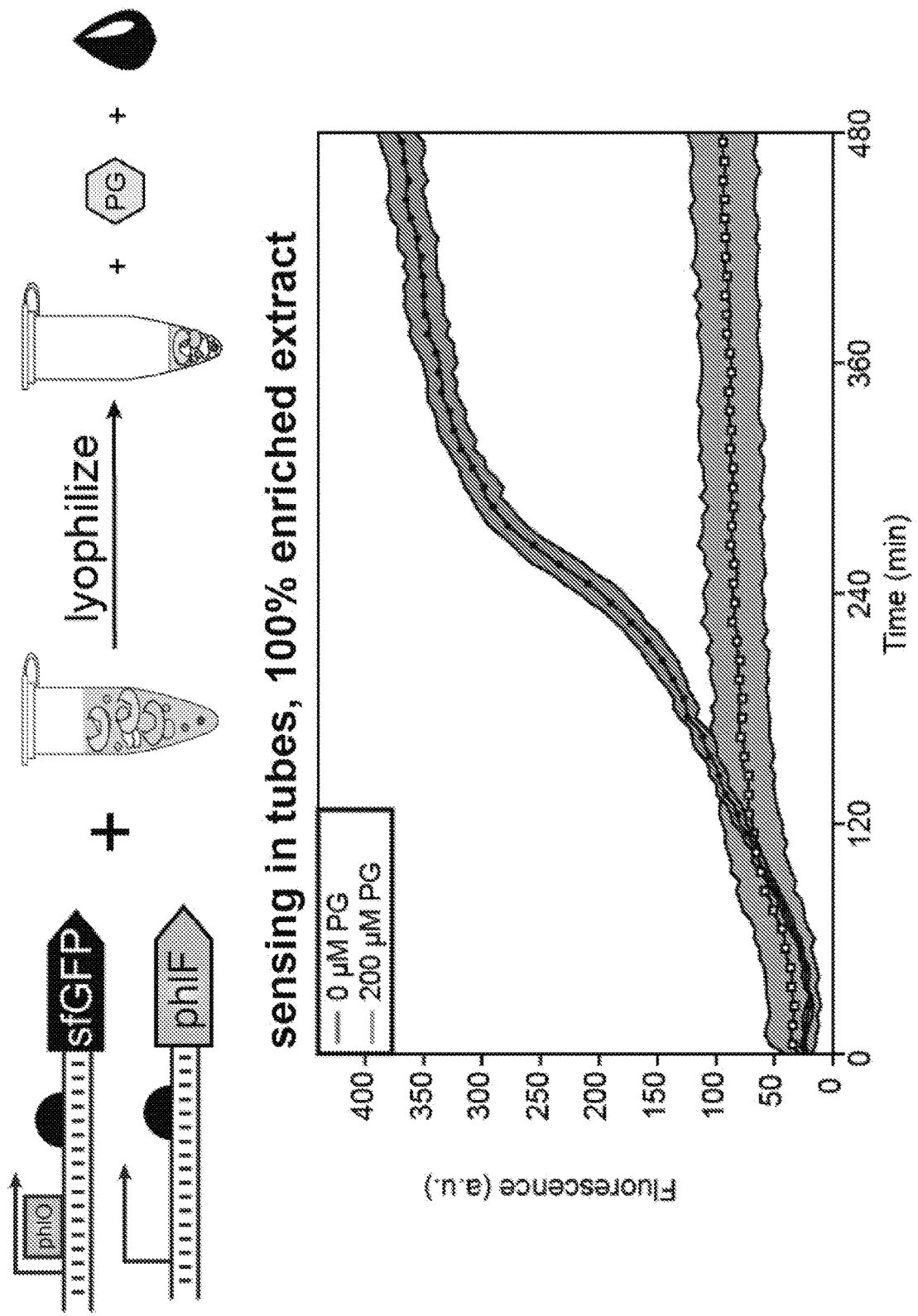
FIG. 13. Detection of phloroglucinol using DAPG sensor and diluted extracts to mitigate extract poisoning effect.
Figure 14:
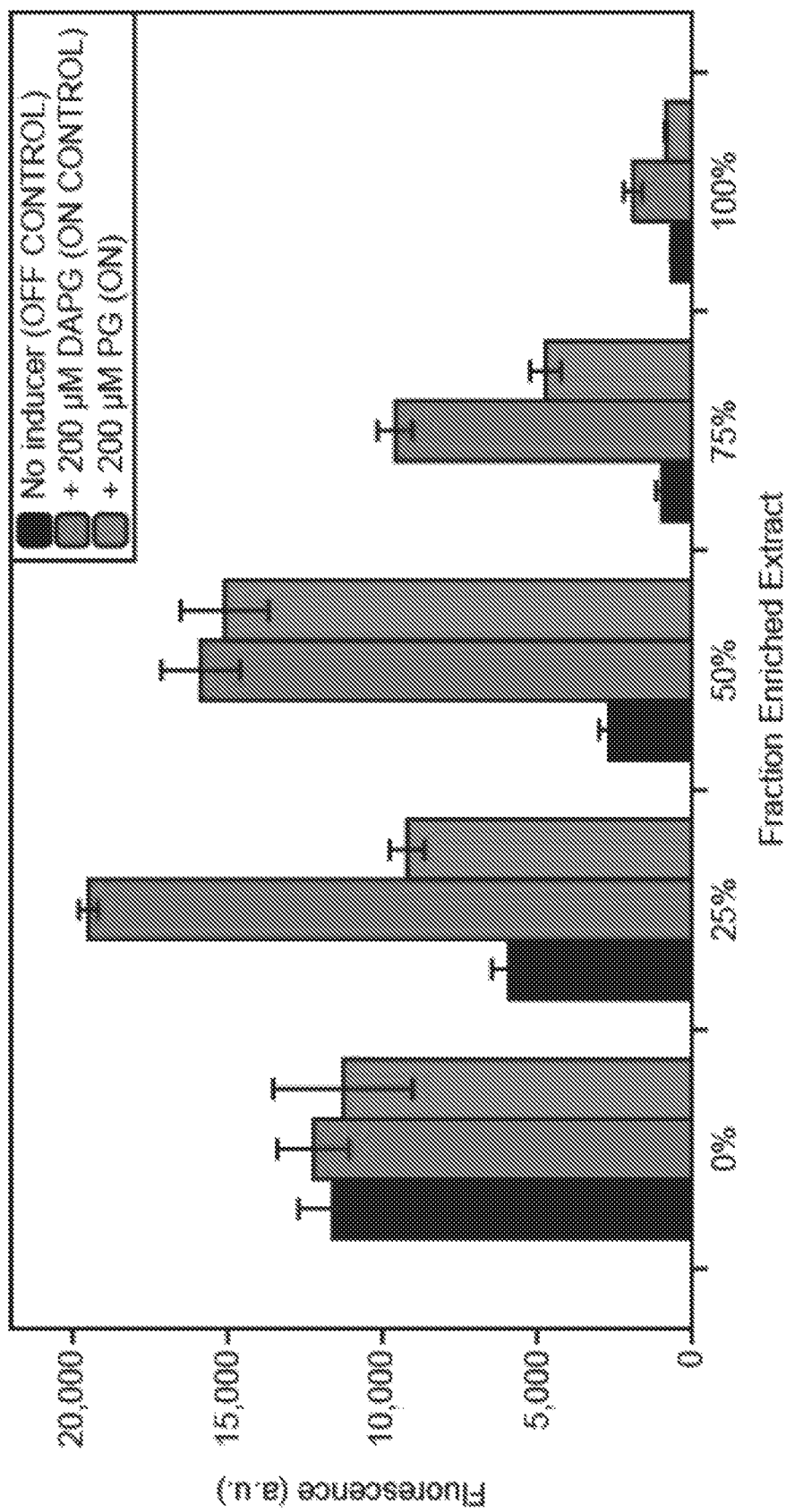
FIG. 14. Optimized cell-free sensor results. (A) Optimized extract sensor mixed 50:50 with blank extract shows around 7-fold activation in the presence of saturating phloroglucinol (200 µM) at an 8-hour endpoint. (B) GFP fluorescence in the ON state can be detected on paper.
Figure 14:
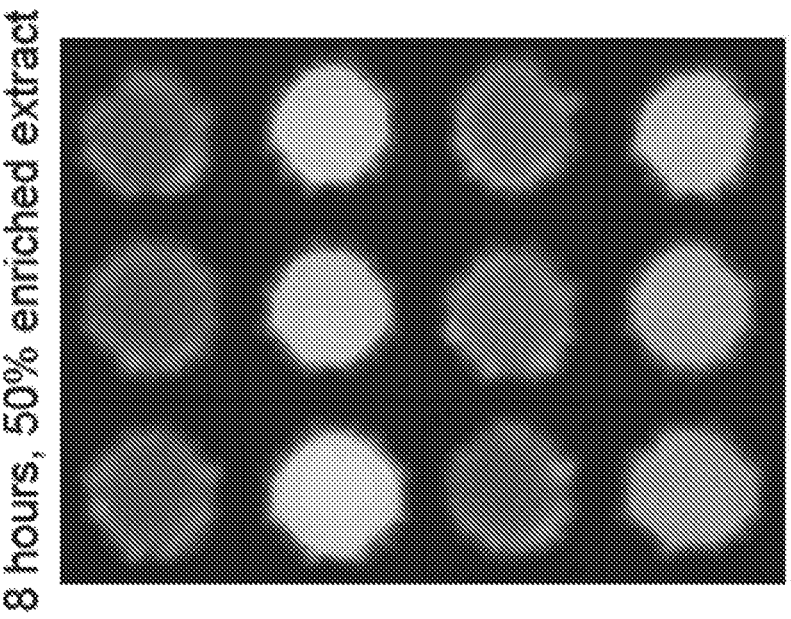

In our third and final design (see FIG. 9C), we aimed to enrich the phlABC pathway enzymes in the reaction by inducing overexpression of the enzymes in the bacterial culture used to source the extract. We prepared three extract variants, changing both the strain and the induction level of the enzymes. In each case, we observed growth constraints upon induction of phlABC synthesis, and the final extracts suffered in productivity even for the synthesis of constitutive reporters. In the best design, we did observe PG-dependent induction of protein synthesis in the presence of the optimized repressor and reporter plasmids, despite a low ON state (See FIG. 11). We demonstrated that this induction is maintained after freeze-drying the final reaction and rehydrating it in the presence of phloroglucinol (See FIG. 12). Finally, we showed that the ON activity can be massively improved by 50:50 mixing of the phlABC-enriched "weak" extract with a more productive blank extract without sacrificing its sensing capability (See FIG. 13). In the best extract mixing case, we observed maximal PG induction at around 100 µM ligand, a dynamic range of 7-fold, and a linear response range between 1 and 100 µM. (See FIG. 14A). We then transferred the active cell-free reactions into paper-based reactions. The paper-based sensing experiments were carried out using identical conditions and extracts that were successful for the experiments in tubes. Notably, the first round of paper-based experiments showed relatively high leak, where the OFF state where no PG was added was indistinguishable from the ON state (200 µM) at the kinetic endpoint. By increasing the concentration of repressor plasmid supplied to the reaction, however, we were able to achieve activation of the circuit on paper with sufficient signal over background to be visible by eye under a blue light. (See FIG. 14B).

Figure 15:
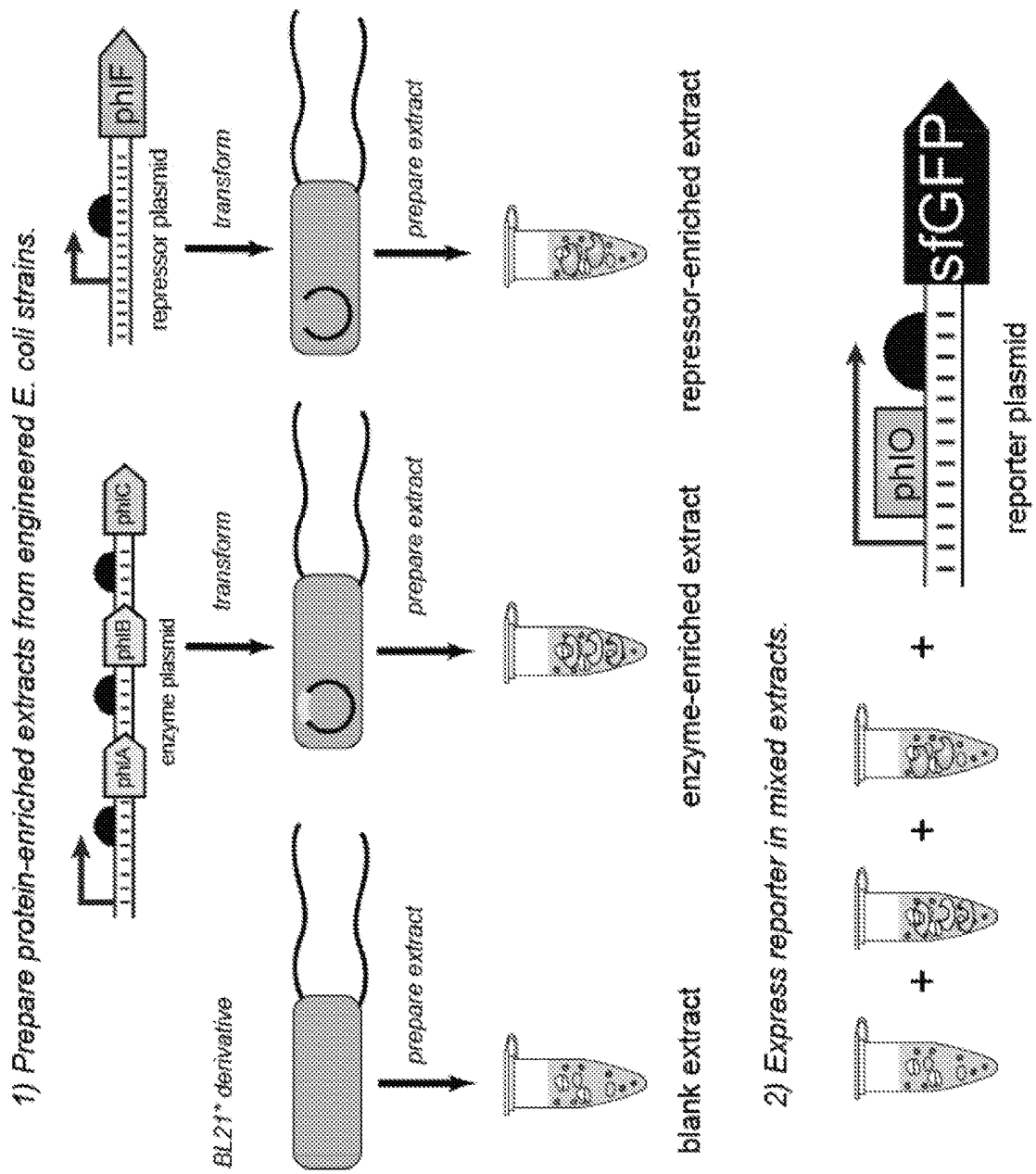
FIG. 15. Schematic illustration of preparation of individual non-enriched extract ("blank extract"), extract enriched in phlA, phlB, and phlC, and extract enriched in phlF and mixing of individual extracts (i.e., dilution of enriched extracts) for use with a reporter plasmid.
Figure 16:
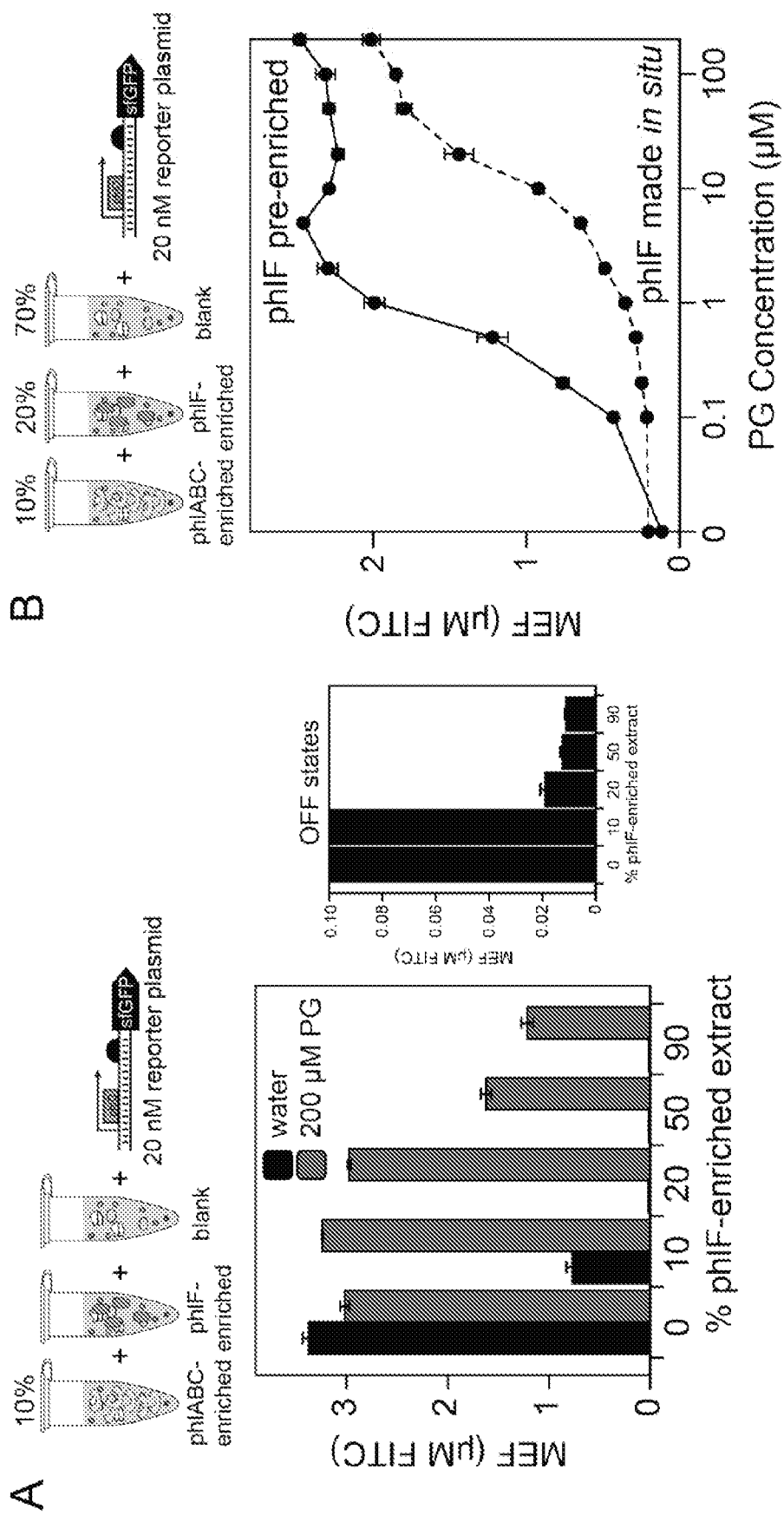
FIG. 16. Robust, leak-free detection of phloroglucinol using phlF and phlABC-enriched extracts. (A) Titration of 20% phlF enriched extract greatly reduces leak of the sensor. (B) phlF pre-enrichment also shifts the dose-response curve for phloroglucinol one order of magnitude to the left with a new limit of detection around 1 µM.

To address sensor leak, we next hypothesized that pre-enriching the cell-free sensing reaction with the repressor, phlF, could prevent reporter protein synthesis before sufficient repressor has accumulated in the reaction. To do this, we adapted a three-extract mixing strategy, where a blank extract is mixed with one enriched with the enzyme pathway phlABC and another one enriched with the transcription factor phlF (See FIG. 15). At the optimal ratio, this combination of extracts gave a higher ON state and much reduced leak, with overall sensor dynamic range of around 150× (See FIG. 16A) and a limit of detection around 1 µM PG (See FIG. 16B).

Example 4

Design and Optimization of Cell-Free Cyanuric Acid and Atrazine Biosensors

Recent advances in cell-free synthetic biology have spurred the development of in vitro molecular diagnostics that serve as an effective field-deployable alternative to whole-cell biosensors. However, cell-free sensors for detecting most organic water contaminants are sparse, partly because few characterized, natural biological sensors detect such pollutants. Here, we present a platform for the cell-free detection of one critical water contaminant, atrazine, by combining a previously characterized cyanuric acid biosensor with a reconstituted atrazine-to-cyanuric acid metabolic pathway composed of several protein-enriched bacterial extracts mixed in a single pot. Our sensor discerns environmentally relevant levels of atrazine within two to three hours of incubation, outperforming previously reported whole-cell atrazine sensors. We show that our sensor's response can easily be tuned through facile manipulations of the cell-free open reaction environment. Due to the high modularity of this strategy, we believe that this work will serve as an effective benchmark for rapid field-deployable detection of many other organic water contaminants.

Cell-free gene expression (CFE) has recently emerged as a powerful strategy for on-demand molecular biosensing, since cell-free systems minimize many of the constraints of whole-cell sensors, including mass transfer barriers, cytotoxicity, genetic mutation, plasmid loss, and biocontainment.[1,10] Because CFE reactions are shelf-stable when freeze-dried but activate upon hydration, these sensors can easily be used outside the laboratory, at the point of sampling in the field.[11] However, previously reported cell-free sensors detect either nucleic acids[12,13] or a very limited set of chemicals, almost always using well-characterized *E. coli* allosteric transcription factors.[14–16] One contaminant of concern that has not previously been detected in vitro is atrazine, a potent and frequently abused herbicide in the United States. No natural biosensor exists for atrazine, but it is naturally catabolized into cyanuric acid, the target analyte for the transcription factor AtzR from *Pseudomonas* sp. ADP-1.

Approach for Detecting Cyanuric Acid

Although CFE systems have been developed from *Pseudomonas*[17] (the native host of AtzR), *Pseudomonas* extracts produce far less protein than corresponding extracts prepared from *E. coli*, which have been optimized over several decades.[18-20] Our success in developing a functional *E. coli* CYA sensor using the heterologous transcription factor AtzR thus motivated our approach to use *E. coli* extracts to build a cell-free sensor where AtzR regulates expression of sfGFP. We therefore designed two new constructs for cell-free expression: an AtzR-expressing plasmid and a reporter plasmid where sfGFP synthesis is inducible by CYA (See FIG. 17A). By cloning the transcription factor and reporter into separate plasmids, the ratio of expression of each construct in the cell-free reaction can be tuned simply by changing the amount of each plasmid supplied to the reaction. This approach is simpler than the corresponding workflow for whole-cell biosensors, in which plasmid copy numbers must be manipulated while maintaining compatibility between origins of replication and selection markers.

To design cell-free expression constructs, we rationally adjusted the constructs that were functional in vivo to better resemble cell-free expression cassettes. In the AtzR sensor plasmid, we replaced the constitutive bacterial promoter to a T7 promoter, since T7 RNAP is the most common and productive polymerase for making proteins in cell-free expression systems, resulting in an enhancement of protein yield by a factor of 2-3.[9,21] For the reporter plasmid, we started with a design based on Promoter P5, since it gave both a high ON signal and fold-induction in vivo, and previous work has shown that very strong promoters are necessary for robust protein synthesis in extract.[9] We additionally included a pHP14 RNA stability hairpin immediately after the transcriptional start site in the reporter plasmid, since secondary structure in the mRNA 5' end is necessary for robust expression from bacterial promoters in cell-free conditions.[9] Both expression cassettes were then placed into high-copy vectors.

The two plasmids were then purified and doped into a cell-free reaction containing post-lysis processed *E. coli* extract[9] and the additional biological cofactors required for transcription and translation in vitro. The reactions were incubated at 30° C. for 4 hours and the reaction progress was monitored by continuously measuring fluorescence on a plate reader.

Figure 17:
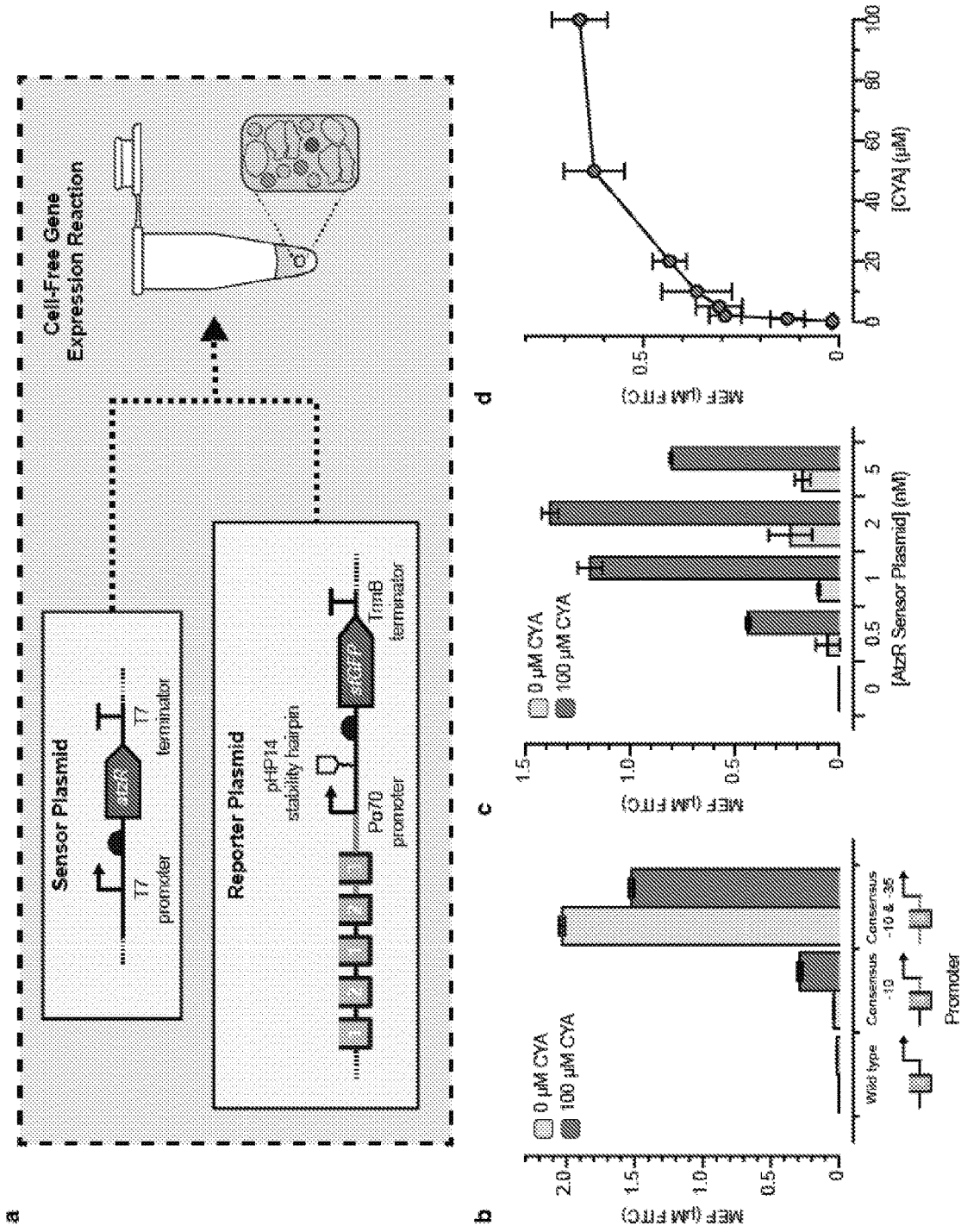
FIG. 17. Design of a cell-free cyanuric acid sensor. (a) Two plasmids—one encoding the AtzR transcription factor (sensor plasmid) and one encoding sfGFP regulated by AtzR (reporter plasmid)—were added to 10 µL cell-free gene expression reactions and sfGFP production after four hours at 30° C. was measured in the absence (OFF) and presence (ON) of 100 µM cyanuric acid (CYA). (b) Three promoter variants that replaced the native *Pseudomonas* $\sigma^{70}$ recognition sites with the consensus *E. coli* −10 and −35 sites were tested in a small screen to identify promoter variants that were functional for cell-free CYA-induced activation. A promoter where only the −10 site was converted to the *E. coli* consensus sequence (TATAAT) gave the highest fold-induction and was carried through for subsequence experiments. In every case, reporter DNA plasmid was added at 10 nM, and the AtzR-expressing plasmid was kept at 1 nM. (c) Titration of AtzR-expressing plasmid against 10 nM reporter plasmid reveals that the optimal condition has 1 nM of AtzR-expressing plasmid to minimize sensor leak and potentially to maintain adequate distribution of translational resources between the two proteins. (d) Dose-response curve for cyanuric acid induction at optimal plasmid concentrations shows a wide linear operating range over 0-100 µM CYA. Error bars represent 1 standard deviation from 3 technical replicates. Fluorescence is reported using mean equivalent fluorescence (MEF) of fluorescein isothiocyanate based on a previously developed standard curve.

We observed constitutive transcription in our initial reporter design based on Promoter P5 (with consensus *E. coli* $\sigma^{70}$ −10 and −35 sites) even in the absence of CYA (See FIG. 17B). This result was unexpected as it contradicts the results obtained in cells. We hypothesized that variability in reaction environments between cells and in CFE, particularly the concentration of the accessory factors for transcription, gave rise to this difference. We therefore prototyped new reporter designs and observed that, surprisingly, a promoter based on Promoter P2 with the wild-type *Pseudomonas* −35 sequence but the consensus *E. coli* $\sigma^{70}$ −10 sequence, responded well to 100 μM cyanuric acid in vitro (See FIG. 17B) with ~8-fold-induction and low sensor leak. We thus applied this design to further optimize the cell-free sensor.

We next aimed to find the optimal ratio between the AtzR-expressing plasmid and the reporter plasmid that gives the best fold-induction. We therefore fixed the sfGFP reporter plasmid concentration in the reaction to 10 nM and varied the concentration of the AtzR-expressing plasmid. Fluorescence measurements were taken after a 4-hour incubation in either the absence (OFF) or presence (ON) of 100 μM CYA (See FIG. 17C). When no AtzR-expressing plasmid was supplied to the CFE reaction, we observed no sfGFP production, consistent with an activation mechanism. As the AtzR template concentration increased, we observed an increase in both the ON and OFF states, up to 2 nM AtzR plasmid. Beyond 2 nM of the AtzR plasmid, sfGFP production tapered off, likely due to competition for translational resources between reporter and transcription factor synthesis in the batch reaction. We chose 1 nM AtzR plasmid and 10 nM reporter plasmid as the optimal condition, which achieves >12-fold-induction in the presence of 100 μM CYA. These results highlight the power of cell-free systems for rapidly tuning sensors, since the analogous cellular experiments would have required extensive cloning and testing.

Figure 18:
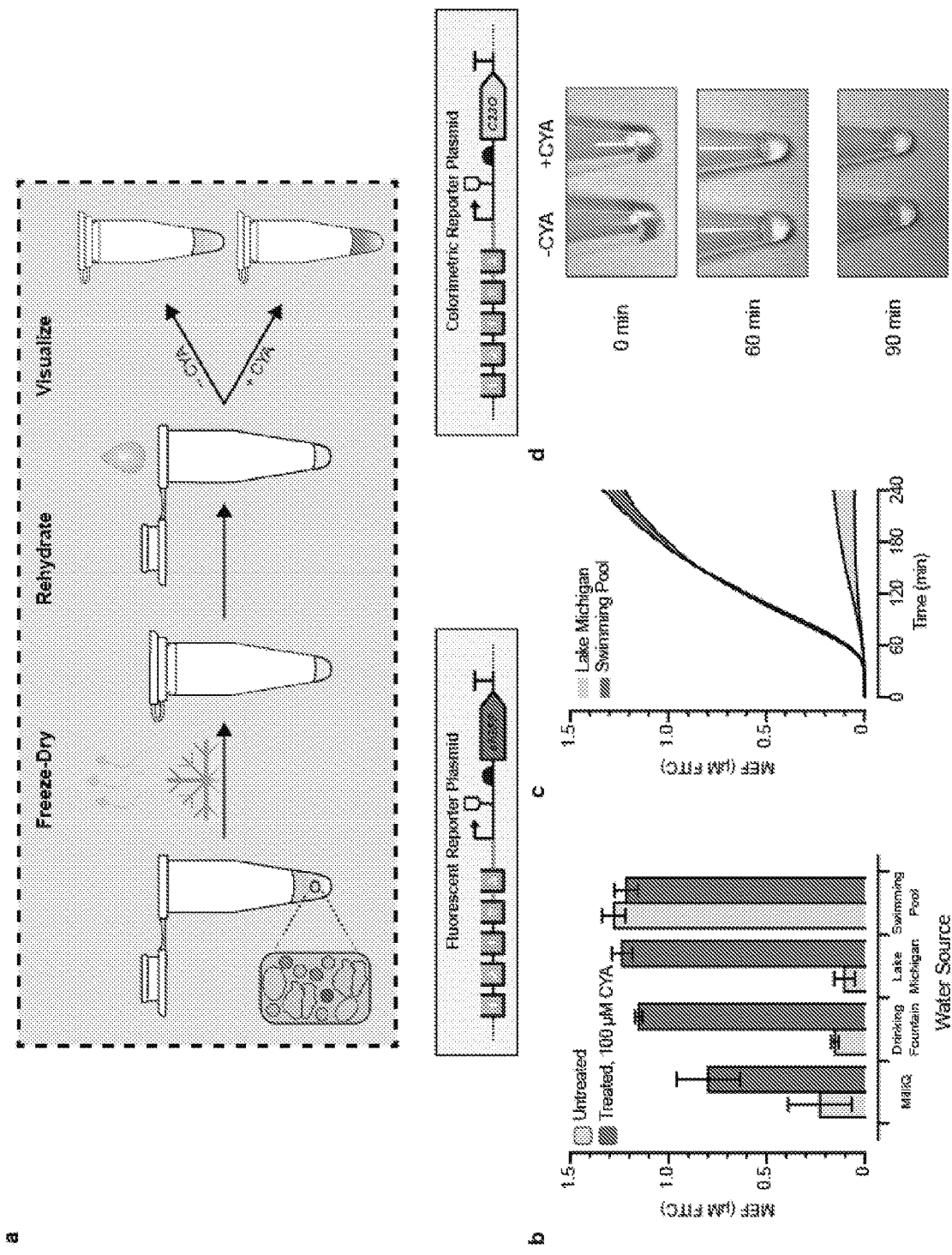
FIG. 18. Proof-of-concept for field-deployable cyanuric acid sensing using a cell-free biosensor. (a) Optimized cell-free reactions are prepared without cyanuric acid (CYA), freeze-dried, and then rehydrated with unfiltered environmental water samples. (b) CYA in environmental water samples can be detected from freeze-dried cell-free reactions. Pre-mixed cell-free reactions were freeze-dried and rehydrated with 90% of an environmental water sample and 10% of either MQ water (OFF) or 10% MQ water spiked with a final concentration of 100 µM CYA (ON). sfGFP fluorescence is specifically induced by CYA in every sample except the pool water, which is expected to already contain CYA even in the OFF state. (c) Time course comparisons of the OFF state from panel B, for the unfiltered environmental water samples that were not spiked with CYA. Pool water can be distinguished against lake water in less than one hour. (d) Time course comparison for activation of cell-free reaction driving expression of catechol 2,3-dioxygenase, an enzymatic reporter that cleaves its colorless substrate catechol into a yellow product, cis,cis-muconic acid. CYA was added at a concentration of 600 µM in the ON state to a fresh cell-free reaction incubated at 30° C. and monitored for 90 minutes. Pictures are cropped representative images from the experiment, which was done in triplicate. Error bars in b and c represent one standard deviation from three technical replicates. Fluorescence in b and c is reported standardized to mean equivalent fluorescence (MEF) of fluorescein isothiocyanate based on a previously developed standard.

With a cell-free CYA sensor at hand, we aimed to test if our cell-free sensor could directly detect CYA in natural and synthetic water samples, as a final validation that a cell-free biosensor can be deployed for reporting on relevant concentrations of CYA outside the laboratory. We freeze-dried pre-mixed reactions containing the sensor and reporter plasmids, reaction buffer, and extract, and rehydrated them with water samples obtained from a drinking fountain, Lake Michigan (Evanston, IL), and a chlorinated local swimming pool (See FIG. 18A). In each case, we spiked one reaction with 100 μM CYA to serve as a control for the impact of water quality on the cell-free reaction's performance. Importantly, to better reflect real-world operating conditions for such a sensor, we did not filter or otherwise process any of the water samples. We then measured sfGFP production on a plate reader over 4 hours.

For the samples hydrated with laboratory water, fountain water, and lake water, the ON states created by spiking in CYA showed appreciable activation versus the OFF states, and similar sfGFP yields were obtained to the yields from fresh reactions in the earlier experiments. This result shows that the reactions are not poisoned by the unfiltered environmental water samples that we tested (See FIG. 18B). The pool water sample, which was expected to have CYA, was activated even without the CYA spike-in and showed activation relative to the lake water sample in less than an hour (See FIG. 18C). We conclude that our cell-free biosensor is able to detect whether or not an arbitrary environmental water sample contains CYA. Since we did not observe sample matrix poisoning effects in this experiment, we hypothesize that a standard curve of CYA samples could thus be developed in the future as a method for quantification of CYA concentrations at the point-of-use.

Finally, we aimed to validate if a visible output signal for the sensor could be generated without a plate reader to enable equipment-free detection of CYA from environmental samples. Specifically, we prototyped a sensor to report water samples with dissolved CYA above the upper recommended concentration of 600 μM. Because fluorescence of sfGFP is difficult to detect by the unaided eye, particularly in the early stages of the reaction, we replaced the coding sequence of the reporter plasmid instead with the enzyme catechol 2,3-dioxygenase (C23DO). C23DO cleaves its substrate, catechol, into a yellow cis,cis-muconic acid product, so the reaction progress can be directly read out from the visible color.[22]

We thus prepared the sensing experiment in tubes supplemented with catechol maintained at 30° C. and visually monitored the reaction progress over time. Activation of the reporter was observed by the production of a yellow color within 1 hour (See FIG. 18D). Interestingly, when the sensing reaction was prepared in tubes instead of the plate reader, leak was observed on longer timescales, such that the OFF state was fully activated within 90 minutes. Our results here hint that further optimization of the reaction conditions will be necessary to make a colorimetric reporter viable for quantification of cyanuric acid in a sample. Nonetheless, this experiment provides a powerful proof-of-principle for equipment-free, field-deployable detection of cyanuric acid at relevant concentrations.

Approach for Detecting Atrazine

We developed a strategy for expanding the scope of small molecule sensing in *E. coli* extracts by demonstrating the ability of the LysR-type transcriptional regulator (LTTR) atzR to detect its cognate ligand, cyanuric acid, in vitro. This sensor only activated when the freeze-dried reactions were rehydrated with unfiltered pool water samples containing high (hundreds of micromolar) concentrations of cyanuric acid.

Here, we expanded the capacity of this sensor for the rapid cell-free detection of atrazine, a highly potent and widely abused herbicide, which has been estimated to contaminate nearly 90% of water taps in the United States, frequently at concentrations above the EPA's limit.[23] To do this, we combine our previously developed cell-free cyanuric acid sensor with a cell-free reconstituted metabolic pathway that converts atrazine to cyanuric acid, all in a single pot. Our sensor is capable of discriminating environmentally relevant levels of atrazine within two to three hours of incubation.

To design our cell-free atrazine sensor, we took inspiration from the native *Pseudomonas* ADP-1 species, which detects atrazine by metabolizing it into the sensible analyte cyanuric acid through a three-enzyme pathway encoded on the atzABC operon (See FIG. 19A).[24,25] We hypothesized that by co-expressing each of these enzymes, as well as the transcription factor atzR and a cyanuric acid-inducible fluorescent reporter, we would observe atrazine-inducible protein synthesis. Recently, such a strategy was validated in cell-free using a one-enzyme pathway where the enzyme, transcription factor, and reporter are encoded on separate plasmids.[26] However, co-expressing five different proteins would likely diminish reporter titer and delay the response time. Instead, we pre-enriched four separate extracts (one each with atzR, atzA, atzB, and atzC) by inducing protein overexpression from a *E. coli* host strain before lysing the cells and preparing extract from them. This approach greatly simplifies the sensor design since the load of each enzyme in the final cell-free reaction can be controlled linearly by the fraction of its pre-enriched extract that was mixed in. We observed particularly severe growth inhibition and plasmid burden when overexpressing atzB, an effect which has been previously reported in an attempt to convert a whole-cell cyanuric acid biosensor into one detecting atrazine.[27] Pre-expressing this protein in a source strain rather than attempting to make it in situ in the reaction shifts the poisoning effect away from the sensing reaction, highlighting another advantage of reconstructing these complex metabolism-sensing pathways in vitro.

Figure 19:
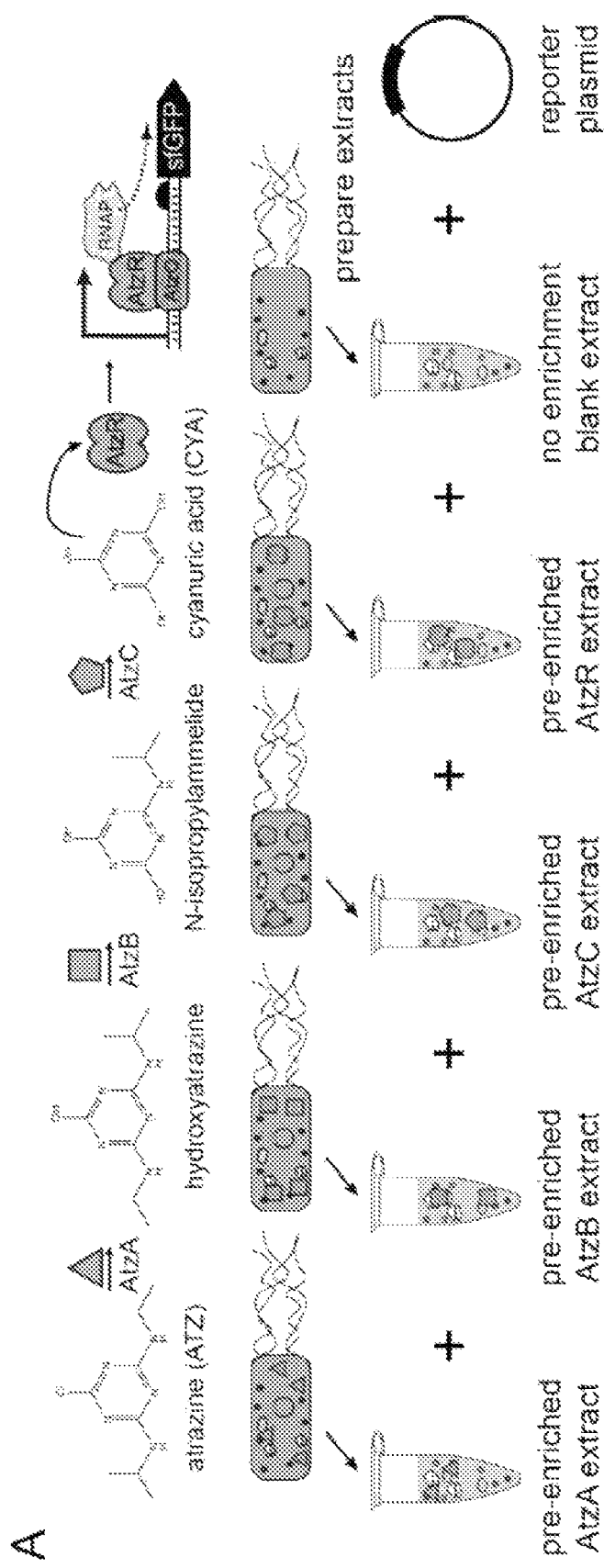
FIG. 19. Design of a cell-free atrazine biosensor. (A) Atrazine is catabolized by a three-enzyme pathway into cyanuric acid, which can activate transcription by the atzR transcription factor. The four required proteins (three enzymes and the transcription factor) are overexpressed in separate strains of BL21 *E. coli*, then lysed and prepared into extracts, which can be mixed in fixed ratios to detect atrazine. (B) Cell-free detection of atrazine requires the presence of all three pathway enzymes. (C) The sensor is capable of detecting cyanuric acid and atrazine, as well as propazine, a triazine of similar chemical structure. CYA=cyanuric acid; ATZ=atrazine; MEL=melamine; PRO=propazine. Error bars represent the standard deviation of sfGFP fluorescence measurements, correlated to a known linear FITC standard, from three technical replicate reactions.
Figure 19:
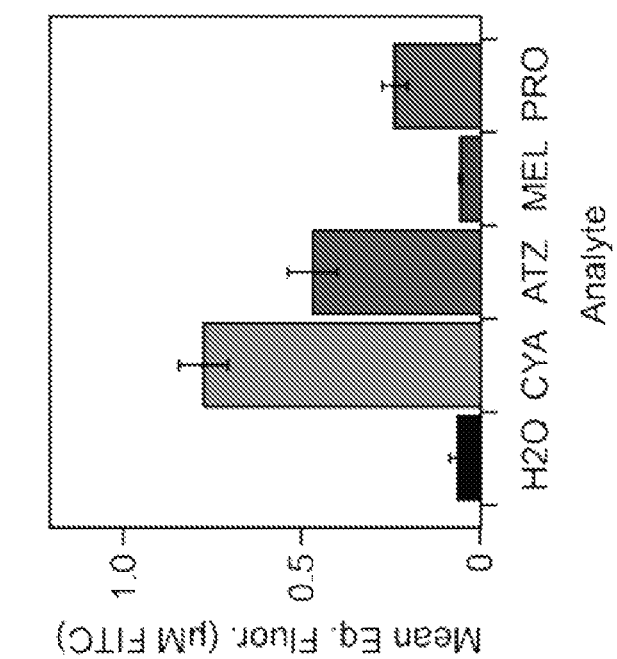
Figure 19:
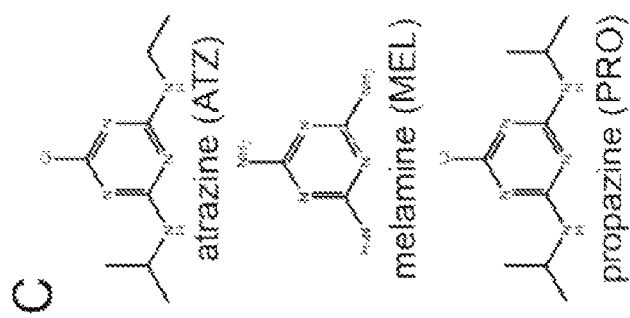
Figure 19:
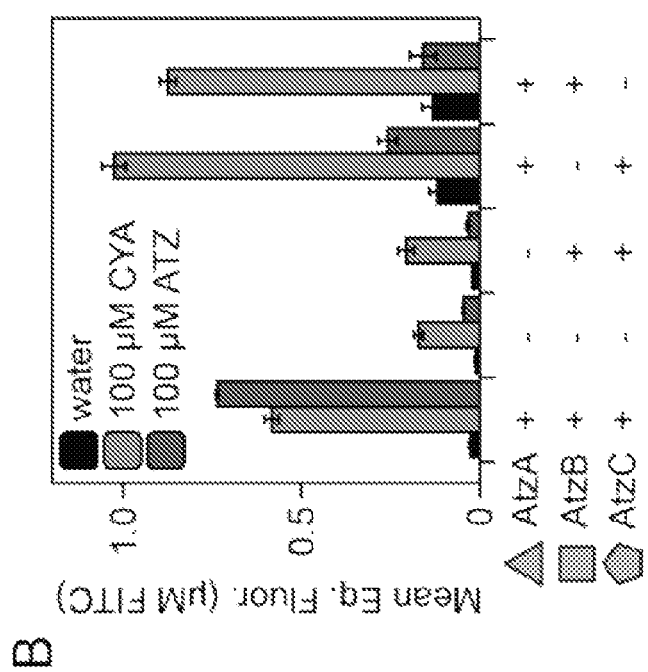

By mixing all of the protein-enriched extracts together along with a "blank" extract that was not enriched with any protein and an optimized reporter plasmid encoding super-folder green fluorescent protein (sfGFP) behind the atzR operator, we could detect atrazine doped into a cell-free reaction at 100 µM (See FIG. 19B). This concentration is equivalent to the concentration of cyanuric acid that saturated atzR activation in our previous work. To the best of our knowledge, this is also the most complex demonstration to date for coupling an upstream metabolic module to an inducible transcriptional biosensor, either in cells or in cell-free. If any of the individual enzyme-enriched extracts was left out of the reaction and replaced with a blank extract, the sensor could not effectively detect atrazine (See FIG. 19B).

Figure 20:
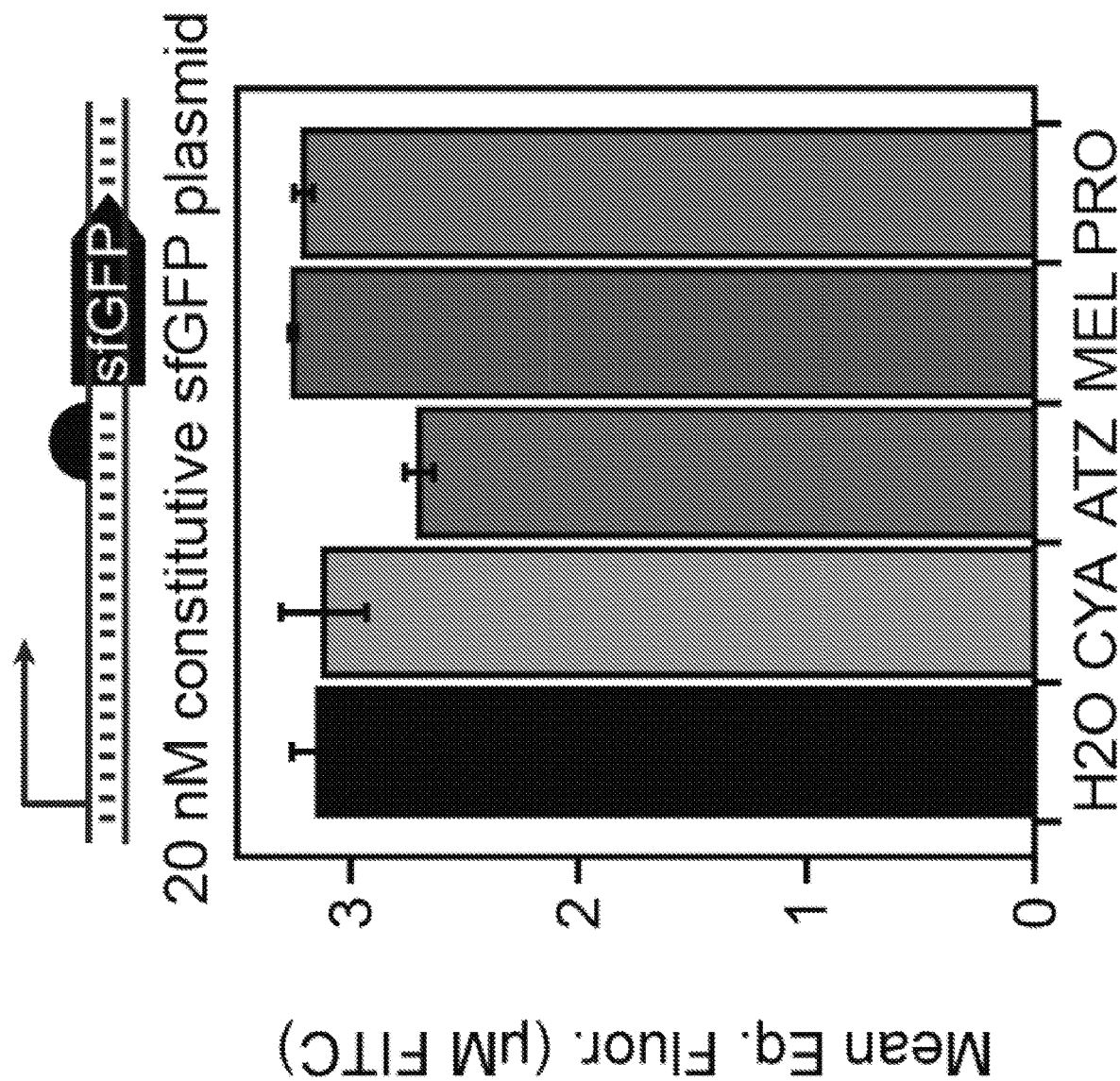
FIG. 20. Triazine poisoning. Minimal poisoning of a model, unregulated cell-free protein synthesis reaction is observed from 100 µM of the triazines atrazine, melamine, or propazine. Error bars represent the standard deviation of sfGFP fluorescence measurements, correlated to a known linear FITC standard, from three technical replicate reactions.

To determine the sensor's versatility and also its specificity, we challenged the reaction with two other environmentally relevant triazines. We observed weak activation in response to propazine, which is more structurally similar to atrazine than the unreactive melamine (See FIG. 19C), suggesting that at least one of the pathway enzymes may have some promiscuous activity, though we did not characterize this further. We also validated that, even at 100 µM concentrations, the different triazines had negligible inhibitory effects on cell-free transcription and translation (See FIG. 20).

Figure 21:
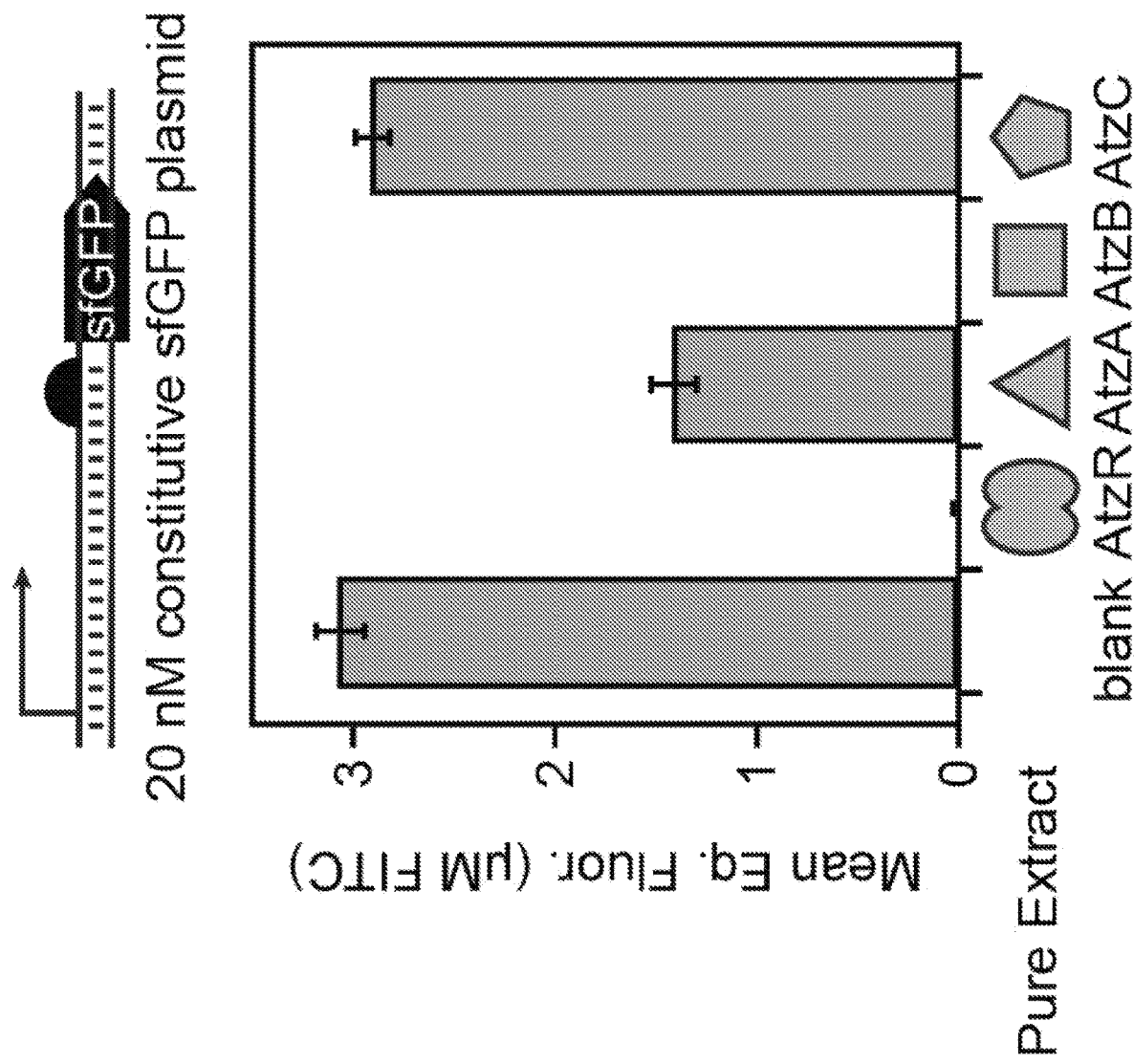
FIG. 21. Pure extract poisoning. Significant poisoning effects can be observed from protein-enriched extracts used to drive constitutive expression of sfGFP. Thus, an extract mixing strategy is necessary. Overexpression of AtzR and AtzB also resulted in severe growth defects in the host strain, consistent with the resulting very low-yield extract. Error bars represent the standard deviation of sfGFP fluorescence measurements, correlated to a known linear FITC standard, from three technical replicate reactions.

Satisfied that our cell-free sensor, composed of four different protein-enriched *E. coli* extracts and a blank extract, could detect saturating levels of atrazine, we next aimed to optimize its activity for use as a field-deployable atrazine sensor. In the mix-and-match approach in FIG. 19B, we observed a large amount of variability in the positive (cyanuric acid) and negative (water) controls. This disparity is likely caused both by enzyme-specific poisoning effects as well as general batch-batch inconsistencies between the extracts.[28] In particular, we found that all of the protein-enriched extracts were less productive than the unenriched extract in a control reaction. The atzB and atzR-enriched extracts, which were prepared from highly growth-inhibited strains, could not support any measurable sfGFP synthesis on their own (See FIG. 21). Because of the open reaction environment of the cell-free reaction, though, we could iteratively tune protein dosage levels by controllably mixing in each of the four enriched extracts at different ratios and buffering the mixture with a "blank" unenriched extract that would improve overall protein synthesis yields.

We thus aimed to identify the ratio of atzR:atzA:atzB:atzC-enriched extracts that gave the highest fold induction (ON/OFF) state for the sensor, where we continued to define the ON state inducer concentration to be 100 µM atrazine. First, we calculated the optimal fraction of the transcriptional activator atzR in the sensing reaction, just for detecting cyanuric acid, since in our previous work, we had only synthesized the atzR in situ in the reaction, off a second plasmid. The greatest fold induction was observed at 5% atzR-enriched extract, a ratio that minimizes leak and maximizes ON state, likely because that mixture also has the greatest amount of the blank extract (See FIG. 22A). Next, we performed iterative optimizations over the ratios of atzA-, atzB-, and atzC-enriched extracts in the reaction, starting from an assumption of 10% dosage for each sensor (See FIG. 22B-D). Surprisingly, we observed low sensitivity of the atrazine response to perturbations in the concentrations of these enzyme-enriched extracts, at least in the range of 1-10% of the total extract composition. Again, though, no response to atrazine could be observed if any of the enzyme-enriched extracts was individually left out.

At each condition, we chose the overall ratio that gave the highest fold induction (defined as sfGFP fluorescence in the ON divided by OFF state of the sensor). Using this coarse-grained optimization, we obtained an optimal response at 5% atzR, 10% atzA, 2% atzB, and 20% atzC-enriched extracts, with the balance made up by the blank extract.

Superior resolution would likely be obtained from high-throughput liquid handling, due to the difficulty in pipette dispensing very small volumes of viscous extract.

Figure 22:
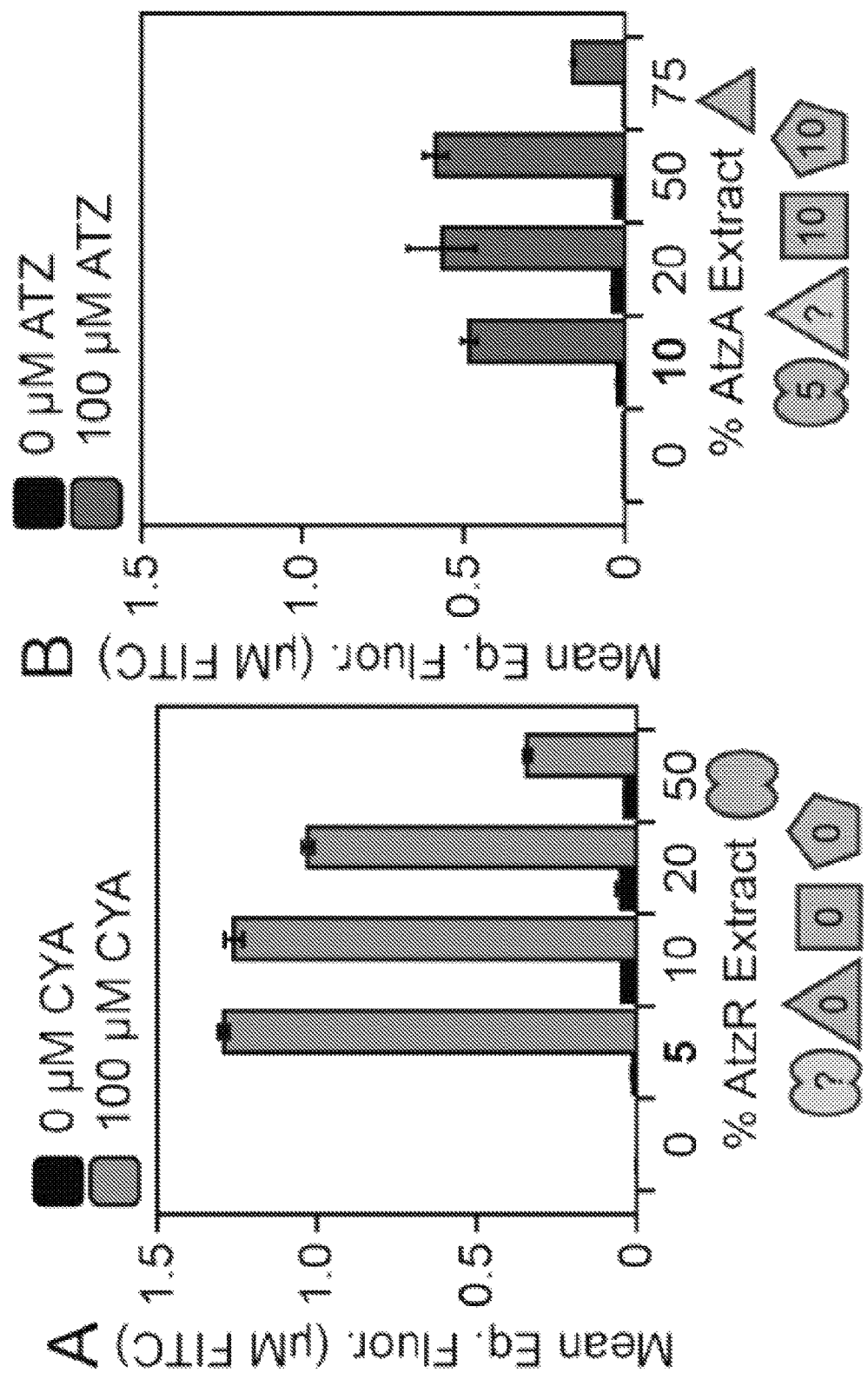
FIG. 22. Optimization of the cell-free atrazine sensor. (A-D) Iterative optimization of the ratios of the atzR, atzA, atzB, and atzC extracts in the final sensor mixture reveals that the optimal fold induction is achieved at 5% atzR-enriched, 10% atzA-enriched, 2% atzB-enriched, and 20% atzC-enriched, although the sensor's overall output response is relatively stable within this range as long as a nonzero fraction of each extract is supplied. (E) Atrazine dose-response curve for the optimized sensor suggests that the overall limit of detection is around 20 which is consistent with previous results reported for the cell-free cyanuric acid sensor. (F) Protein synthesis, read out as sfGFP fluorescence, can distinguish the ON from OFF state within one hour, and at endpoint achieves approximately 8-fold induction. The bilobe, triangle, square, and hexagon respectively represent atzR, atzA, atzB, and atzC, and the numbers inside represent their final contribution to the extract makeup as a percentage. Error bars represent the standard deviation of sfGFP fluorescence measurements, correlated to a known linear FITC standard, from three technical replicate reactions.
Figure 22:
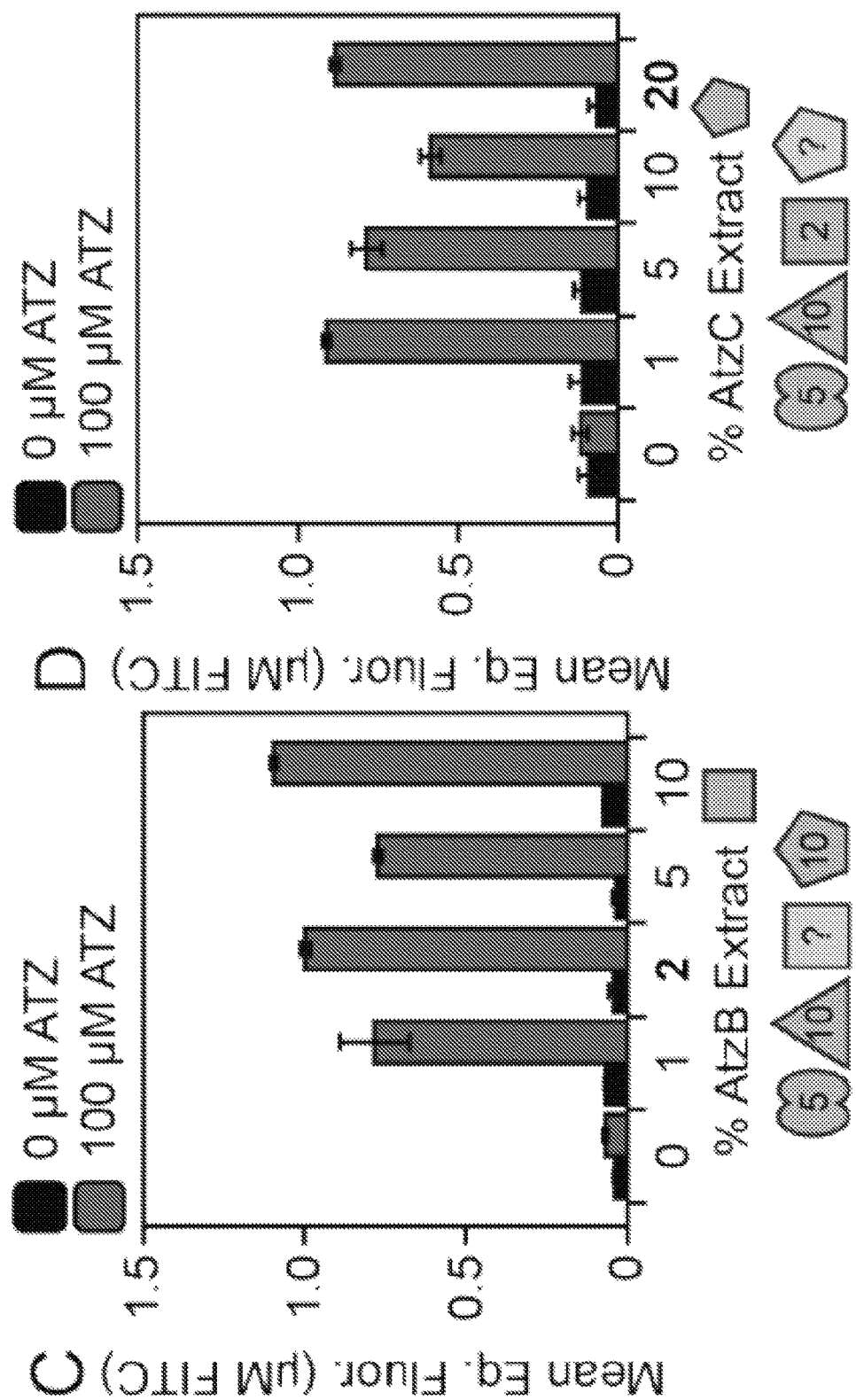
Figure 22:
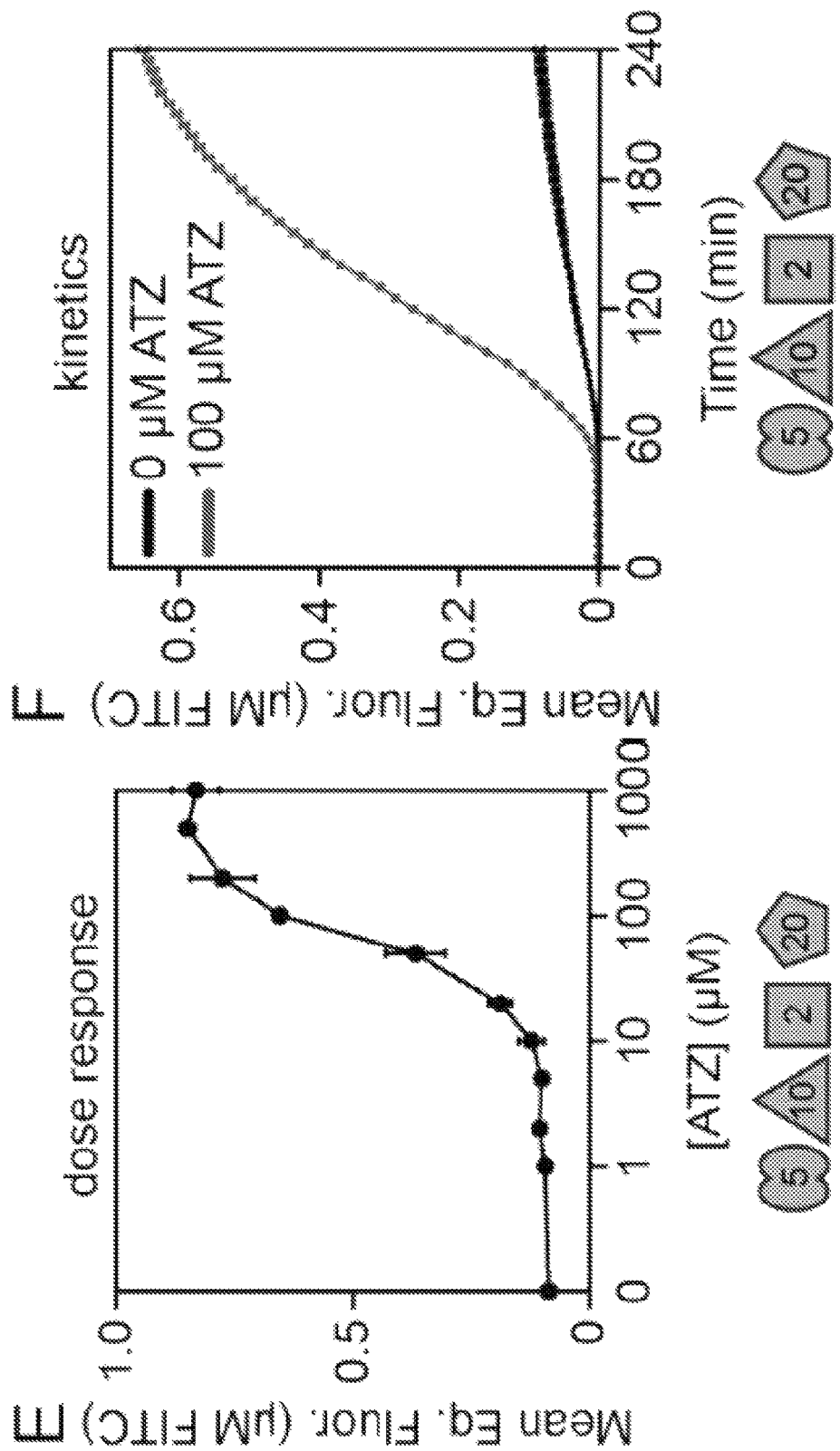

Having established an optimal ratio of each extract in our sensor, we measured its dose response to atrazine (See FIG. 22E). The calculated limit of detection above background was approximately 20 µM atrazine, which is consistent with the previous result obtained for the cyanuric acid-only sensor, suggesting that the enzymatic conversion steps are likely not limiting the sensor's limit of detection. The half-maximal signal is observed at around 66 µM. In total, the cell-free sensor achieves approximately seven-fold induction in response to 100 µM atrazine, with a kinetic divergence in the response at approximately one hour (See FIG. 22F), an improvement in both speed and activation rate over the state-of-the-art in whole-cell atrazine biosensing.[27]

Figure 23:
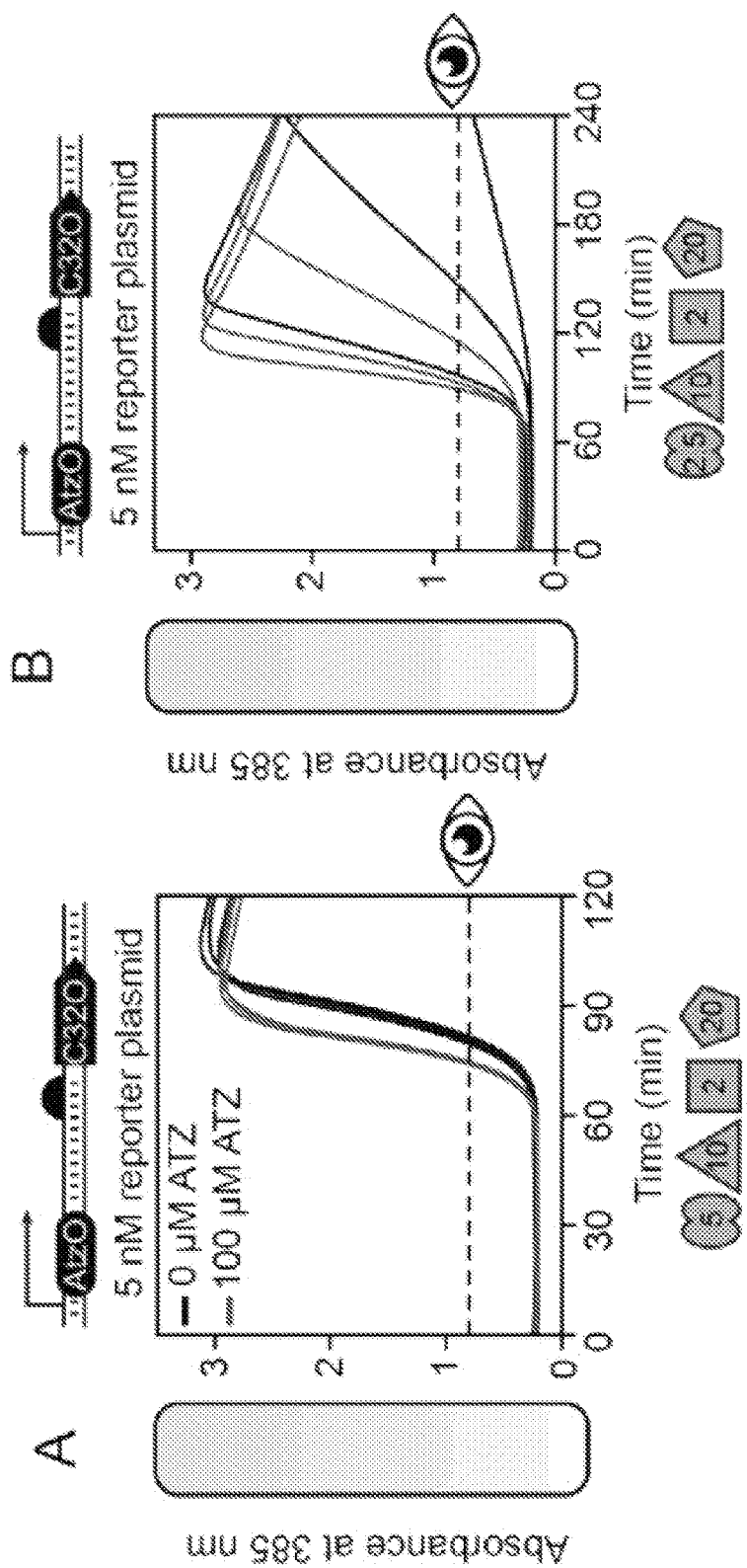
FIG. 23. Implementation and optimization of a colorimetric atrazine biosensor. (A) Replacing the sfGFP reporter in the functional atrazine sensor with the gene encoding catechol 2,3-dioxygenase (C23O) results in poor discrimination in the ON and OFF state due to large amounts of sensor leak. The x-axis scale has been shortened to exaggerate the separation difference between the purple (ON) and black (OFF) traces. (B) Decreasing the atzR extract ratio diminishes leak in the OFF state but increases the time to coloration in the ON state and also increases experimental variability. (C) Decreasing the reporter DNA concentration suppresses OFF state leak more effectively without impacting the speed of the ON state. (D) Introducing a known mutation to C32O to decrease the enzyme's turnover number only suppresses leak to an extent. (E) Dose response with the colorimetric reporter. Decreasing concentrations of atrazine prepared in laboratory water samples were supplied to freeze-dried cell-free reactions to determine the limit of detection of the leakless sensor. The limit of detection was estimated to occur between 100 nM and 1 μM atrazine. In all cases, the individual trajectories from three independent reactions are plotted rather than averages.
Figure 23:
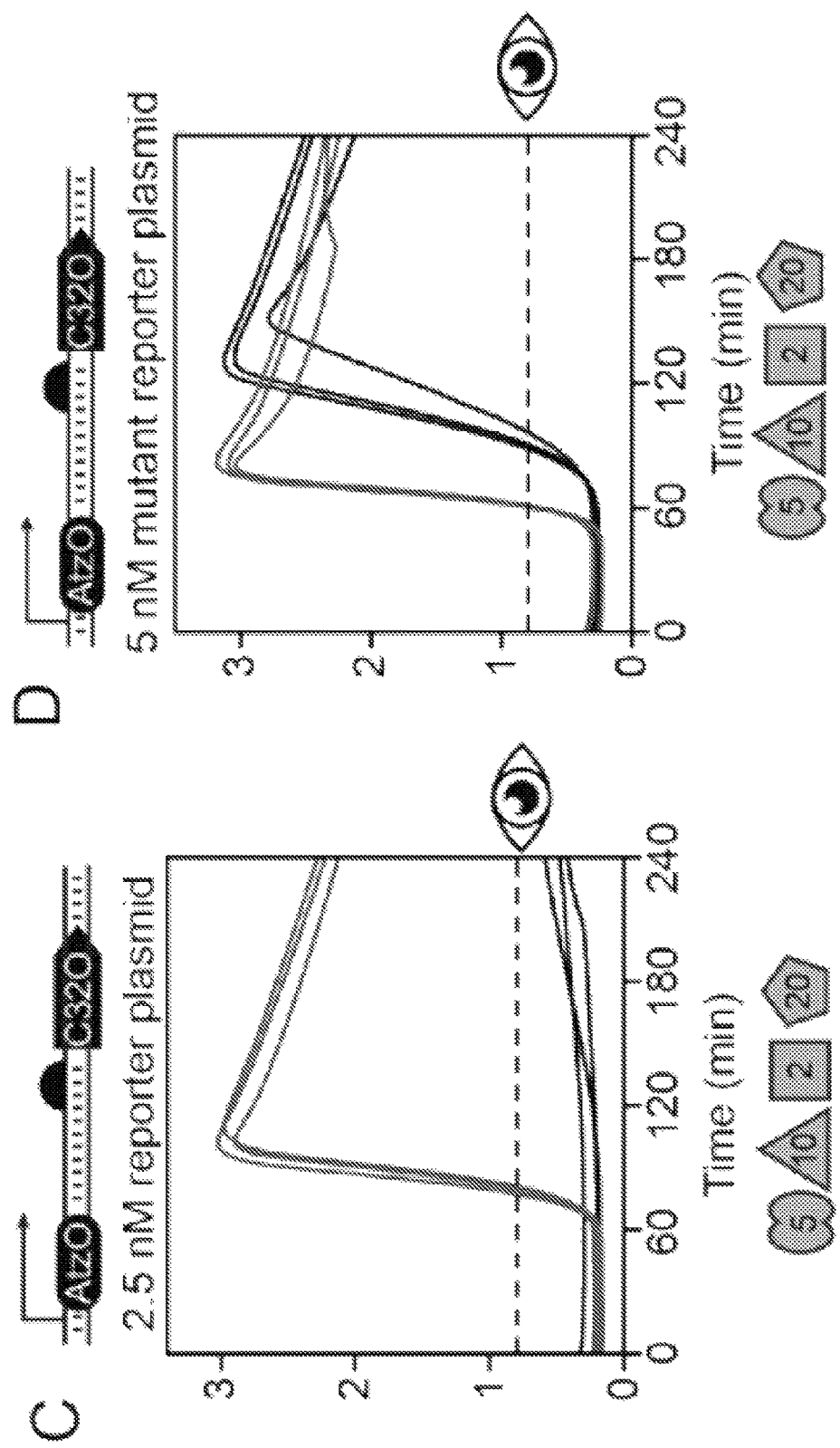
Figure 23:
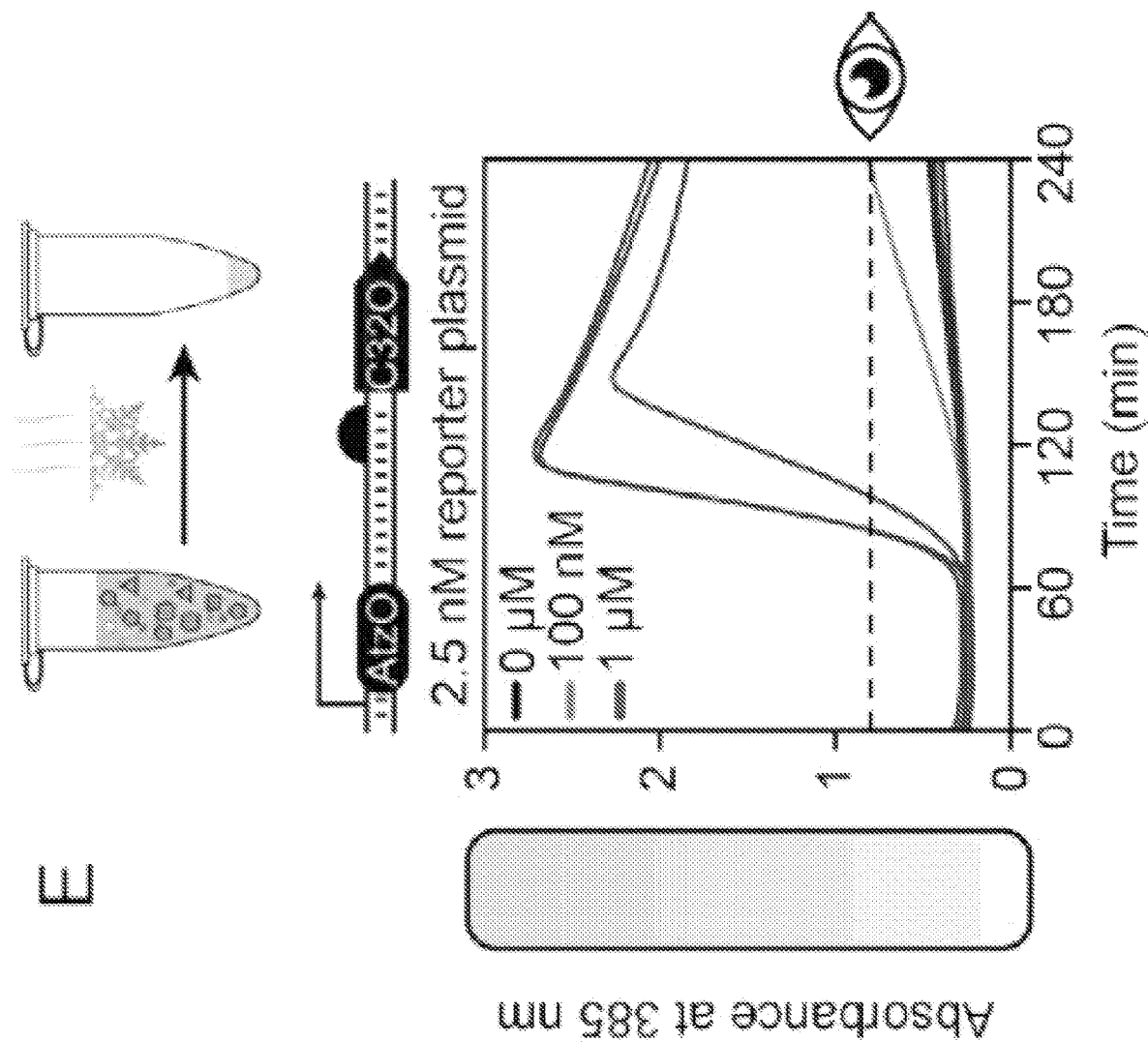

Tuned colorimetric reporters enhance sensor limit of detection and enable field detection. Despite this success, we acknowledge that the legal limit of atrazine in drinking water is 3 ppb (~13 nM), which is three orders of magnitude lower than our reported limit of detection using a fluorescent reporter. We hypothesized that we could qualitatively measure lower concentrations of atrazine by replacing the fluorescent reporter with an enzymatic reporter, since very low levels of high-turnover enzymes can be efficiently detected over background. We therefore designed a new reporter plasmid with the sfGFP coding sequence replaced by catechol 2,3-dioxygenase (C23O), an enzyme which hydrolyzes a colorless substrate, catechol, into 2,3-cis,cis-muconic acid, which is yellow in color. We quickly observed a drawback of using colorimetric reporters: a small amount of leak in the OFF state will eventually always lead to circuit activation, so the only measurable output is the sensor's speed of response. We observed this effect in an unoptimized version of the sensor, where the difference between the ON and OFF states of the sensor was only about 5-10 minutes, as measured by the separation timescale at an empirically-chosen visible threshold (A385=0.8) (See FIG. 23A).

Since the colorimetric output effectively turns the sensor into a binary switch, to determine a realistic limit of detection for the sensor, we required that it remain in the OFF state over the course of the sensing reaction, which we chose to last four hours. Thus, a reduction in the leak of the colorimetric sensor was necessary, ideally without simultaneously slowing down the ON state too much. We tried three approaches. In the first, we reduced the ratio of activator-enriched extract in the reaction to 2.5% from 5%, which did efficiently reduce the sensor leak, but also produced large sample-sample variability (See FIG. 23B), likely because the reaction is highly sensitive to atzR availability when the transcription factor is limiting. In another approach to reduce sensor leak, we cut the concentration of reporter DNA in half. This effected much better discrimination of ON signal from OFF signal over the course of the experiment, suppressing sensor leak fully in the OFF state for four hours, without diminishing the speed of the ON state (See FIG. 23C). Finally, we designed a mutant version of the C23O reporter with a Y218H point mutation, a variant which is known to have around a four-fold lower $k_{cat}$.[29] Since the C23O oxidation reaction is otherwise extremely rapid, we hypothesized that decreasing the enzyme's velocity would make the rate at which absorbance increases more sensitive to the actual enzyme concentration. Though it did separate the ON and OFF trajectories somewhat (See FIG. 23D), this approach was somewhat less effective than reducing the reporter DNA concentration.

Having sufficiently suppressed the leak by reducing the plasmid supplied to the reaction, we aimed to determine an accurate limit of detection by replicating in-use conditions as best as possible. We freeze-dried identical sensor reactions and rehydrated them across a log-fold dilution series of atrazine, from 1 mM atrazine down to 1 nM. At these conditions, we observed a clear limit of detection for the enzymatic reporter at 1 where all three technical replicates reactions turned on within a four-hour limit, and nothing turned on in the water-only control (See FIG. 23E). One order of magnitude lower in atrazine concentration, at 100 nM, we observed one of the three reactions change color, suggesting that the limit of detection may float in the hundreds of nanomolar range. Although this concentration is higher than the EPA-set legal limit for drinking water (3 ppb=13 nM), it is in the range of some of the most egregious examples of atrazine contamination detected in a watershed (238 ppb=1.1 µM) and approaches the highest concentration detected in a finished drinking water source (40 ppb=185 nM) by a National Resources Defense Council study.[23]

Example 5

Development of Cell-Free System for Detecting Nitrate

We aimed to develop a cell-free sensor for nitrate, a common fertilizer and contaminant of groundwater in the United States, which can have severe health risks when consumed by infants.

Figure 24:
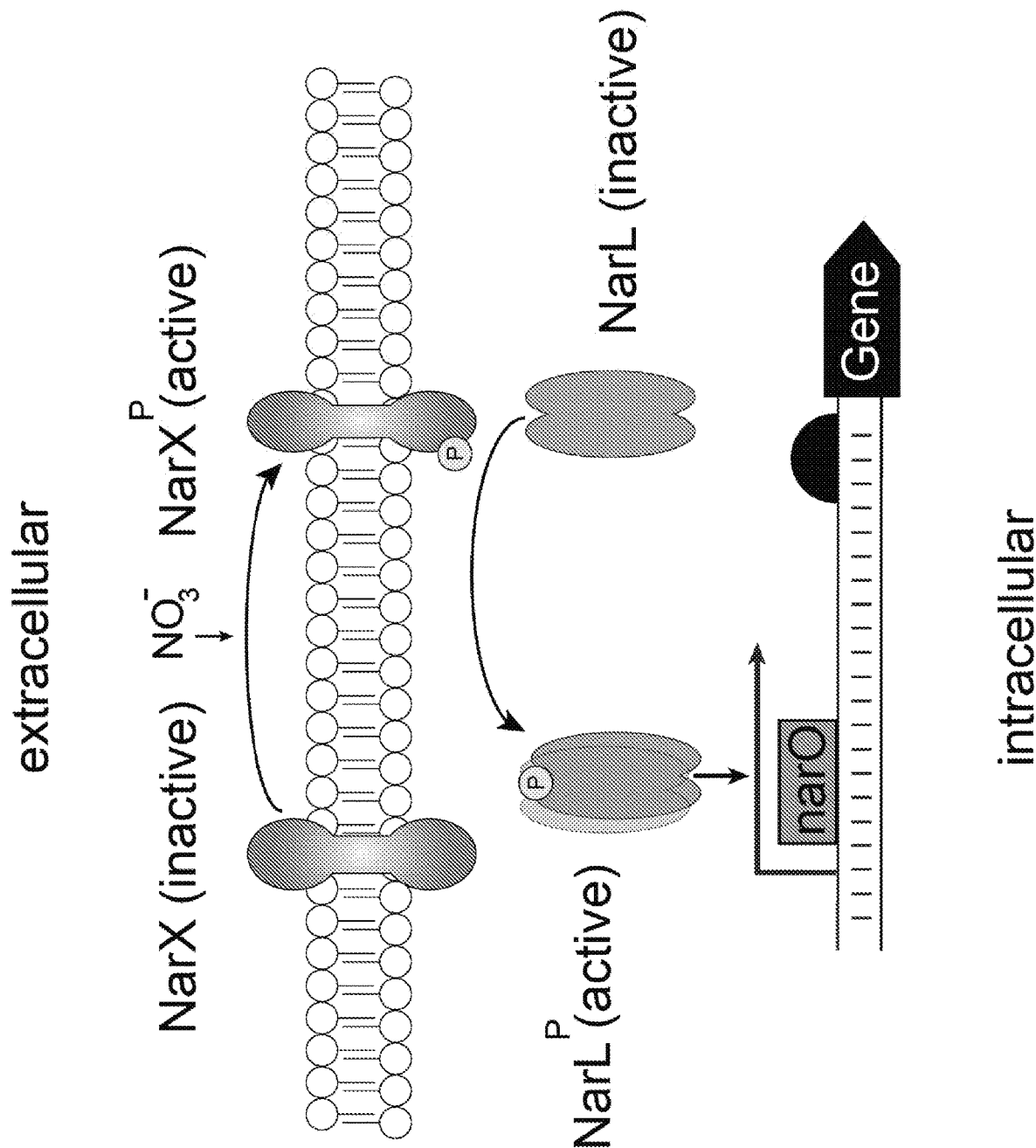
FIG. 24. General scheme for nitrate sensing.

Whole-cell sensors have been previously developed for nitrate using the native sensing pathway from *E. coli*, a two-component system, which relies on a membrane-bound sensing component (NarX) and an intracellular response regulator protein (NarL) that serves as a transcription factor. Upon binding extracellular nitrate, NarX autophosphorylates on its cytoplasmic domain and activates phosphorylation of NarL, which then is capable of binding to DNA and activating transcription by the native *E. coli* RNAP (See FIG. 24).

We thus set out to develop a cell-free system for detecting nitrate using extracts enriched with the nitrate sensor protein NarX and the nitrate response regulator protein NarL. No previous work to our knowledge has demonstrated a functional two-component system in a cell-free protein synthesis reaction, but we hypothesized that our enriched extract approach coupled with the strategy of metabolic conversion could be generalized to the phosphorylation cascade necessary for this protein network. Moreover, previous work has shown that membrane-bound proteins like glycosyltransferases and ATP synthase retain their activity in extracts when pre-enriched in the host bacterial strain.[30,32]

Figure 25:
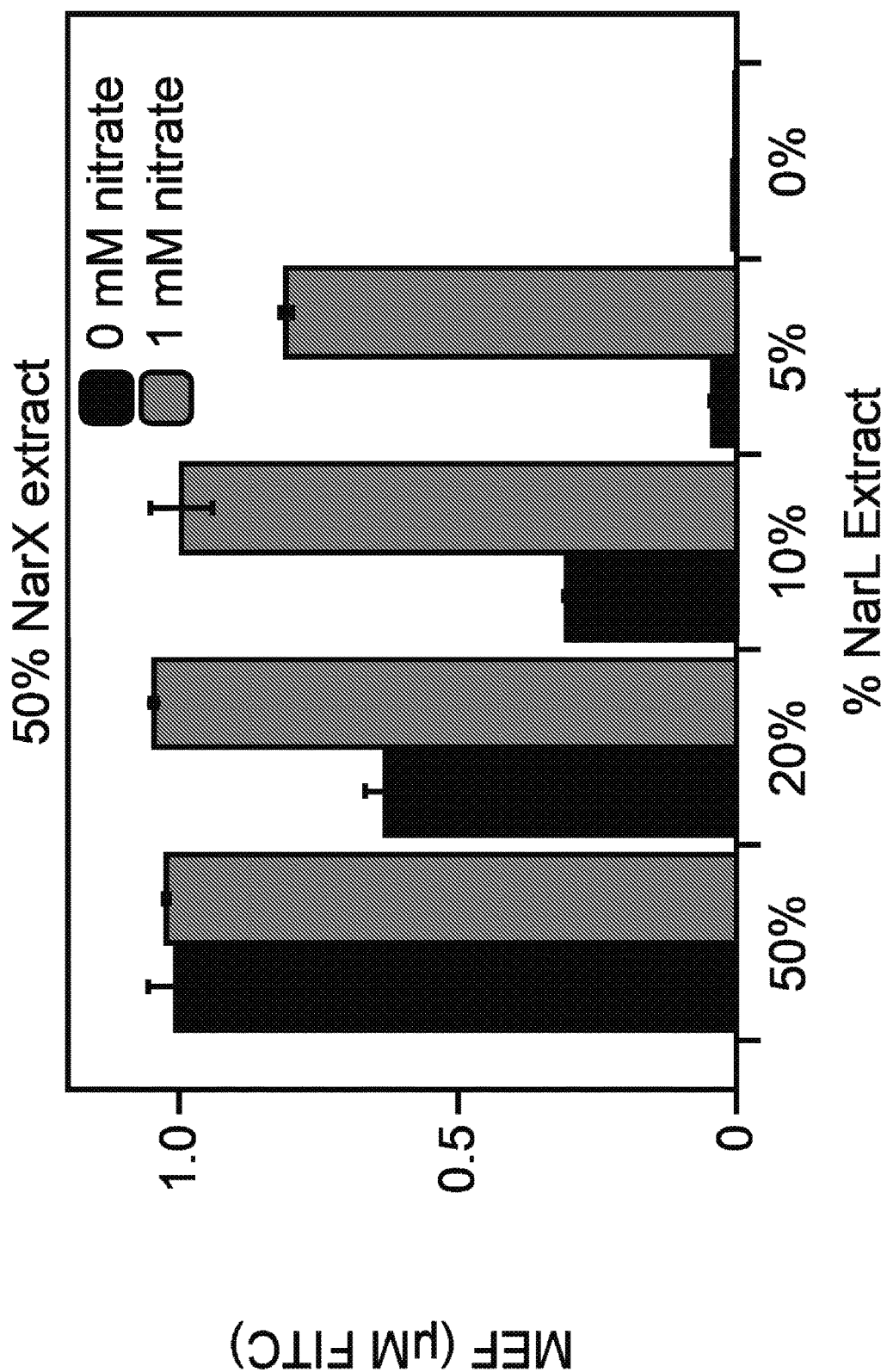
FIG. 25. Sensing of nitrate in cell-free system using NarL-enriched extract.
Figure 26:
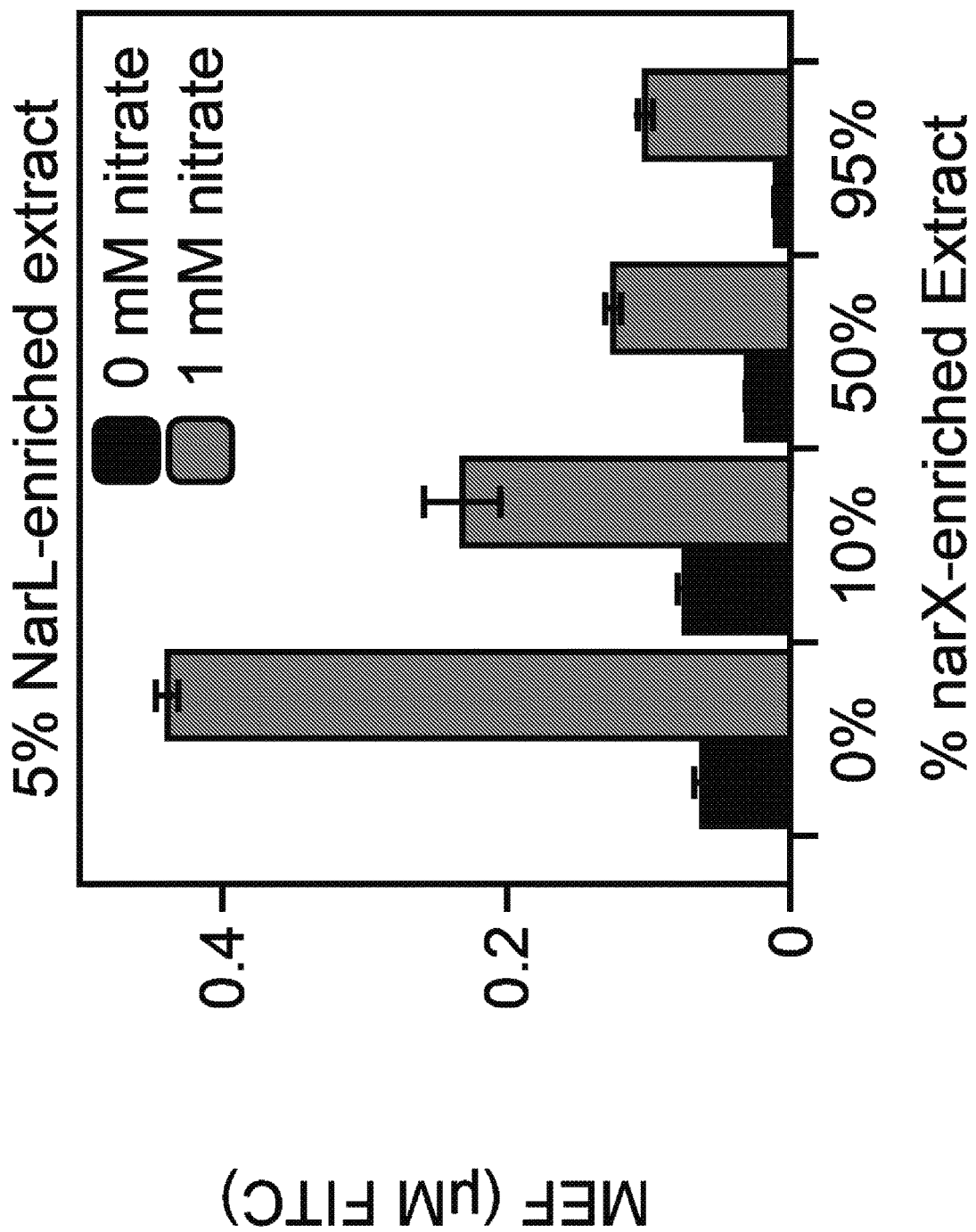
FIG. 26. Sensing of nitrate in cell-free system in the absence of supplemented NarX.
Figure 27:
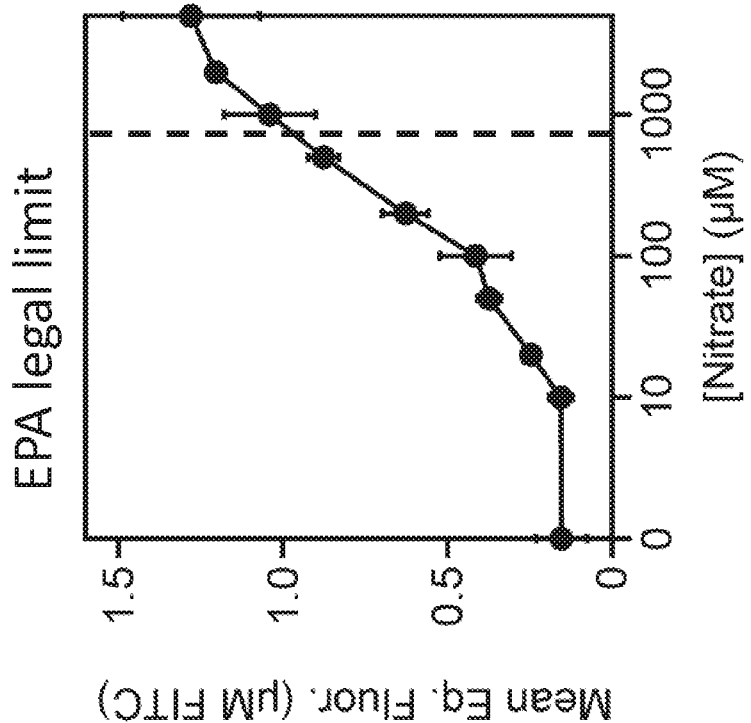
FIG. 27. The dose response of the cell-free system to nitrate is more sensitive than the environmental limit.

We enriched separate extracts with NarX and NarL and observed robust detection of nitrate at 1 mM at certain ratios of these extracts (See FIGS. 25 and 26). We observed that our nitrate sensor was activated by 1 mM nitrate even in the absence of supplemental NarX, likely owing to background expression of NarX from the host strain (See FIG. 26). At the optimal conditions with the sfGFP reporter, our cell-free system's sensitivity to nitrate is more sensitive than the environmental limit (See FIG. 27).

Figure 28:
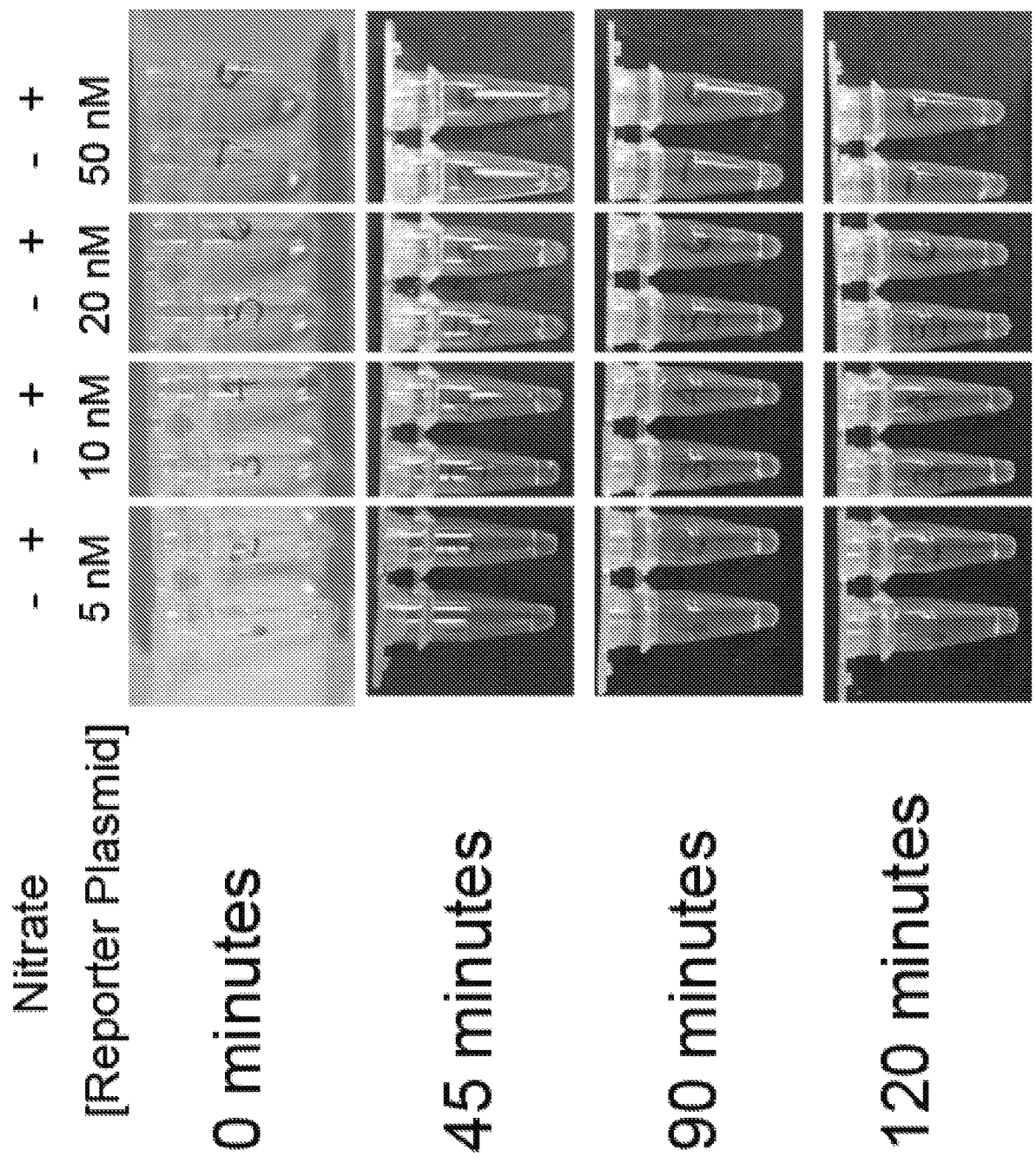
FIG. 28. Design of a colorimetric reporter to improve nitrate sensor utility for field water testing.
Figure 29:
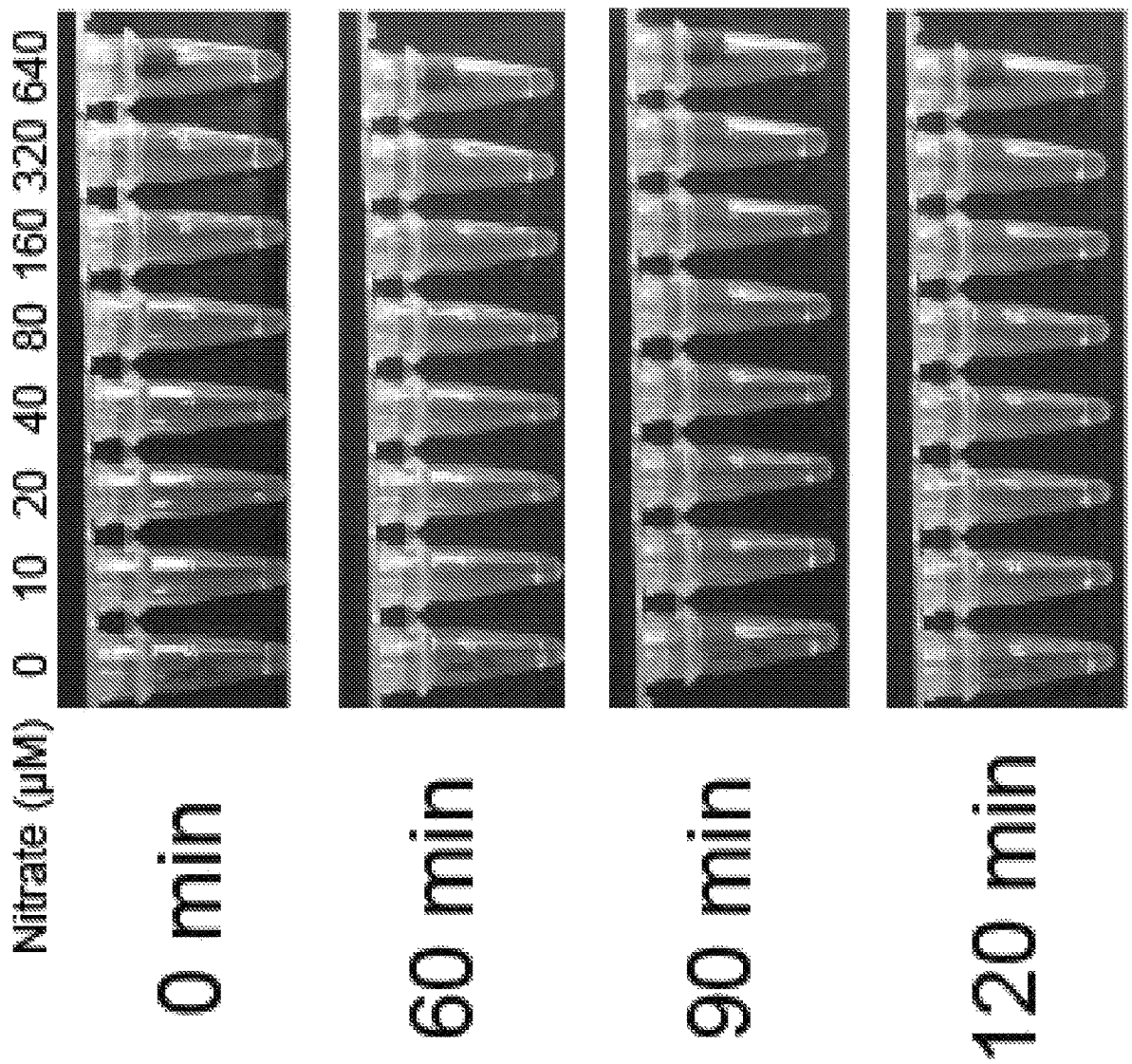
FIG. 29. Colorimetric dose/time response to nitrate.

We next prepared a colorimetric assay for nitrate by replacing our fluorescent protein with an enzyme (C32O) which cleaves its substrate catechol to generate a yellow by-product (See FIG. 28). The output that was generated in our system was visible by the naked eye and could detect nitrate at a concentration as low as 10 µM. (See FIG. 29).

REFERENCES

Non-Patent References

1 Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
2 Jewett, M. C. & Swartz, J. R. Mimicking the *Escherichia coli* cytoplasmic environment activates long-lived and efficient cell-free protein synthesis. Biotechnology and Bioengineering 86, 19-26, doi:10.1002/bit.20026 (2004).
3 Jewett, M. C., Calhoun, K. A., Voloshin, A., Wuu, J. J. & Swartz, J. R. An integrated cell-free metabolic platform for protein production and synthetic biology. Molecular systems biology 4, 220-220, doi:10.1038/msb.2008.57 (2008).
4 Siegal-Gaskins, D., Tuza, Z. A., Kim, J., Noireaux, V. & Murray, R. M. Gene Circuit Performance Characterization and Resource Usage in a Cell-Free "Breadboard". ACS Synthetic Biology 3, 416-425, doi:10.1021/sb400203p (2014).
5 Karim, A. S. & Jewett, M. C. A cell-free framework for rapid biosynthetic pathway prototyping and enzyme discovery. Metabolic Engineering 36, 116-126, doi:doi.org/10.1016/j.ymben.2016.03.002 (2016).
6 Chappell, J., Jensen, K. & Freemont, P. S. Validation of an entirely in vitro approach for rapid prototyping of DNA regulatory elements for synthetic biology. Nucleic Acids Research 41, 3471-3481, doi:10.1093/nar/gkt052 (2013).
7 Zawada, J. F. et al. Microscale to manufacturing scale-up of cell-free cytokine production—a new approach for shortening protein production development timelines. Biotechnology and Bioengineering 108, 1570-1578, doi:doi:10.1002/bit.23103 (2011).
8 Thoring, L., Dondapati, S. K., Stech, M., Wüstenhagen, D. A. & Kubick, S. High-yield production of "difficult-to-express" proteins in a continuous exchange cell-free system based on CHO cell lysates. Scientific reports 7, 11710-11710, doi:10.1038/s41598-017-12188-8 (2017).
9 Silverman, A., Kelley-Loughnane, N., Lucks, J. B. & Jewett, M. C. Deconstructing cell-free extract preparation for in vitro activation of transcriptional genetic circuitry. ACS Synthetic Biology, doi:10.1021/acssynbio.8b00430 (2018).
10 Alam, K. K. et al. Rapid, Low-Cost Detection of Water Contaminants Using Regulated In Vitro Transcription. bioRxiv, 619296, doi:10.1101/619296 (2019).
11 Pardee, K. et al. Paper-Based Synthetic Gene Networks. Cell 159, 940-954, doi:10.1016/j.cell.2014.10.004.
12 Pardee, K. et al. Rapid, Low-Cost Detection of Zika Virus Using Programmable Biomolecular Components. Cell 165, 1255-1266, doi:10.1016/j.cell.2016.04.059.
13 Ma, D., Shen, L., Wu, K., Diehnelt, C. W. & Green, A. A. Low-cost detection of norovirus using paper-based cell-free systems and synbody-based viral enrichment. Synthetic Biology 3, ysy018-ysy018, doi:10.1093/synbio/ysy018 (2018).
14 Gräwe, A. et al. A paper-based, cell-free biosensor system for the detection of heavy metals and date rape drugs. PLOS ONE 14, e0210940, doi:10.1371/journal.pone.0210940 (2019).
15 Didovyk, A., Tonooka, T., Tsimring, L. & Hasty, J. Rapid and Scalable Preparation of Bacterial Lysates for Cell-Free Gene Expression. ACS synthetic biology 6, 2198-2208, doi:10.1021/acssynbio.7b00253 (2017).
16 Karig, D. K., Iyer, S., Simpson, M. L. & Doktycz, M. J. Expression optimization and synthetic gene networks in cell-free systems. Nucleic acids research 40, 3763-3774, doi:10.1093/nar/gkr1191 (2012).
17 Wang, H., Li, J. & Jewett, M. C. Development of a *Pseudomonas putida* cell-free protein synthesis platform for rapid screening of gene regulatory elements. Synthetic Biology 3, ysy003-ysy003, doi:10.1093/synbio/ysy003 (2018).
18 Zubay, G. In vitro synthesis of protein in microbial systems. Annual Review of Genetics 7, 267-287, doi:10.1146/annurev.ge.07.120173.001411 (1973).
19 Shin, J. & Noireaux, V. An *E. coli* Cell-Free Expression Toolbox: Application to Synthetic Gene Circuits and Artificial Cells. ACS Synthetic Biology 1, 29-41, doi:10.1021/sb200016s (2012).
20 Kwon, Y.-C. & Jewett, M. C. High-throughput preparation methods of crude extract for robust cell-free protein synthesis. Scientific Reports 5, 8663, doi:10.1038/srep08663 (2015).
21 Shin, J. & Noireaux, V. Efficient cell-free expression with the endogenous *E. Coli* RNA polymerase and sigma factor 70. Journal of Biological Engineering 4, 8-8, doi:10.1186/1754-1611-4-8 (2010).
22 Shindo, T., Ueda, H., Suzuki, E. & Nishimura, H. A Catechol 2,3-Dioxygenase Gene as a Reporter. Bioscience, Biotechnology, and Biochemistry 59, 314-315, doi:10.1271/bbb.59.314 (1995).
23 Wu, M., Quirindongo, M., Sass, J. & Wetzler, A. Still Poisoning the Well: Atrazine Continues to Contaminate Surface Water and Drinking Water in the United States. (Natural Resources Defence Council, Online, 2010).
24 Platero, A. I., Garcia-Jaramillo, M., Santero, E. & Govantes, F. Transcriptional organization and regulatory elements of a *Pseudomonas* sp. strain ADP operon encoding a LysR-type regulator and a putative solute transport system. Journal of bacteriology 194, 6560-6573, doi:10.1128/JB.01348-12 (2012).
25 de Souza, M. L., Seffernick, J., Martinez, B., Sadowsky, M. J. & Wackett, L. P. The Atrazine Catabolism Genes <em>atzABC</em> Are Widespread and Highly Conserved. Journal of Bacteriology 180, 1951-1954 (1998).
26 Voyvodic, P. L., Pandi, A., Koch, M., Faulon, J.-L. & Bonnet, J. Plug-and-Play Metabolic Transducers Expand the Chemical Detection Space of Cell-Free Biosensors. bioRxiv, doi:10.1101/397315 (2018).
27 Hua, A., Gueuné, H., Cregut, M., Thouand, G. & Durand, M.-J. Development of a bacterial bioassay for atrazine and cyanuric acid detection. Frontiers in microbiology 6, 211-211, doi:10.3389/fmicb.2015.00211 (2015).
28 Takahashi, M. K. et al. Rapidly characterizing the fast dynamics of RNA genetic circuitry with cell-free transcription-translation (TX-TL) systems. ACS synthetic biology 4, 503-515, doi:10.1021/sb400206c (2015).
29 Junca, H., Plumeier, I., Hecht, H.-J. & Pieper, D. H. Difference in kinetic behaviour of catechol 2,3-dioxygenase variants from a polluted environment. Microbiology 150, 4181-4187, doi:doi:10.1099/mic.0.27451-0 (2004).
30 Schoborg, J. A. et al. A cell-free platform for rapid synthesis and testing of active oligosaccharyltransferases. Biotechnology and Bioengineering 115, 739-750, doi:doi:10.1002/bit.26502 (2018).
31 Jaroentomeechai, T. et al. Single-pot glycoprotein biosynthesis using a cell-free transcription-translation system 32 Jewett, M. C. & Swartz, J. R. Substrate replenishment extends protein synthesis with an in vitro translation system designed to mimic the cytoplasm. Biotechnology and Bioengineering 87, 465-471, doi:10.1002/bit.20139 (2004).

33 Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).

34 Caschera, F. & Noireaux, V. Synthesis of 2.3 mg/ml of protein with an all *Escherichia coli* cell-free transcription-translation system. Biochimie 99, 162-168, doi:10.1016/j.biochi.2013.11.025 (2014).

35 Zawada, J. F. et al. Microscale to manufacturing scale-up of cell-free cytokine production—a new approach for shortening protein production development timelines. Biotechnology and bioengineering 108, 1570-1578, doi: 10.1002/bit.23103 (2011).

36 Yang, W. C. et al. Cell-free production of transducible transcription factors for nuclear reprogramming. Biotechnology and bioengineering 104, 1047-1058, doi:10.1002/bit.22517 (2009).

37 Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).

38 Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).

39 Shin, J. & Noireaux, V. An *E. coli* cell-free expression toolbox: application to synthetic gene circuits and artificial cells. ACS synthetic biology 1, 29-41, doi:10.1021/sb200016s (2012).

40 Studier, F. W. & Moffatt, B. A. Use of bacteriophage T7 RNA polymerase to direct selective high-level expression of cloned genes. Journal of molecular biology 189, 113-130 (1986).

41 Kwon, Y. C. & Jewett, M. C. High-throughput preparation methods of crude extract for robust cell-free protein synthesis. Scientific reports 5, 8663, doi:10.1038/srep08663 (2015).

42 Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).

43 Sun, Z. Z., et al., Protocols for Implementing an *Escherichia coli* Based TX-TL Cell-Free Expression System for Synthetic Biology. 2013(79): p. e50762.

44 Wen, K. Y., et al., A Cell-Free Biosensor for Detecting Quorum Sensing Molecules in *P. aeruginosa*-Infected Respiratory Samples. ACS Synthetic Biology, 2017. 6(12): p. 2293-2301.

45 Jia, K., et al., A lower limit of detection for atrazine was obtained using bioluminescent reporter bacteria via a lower incubation temperature. Ecotoxicology and Environmental Safety, 2012. 84: p. 221-226.

46 Garcia-Gonzalez, V., et al., Regulation of the *Pseudomonas* sp. Strain ADP Cyanuric Acid Degradation Operon. Journal of Bacteriology, 2005. 187(1): p. 155-167.

Patent References

U.S. Pat. Nos. 5,478,730; 5,556,769; 5,665,563; 6,168,931; 6,518,058; 6,783,957; 6,869,774; 6,994,986; 7,118,883; 7,189,528; 7,338,789; 7,387,884; 7,399,610; 8,357,529; 8,574,880; 8,703,471; 8,999,668; 9,410,170; and 9,528,13; the contents of which are incorporated herein by reference in their entirety.

U.S. Patent Publications: US20040209321; US20050170452; US20060211085; US20060234345; US20060252672; US20060257399; US20060286637; US20070026485; US20070154983; US20070178551; US20080138857; US20140295492; US20160060301; US20180016612; US20180016614; US20160312312; and US20160362708; the contents of which are incorporated herein by reference in their entirety.

Published International Applications: WO2003056914A1; WO2004013151A2; WO2004035605A2; WO2006102652A2; WO2006119987A2; WO2007120932A2; WO2014144583; and WO2017117539; the contents of which are incorporated herein by reference in their entirety.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of detecting a target molecule in a biological or environmental sample, the method comprising:
   (i) obtaining a biological or environmental sample which may or may not contain the target molecule,
   (ii) adding the sample to a cell-free protein synthesis (CFPS) reaction comprising:
      (a) a cell extract prepared from one or more host strains, wherein the one or more host strains comprise: transcription-translation reagents, energy, cofactor regeneration;
      (b) one or more target molecule metabolizing enzymes; and
      (c) a nucleic acid reporter construct encoding a reporter molecule operably linked to a regulatory element that is regulated by a metabolite of the target molecule;
         wherein, in the presence of the target molecule, the one or more target molecule metabolizing enzymes generates the metabolite of the target molecule;

wherein the metabolite of the target molecule triggers generation of a detectable output via expression of the reporter molecule from the reporter construct, the detectable output comprising a visual, electronic, or optical output.

2. The method of claim 1, wherein the cell-free protein synthesis reaction comprises:
exogenous supplied polymerase.

3. The method of claim 1, wherein the reporter molecule comprises a protein, and wherein the visual, electronic, or optical output is generated by the reporter protein expressed from the reporter construct.

4. The method of claim 3, wherein the CFPS comprises a transcription factor, wherein
(a) the transcription factor is activated by the metabolite of the target molecule, and wherein the reporter protein is expressed in response to binding of the activated transcription factor to the regulatory element of the reporter construct; or
(b) the transcription factor is a repressor molecule capable of binding to the regulatory element of the reporter construct, thereby preventing expression of the reporter protein,
wherein the repressor molecule is deactivated by the metabolite of the target molecule,
and wherein the reporter protein is expressed in response to the deactivation of the repressor molecule.

5. The method of claim 4, wherein the transcription factor and the reporter protein are synthesized via CFPS in the same pot.

6. The method of claim 4, wherein the transcription factor is synthesized in situ via CFPS in a first pot and the reporter protein is synthesized in situ via CFPS in a second pot to which the first pot comprising the transcription factor is added.

7. The method of claim 4, wherein the transcription factor is overexpressed in the host strain to enrich it in the cell extract used for the CFPS reaction.

8. The method of claim 7, wherein the transcription factor-enriched extract is added to a host strain extract that is not enriched for any specific protein to yield a final extract for the CFPS reaction of the reporter protein.

9. The method of claim 4, wherein the transcription factor is separately expressed from cells and purified, and the purified transcription factor is then mixed directly into the CFPS reaction.

10. The method of claim 1, wherein the visual, electronic, or optical output is generated from an enzymatic reaction catalyzed by the metabolite of the target molecule that is generated in the CFPS reaction.

11. The method of claim 1, wherein at least one of the one or more host strains overexpresses the one or more target molecule metabolizing enzymes.

12. The method of claim 1, wherein the one or more target molecule metabolizing enzymes are overexpressed in the host strain prior to making the cell extract for the CFPS reaction.

13. The method of claim 1, wherein two or more of the one or more target molecule metabolizing enzymes are overexpressed in two or more different host strains individually or in groups and the cell extract for the CFPS reaction is prepared by combining cell extracts from the two or more different host strains.

14. The method of claim 1, wherein the one or more target molecule metabolizing enzymes are expressed in the CFPS reaction.

15. The method of claim 1, wherein one or more of the one or more target molecule metabolizing enzymes are overexpressed in the host strain prior to making the cell extract for the CFPS reaction and wherein one or more of the one or more target molecule metabolizing enzymes are expressed in the CFPS reaction.

16. A device or kit comprising components for detecting a target molecule according to claim 1, wherein the components comprise preserved CFPS reaction components.

17. The method of claim 1, wherein at least one of the one or more host strains of (a) is not engineered, and wherein at least one of the one or more host strains of (a) is engineered to express a transcription factor, one or more target molecule metabolizing enzymes, or both.

18. The method of claim 1, further comprising concentrating and/or solubilizing the target molecule.

19. The method of claim 1, wherein the one or more target molecule metabolizing enzymes are exogenously produced and purified, and are added to the CFPS reaction.

20. The method of claim 4, wherein the transcription factor is phlF, the target molecule is phloroglucinol, and the metabolite of the target molecule is diacetylphloroglucinol; and/or
(b) the transcription factor is AtzR, the target molecule is atrazine, and the metabolite of the target molecule is cyanuric acid.

21. A method of detecting a target molecule in a biological or environmental sample, the method comprising:
(i) obtaining a biological or environmental sample which may or may not contain the target molecule;
(ii) adding the sample to a cell-free protein synthesis (CFPS) reaction comprising:
(a) a cell extract prepared from one or more host strains, wherein the one or more host strains comprise: transcription-translation reagents, energy, cofactor regeneration;
(b) a nucleic acid reporter construct encoding a reporter molecule operably linked to a regulatory element that is regulated by the target molecule;
wherein the target molecule triggers generation of a detectable output via expression of the reporter molecule from the reporter construct, the detectable output comprising a visual, electronic, or optical output;
wherein the transcription-translation reagents comprise a membrane-bound kinase and a soluble DNA-binding response regulator and the membrane-bound kinase regulates the activity of the soluble DNA-binding response regulator.

\* \* \* \* \*